(12) United States Patent
Fisher et al.

(10) Patent No.: US 11,331,395 B2
(45) Date of Patent: *May 17, 2022

(54) HYDROGEL PRODRUG FOR TREATMENT

(71) Applicant: Viking Scientific, Inc., San Marcos, CA (US)

(72) Inventors: Paul Fisher, Oceanside, CA (US); Paulina Davis, San Marcos, CA (US)

(73) Assignee: Viking Scientific, Inc., Oceanside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/563,533

(22) Filed: Sep. 6, 2019

(65) Prior Publication Data

US 2021/0030890 A1    Feb. 4, 2021

Related U.S. Application Data

(63) Continuation of application No. 15/630,645, filed on Jun. 22, 2017, now Pat. No. 10,406,241, which is a
(Continued)

(51) Int. Cl.
*A61K 47/69* (2017.01)
*A61K 47/60* (2017.01)
(Continued)

(52) U.S. Cl.
CPC ........ *A61K 47/6903* (2017.08); *A61K 9/0019* (2013.01); *A61K 9/06* (2013.01);
(Continued)

(58) Field of Classification Search
None
See application file for complete search history.

(56) References Cited

U.S. PATENT DOCUMENTS

| 3,867,329 A | 2/1975 | Halpern et al. |
| 6,689,350 B2 | 2/2004 | Uhrich |

(Continued)

FOREIGN PATENT DOCUMENTS

| WO | WO 07/120818 | 10/2007 |
| WO | WO 12/112982 | 8/2012 |

(Continued)

OTHER PUBLICATIONS

Anderson et al., 2006, A combinatorial library of photocrosslinkable and degradable materials, Advanced Materials, 18(19):2614-2618.
(Continued)

*Primary Examiner* — Melissa S Mercier
(74) *Attorney, Agent, or Firm* — Knobbe, Martens, Olson & Bear, LLP

(57) ABSTRACT

Aspects of the invention described herein include a hydrogel prodrug and methods of making a hydrogel prodrug for drug delivery. Also contemplated are methods of treating, inhibiting, ameliorating or inhibiting a disease or disorder. Without being limiting, the methods for treatment can be directed to a cancer, HIV, a virus, pain, a bacterial infection, a neurological disorder, hemorrhaging, multiple sclerosis, diabetes, high blood pressure, Alzheimer's, or inhibiting a fungal growth in a subject in need.

11 Claims, 53 Drawing Sheets

Related U.S. Application Data continuation-in-part of application No. PCT/US2016/067864, filed on Dec. 20, 2016.

(60) Provisional application No. 62/387,506, filed on Dec. 23, 2015.

(51) Int. Cl.

| | | |
|---|---|---|
| *A61K 47/55* | (2017.01) | |
| *A61K 47/59* | (2017.01) | |
| *A61K 31/195* | (2006.01) | |
| *A61K 31/197* | (2006.01) | |
| *A61K 31/198* | (2006.01) | |
| *A61K 31/245* | (2006.01) | |
| *A61K 31/522* | (2006.01) | |
| *A61K 31/555* | (2006.01) | |
| *A61K 31/606* | (2006.01) | |
| *A61K 31/675* | (2006.01) | |
| *A61K 31/704* | (2006.01) | |
| *A61K 47/34* | (2017.01) | |
| *A61K 9/00* | (2006.01) | |
| *A61K 9/06* | (2006.01) | |
| *A61K 9/14* | (2006.01) | |
| *A61K 9/70* | (2006.01) | |
| *A61K 45/06* | (2006.01) | |
| *A61K 47/08* | (2006.01) | |

(52) U.S. Cl.
CPC .............. *A61K 9/14* (2013.01); *A61K 9/7007* (2013.01); *A61K 31/195* (2013.01); *A61K 31/197* (2013.01); *A61K 31/198* (2013.01); *A61K 31/245* (2013.01); *A61K 31/522* (2013.01); *A61K 31/555* (2013.01); *A61K 31/606* (2013.01); *A61K 31/675* (2013.01); *A61K 31/704* (2013.01); *A61K 45/06* (2013.01); *A61K 47/08* (2013.01); *A61K 47/34* (2013.01); *A61K 47/55* (2017.08); *A61K 47/59* (2017.08); *A61K 47/60* (2017.08)

(56) References Cited

U.S. PATENT DOCUMENTS

| | | | |
|---|---|---|---|
| 7,427,394 | B2 | 9/2008 | Anderson et al. |
| 8,071,082 | B2 | 12/2011 | Zugates et al. |
| 8,642,087 | B1 | 2/2014 | Dziubla et al. |
| 9,034,930 | B2 | 5/2015 | Nair et al. |
| 9,700,627 | B2 | 7/2017 | Langer et al. |
| 10,406,241 | B2 * | 9/2019 | Fisher .................. A61K 47/55 |
| 10,413,616 | B2 | 9/2019 | Fisher et al. |
| 2006/0002590 | A1 * | 1/2006 | Borak .................... G01C 21/32 382/104 |
| 2006/0002890 | A1 | 1/2006 | Hersel et al. |
| 2011/0008404 | A1 | 1/2011 | Lyon et al. |
| 2012/0156259 | A1 | 6/2012 | Rau et al. |
| 2012/0213708 | A1 | 8/2012 | Anderson et al. |
| 2016/0038598 | A1 | 2/2016 | Borrós Gómez et al. |

FOREIGN PATENT DOCUMENTS

| | | |
|---|---|---|
| WO | WO 13/072590 | 6/2013 |
| WO | WO 13/123491 | 8/2013 |

OTHER PUBLICATIONS

International Search Report in application No. PCT/US2016/067864, dated Mar. 3, 2017.

International Search Report and Written Opinion dated Oct. 19, 2018 for Application No. PCT/US2018/038511.

* cited by examiner

7A

7B

11A

11B

12A

Encapsulated liposome formulation
(~24 hour delivery time):

12B

Admixed hydrogel formulation
(<4 hours delivery time):

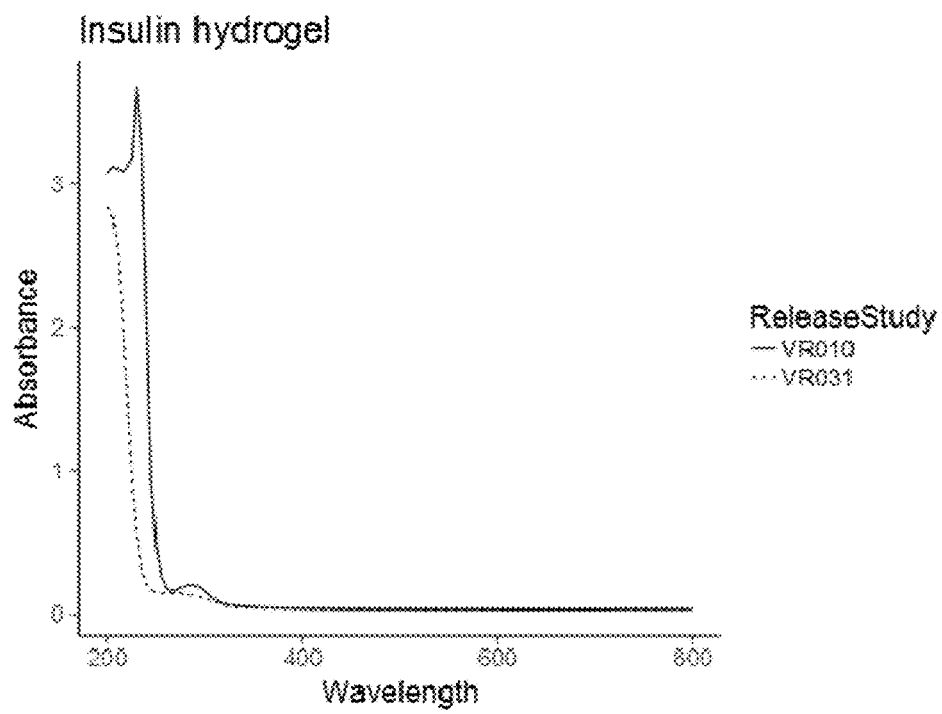
Figure 37
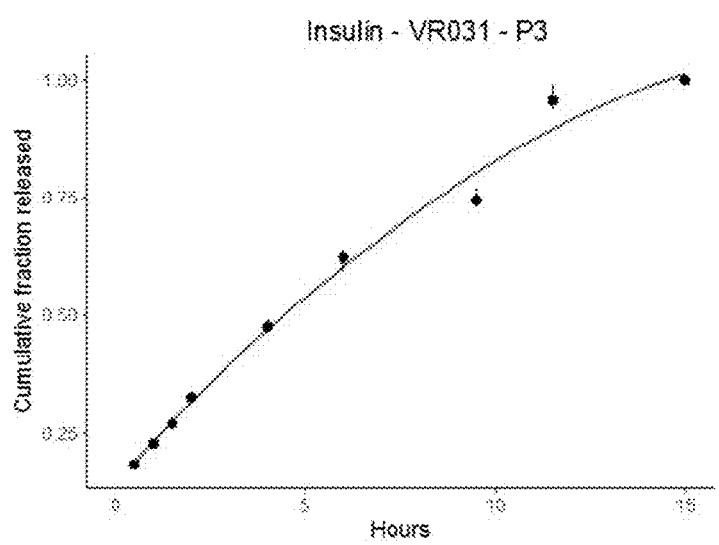

HYDROGEL PRODRUG FOR TREATMENT

INCORPORATION BY REFERENCE TO ANY PRIORITY APPLICATIONS

This application is a continuation application of U.S. patent application Ser. No. 15/630,645 (now U.S. Pat. No. 10,406,241), filed on Jun. 22, 2017, which is a continuation-in-part application of international application PCT/US2016/067864, filed on Dec. 20, 2016, which designated the United States and was published in English and, which claims priority to U.S. provisional patent application 62/387, 506 filed on Dec. 23, 2015. The aforementioned applications are hereby expressly incorporated by reference in their entireties.

FIELD OF THE INVENTION

Aspects of the present invention are directed to systems and compositions that have biologically active molecules incorporated in the backbone structure of a hydrogel prodrug. The hydrogel prodrug can have biologically active molecules including drugs, small molecules and/or peptides incorporated in the backbone structure of the hydrogel prodrug and these hydrogel prodrug formulations can be provided to subjects in need of a therapeutic or cosmetic.

BACKGROUND OF THE INVENTION

Many groups are investigating the use of polymers for the controlled delivery of a variety of therapeutics. Polymers play an integral role in drug delivery and are desirable for controlled release therapeutics, tailored drug release kinetics, increasing the half-life of a drug in a biological system and systems that facilitate the placement and localization of a drug within close proximity of a desired tissue. Controlled drug release is desirable because it can eliminate the potential for both under- and over-dosing. Controlled drug delivery also allows one to more easily maintain consistent drug levels at the desired tissue site, permits less frequent and fewer overall administrations of the drug, and improves patient compliance. Polymer drug delivery systems generally have some disadvantages, including toxicity or non-biocompatibility of the materials used, undesirable degradation by-products, discomfort from implantable polymer drug delivery systems, initial burst release, synthesis and processing conditions that compromise the integrity of the drug or the biocompatibility of the materials, a disconnect between the degradation time of the polymer and the release period of the drug, and the high cost of controlled polymer drug release systems in comparison to standard pharmaceutical compositions.

Controlled delivery of a drug from a polymer occurs when the biologically active ingredient is released from the polymer in a predesigned manner. The release may be periodic over time, it may be constant, or it may be triggered by external events. The drug release kinetics are generally dependent upon the properties of the polymer as well as the drug. Drug may be liberated from the polymer carrier through a variety of methods, including diffusion of drug out the polymer matrix, erosion of the polymer matrix, chemical degradation of the polymer matrix, chemical degradation of a linker between the drug and the polymer matrix, or reduction of an attractive force between the drug and the polymer matrix. Controlled delivery can be preferred, or necessary, when frequent, repeated administration of traditional dosage forms is not feasible or desirable. In many cases, controlled release kinetics provide a therapeutic benefit. The delivery can be tailored so that water-soluble drugs are slowly released and low-solubility drugs are released quickly. The drug delivery can be specific for a target site, or the hydrogel prodrug systems can be designed to be quickly dissolved or degraded for fast elimination. Ideally, the polymer drug system should have an inert backbone, biocompatibility, biodegradability, and the capability of containing a high drug load without the dangers of accidental release. Furthermore, the polymer drug system should be simple to administer and easy to manufacture.

The goal for a polymer controlled drug delivery system is to achieve a delivery profile yielding a constant level of drug in a system or in a target tissue, or periodic drug release in a system or in a target tissue over a determined amount of time, or externally triggered drug release in a system or in a target tissue. In traditional drug dosing, such as oral administration of tablets or injected formulations, the levels of drug initially rise then subsequently fall until a second administration. The metabolism of a patient or the environment in which the drug is placed can lead to an undesired fast degradation, clearance, or waste of the drug before a second administration of drug can occur, and can lead to over-or under-dosing. As such, a polymer system, which achieves a constant level of drug over a given period of time, is greatly needed.

SUMMARY

In a first aspect, a method of making a hydrogel prodrug is provided. The method can include the following: providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is drug comprises at least a two secondary amine groups. In some alternatives, wherein the at least one amine group comprises at least two secondary amine groups. In some alternatives, the method comprises reacting the at least one acrylate with the at least two secondary amine groups of the at least one drug In some alternatives, at least one primary amine and/or at least one secondary amine are provided. In some alternatives, the at least one acrylate can have at least one acrylate group. In some alternatives, the at least one acrylate group is bound by an ester linkage to an opposing termini of a carbon chain. In some alternatives, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000 g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration that is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the method further comprises providing a second drug, wherein, the second drug comprises at least one amine group. In some alternatives, the second drug comprises at least two additional secondary amine groups one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the reacting step is performed for at least or equal to 1, 2, 3, 4, 5, 6, 7, 8, 9, 10, 12, 24, 36, 48 or 72 hours, or within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to the at least one drug of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least one primary amine group of the chemical spacer or at least one secondary amine group of the chemical spacer is attached to a carbon chain. In some alternatives, the spacer comprises isobutylamine. In some alternatives, the carbon chain can have at least or equal to 1, 5, 10, 15, 20, 25 or 30 carbon atoms or any number of carbon atoms within a range defined by any two of the aforementioned values. In some alternatives, the carbon chain has substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. Accordingly, some alternatives comprise the hydrogel prodrug manufactured by any of the approaches above and some alternatives comprise the hydrogel prodrug obtainable from said methods and some embodiments comprise any one or more of the hydrogel prodrugs as described above.

In a second aspect, a hydrogel prodrug delivery system is provided. The hydrogel prodrug delivery system can comprise the hydrogel prodrug manufactured by any one of alternatives described herein. The hydrogel prodrug can be manufactured by the following steps: providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is drug comprises at least a two secondary amine groups. In some alternatives, wherein the at least one amine group comprises at least two secondary amine groups. In some alternatives, the method comprises reacting the at least one acrylate with the at least two secondary amine groups of the at least one drug. In some alternatives, at least one primary amine and/or at least one secondary amine are provided. In some alternatives, the at least one acrylate can have at least one acrylate group. In some alternatives, the at least one acrylate group is bound by an ester linkage to an opposing termini of a carbon chain. In some alternatives, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of 170, 250, 575, 700, 1000, 2000, 3500, 5000, 10000 g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of at least or equal to 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration that is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the method further comprises providing a second drug, wherein, the second drug comprises at least one amine group. In some alternatives, the second drug comprises at least two additional secondary amine groups one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the reacting step is performed for at least or equal to 1, 2, 3, 4, 5, 6, 7, 8, 9, 10, 12, 24, 36, 48 or 72 hours, or within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to the at least one drug of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least one primary amine group of the chemical spacer or at least one secondary amine group of the chemical spacer is attached to a carbon chain. In some alternatives, the spacer comprises isobutylamine. In some alternatives, the carbon chain can have at least or equal to 1, 5, 10, 15, 20, 25 or 30 carbon atoms or any number of carbon atoms within a range defined by any two of the aforementioned values. In some alternatives, the carbon chain has substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. Accordingly, some alternatives comprise the hydrogel prodrug manufactured by any of the approaches above and some alternatives comprise the hydrogel prodrug obtainable from said methods and some embodiments comprise any one or more of the hydrogel prodrugs as described above. In some alternatives of the hydrogel prodrug delivery system, the hydrogel prodrug comprises a peptide. In some alternatives of the hydrogel prodrug delivery system, the hydrogel prodrug comprises at least one drug. In some alternatives of the hydrogel prodrug delivery system, the at least one drug comprises a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the hydrogel prodrug delivery system, the hydrogel prodrug comprises a second, third, fourth, fifth, sixth, seventh, eighth, ninth or tenth drug. In some alternatives of the hydrogel prodrug delivery system, the second, third, fourth, fifth, sixth, seventh, eighth, ninth or tenth drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives of the hydrogel prodrug delivery system, the hydrogel prodrug comprises at least one acrylate. In some alternatives of the hydrogel prodrug delivery system, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives of the hydrogel prodrug delivery system, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives of the hydrogel prodrug delivery system, the cyclic carbon chains comprise saturated bonds, unsaturated bonds and/or heteroatoms. In some alternatives of the hydrogel prodrug delivery system, the acrylate comprises at least two acrylate groups and is a diacrylate. In some alternatives of the hydrogel prodrug delivery system, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives of the hydrogel prodrug delivery system, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives of the hydrogel prodrug delivery system, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second, third, fourth, fifth, sixth, seventh, eighth, ninth or tenth drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives of the hydrogel prodrug delivery system, the hydrogel prodrug further comprises a spacer. In some alternatives, the spacer comprises isobutylamine. In some alternatives of the hydrogel prodrug delivery system, the spacer comprises a hydrophilic group, such as a hydroxyl group. In some alternatives of the hydrogel prodrug delivery system, the spacer comprises a carbon chain. In some alternatives of the hydrogel prodrug delivery system, the carbon chain comprises at least or equal to 1, 5, 10, 15, 20, 25 or 30 carbon atoms or any number of carbon atoms within a range defined by any two of the aforementioned values. In some alternatives of the hydrogel prodrug delivery system, the carbon chain comprises substituted heterocarbons, unsubstituted heterocarbons, saturated carbon bonds, unsaturated carbon bonds, branched cyclic carbon chains and/or unbranched cyclic carbon chains. In some alternatives of the hydrogel prodrug delivery system, the branched or unbranched cyclic carbon chains are saturated. In some alternatives of the hydrogel prodrug delivery system, the branched or unbranched cyclic carbon chains are unsaturated. In some alternatives of the hydrogel prodrug delivery system, the branched or unbranched cyclic carbon chains comprise heteroatoms. In some alternatives of the hydrogel prodrug delivery system, the hydrogel prodrug is a compressed sheet, film, incorporated into a scaffold, support or a dressing. In some alternatives of the hydrogel prodrug delivery system, the hydrogel prodrug is shaped into a tablet, an implantable device, microparticle or a pill. In some alternatives of the hydrogel prodrug delivery system, the hydrogel prodrug comprises a polymer structure, wherein, the polymer structure is a poly (beta amino ester) (PBAE). In some alternatives of the hydrogel prodrug delivery system, the hydrogel prodrug comprises a polymer structure, wherein, the primary amine of the drug is incorporated into the polymer structure by conjugate addition to a vinyl group of the at least one acrylate molecules, resulting in a tertiary amine within the polymer backbone, or wherein, two secondary amines of a drug molecule are each incorporated into the polymer structure by conjugate addition to the vinyl group of an acrylate molecule, resulting in two tertiary amines incorporated into the polymer backbone. In some alternatives of the hydrogel prodrug delivery system, the polymer structure terminates with acrylate ends. In some alternatives of the hydrogel prodrug delivery system, the drug is incorporated into the polymer structure and wherein, the drug is covalently linked between two acrylates. In some alternatives of the hydrogel prodrug delivery system, the spacer is in between every 1, 2, 3, 4, 5, 6, 7, 8, 9, 10, 15, 20, 50, or 100 acrylates of the polymer structure, or any integer within a range defined by any two of the aforementioned integers. In some alternatives of the hydrogel prodrug delivery system, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives of the hydrogel prodrug delivery system, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives of the hydrogel prodrug delivery system, the hydrogel prodrug comprises a degradation time to release drugs for a period of at least or equal to 1 month, 2 months, 4 months, 8 months, 12 months, or any amount of time within a range defined by any two aforementioned values. In some alternatives of the hydrogel prodrug delivery system, the hydrogel prodrug comprises a targeting moiety. In some alternatives of the hydrogel prodrug delivery system, the targeting moiety is specific for a ligand on an organ, tissue or a cell. In some alternatives of the hydrogel prodrug delivery system, the targeting moiety is specific for a surface protein that is expressed during manifestation of a disease. In some alternatives of the hydrogel prodrug delivery system, the disease is cancer, cardiac disease, a neurological disease or a skin disease. In some alternatives of the hydrogel prodrug delivery system, the targeting moiety is specific for a tumor cell ligand on a tumor or a cancer antigen. In some alternatives of the hydrogel prodrug delivery system, the tumor is a solid tumor. Accordingly, some alternatives comprise the hydrogel prodrug manufactured by any of the approaches above and some alternatives comprise the hydrogel prodrug obtainable from said methods and some embodiments comprise any one or more of the hydrogel prodrugs as described above.

In a third aspect, a method of making a hydrogel prodrug composition, in which the hydrogel prodrug composition has at least two drugs is provided. The method of making a hydrogel prodrug composition comprising at least two drugs can have the following: providing a first polymer prodrug manufactured by anyone of the alternatives provided herein, providing a second polymer prodrug manufactured by anyone of the alternatives provided herein, blending the first and second polymer prodrugs to form a mixture and cross-linking the first and second polymer prodrugs thereby forming a hydrogel prodrug composition comprising at least two drugs. The first and second polymer prodrugs can be manufactured by the following steps: providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is drug comprises at least a two secondary amine groups. In some alternatives, wherein the at least one amine group comprises at least two secondary amine groups. In some alternatives, the method comprises reacting the at least one acrylate with the at least two secondary amine groups of the at least one drug In some alternatives, at least one primary amine and/or at least one secondary amine are provided. In some alternatives, the at least one acrylate can have at least one acrylate group. In some alternatives, the at least one acrylate group is bound by an ester linkage to an opposing termini of a carbon chain. In some alternatives, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of 170, 250, 575, 700, 1000, 2000, 3500, 5000, 10000 g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of at least or equal to 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration that is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the method further comprises providing a second drug, wherein, the second drug comprises at least one amine group. In some alternatives, the second drug comprises at least two additional secondary amine groups one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the reacting step is performed for at least or equal to 1, 2, 3, 4, 5, 6, 7, 8, 9, 10, 12, 24, 36, 48 or 72 hours, or within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to the at least one drug of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least one primary amine group of the chemical spacer or at least one secondary amine group of the chemical spacer is attached to a carbon chain. In some alternatives, the spacer comprises isobutylamine. In some alternatives, the carbon chain can have at least or equal to 1, 5, 10, 15, 20, 25 or 30 carbon atoms or any number of carbon atoms within a range defined by any two of the aforementioned values. In some alternatives, the carbon chain has substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. Accordingly, some alternatives comprise the hydrogel prodrug manufactured by any of the approaches above and some alternatives comprise the hydrogel prodrug obtainable from said methods and some embodiments comprise any one or more of the hydrogel prodrugs as described above. In some alternatives, the first or second polymer prodrug comprises a peptide. In some alternatives, the first or second polymer prodrug comprises at least one drug. In some alternatives, the at least one drug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the first or second polymer prodrug comprises a second, third, fourth, fifth, sixth, seventh, eighth, ninth or tenth drug. In some alternatives, the second, third, fourth, fifth, sixth, seventh, eighth, ninth or tenth drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the first or second polymer prodrug comprises at least one acrylate. In some alternatives, the at least one acrylate is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second, third, fourth, fifth, sixth, seventh, eighth, ninth or tenth drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the first or second polymer prodrug further comprises a spacer group. In some alternatives, the spacer comprises at least primary amine group or at least one secondary amine group of the chemical spacer is attached to a carbon chain. In some alternatives, the carbon chain comprises at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the first or second polymer prodrug comprises a polymer structure, wherein, the polymer structure is a poly (beta amino ester) (PBAE). In some alternatives, the first or second polymer prodrug comprises a polymer structure, wherein, the drug is incorporated into the polymer structure. In some alternatives, the polymer structure terminates with acrylate ends. In some alternatives, the drug is incorporated into the polymer structure, wherein, the drug is covalently linked between two acrylates. In some alternatives, the spacer is in between every 1, 2, 3, 4, 5, 6, 7, 8, 9, 10 15, 20, 50, or 100 acrylates of the polymer structure, or any integer within a range defined by any two of the aforementioned values. In some alternatives, the method further comprises providing a third, fourth, fifth, sixth, seventh, eighth, ninth or tenth polymer prodrug and blending the third, fourth, fifth, sixth, seventh, eighth, ninth or tenth polymer prodrug with the first and second hydrogel prodrug during the blending step. In some alternatives of the method, the hydrogel prodrug composition comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives of the method, the hydrogel prodrug composition comprises a degradation time to release drugs for a period of at least or equal to 1 day, 2 days, 4 days, 8 days, 16 days, 32 days, 64 days or 128 days, or any number of days within a range defined by any two aforementioned values. In some alternatives of the method, the hydrogel prodrug composition comprises a degradation time to release drugs for a period of at least or equal to 1 month, 2 months, 4 months, 8 months, 12 months, or any amount of time within a range defined by any two aforementioned values. In some alternatives of the method, the first, second, third, fourth, fifth, sixth, seventh, eighth, ninth and/or tenth hydrogel prodrug further comprises providing a targeting moiety. In some alternatives of the method, the targeting moiety is specific for a ligand on an organ, tissue or a cell. In some alternatives of the method, the targeting moiety is specific for a surface protein that is expressed during manifestation of a disease. In some alternatives of the method, the disease is cancer, cardiac disease, a neurological disease or a skin disease. In some alternatives of the method, the targeting moiety is specific for a tumor cell ligand on a tumor or a cancer antigen. In some alternatives of the method, the tumor is a solid tumor. Accordingly, some alternatives comprise the hydrogel prodrug manufactured by any of the approaches above and some alternatives comprise the hydrogel prodrug obtainable from said methods and some embodiments comprise any one or more of the hydrogel prodrugs as described above.

In a fourth aspect, a hydrogel prodrug manufactured by any one of the alternative methods is provided. The method can include the following: providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is drug comprises at least a two secondary amine groups. In some alternatives, wherein the at least one amine group comprises at least two secondary amine groups. In some alternatives, the method comprises reacting the at least one acrylate with the at least two secondary amine groups of the at least one drug In some alternatives, at least one primary amine and/or at least one secondary amine are provided. In some alternatives, the at least one acrylate can have at least one acrylate group. In some alternatives, the at least one acrylate group is bound by an ester linkage to an opposing termini of a carbon chain. In some alternatives, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of 170, 250, 575, 700, 1000, 2000, 3500, 5000, 10000 g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of at least or equal to 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration that is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the method further comprises providing a second drug, wherein, the second drug comprises at least one amine group. In some alternatives, the second drug comprises at least two additional secondary amine groups one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesics, antiepileptic, antiviral, anti-erectile dysfunction drug, anti-arthritic drug, contraceptive, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the reacting step is performed for at least or equal to 1, 2, 3, 4, 5, 6, 7, 8, 9, 10, 12, 24, 36, 48 or 72 hours, or within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to the at least one drug of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least one primary amine group of the chemical spacer or at least one secondary amine group of the chemical spacer is attached to a carbon chain. In some alternatives, the spacer comprises isobutylamine. In some alternatives, the carbon chain can have at least or equal to 1, 5, 10, 15, 20, 25 or 30 carbon atoms or any number of carbon atoms within a range defined by any two of the aforementioned values. In some alternatives, the carbon chain has substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. Accordingly, some alternatives comprise the hydrogel prodrug manufactured by any of the approaches above and some alternatives comprise the hydrogel prodrug obtainable from said methods and some embodiments comprise any one or more of the hydrogel prodrugs as described above.

In a fifth aspect, a hydrogel prodrug composition manufactured by any one of the alternative methods described herein is provided. The method for making the hydrogel prodrug composition can have the following steps: providing a first polymer prodrug manufactured by anyone of the alternatives provided herein, providing a second polymer prodrug manufactured by anyone of the alternatives provided herein, blending the first and second polymer prodrugs to form a mixture and cross-linking the first and second polymer prodrugs thereby forming a hydrogel prodrug composition comprising at least two drugs. The first and second polymer prodrugs can be manufactured by the following steps: providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is drug comprises at least a two secondary amine groups. In some alternatives, wherein the at least one amine group comprises at least two secondary amine groups. In some alternatives, the method comprises reacting the at least one acrylate with the at least two secondary amine groups of the at least one drug In some alternatives, at least one primary amine and/or at least one secondary amine are provided. In some alternatives, the at least one acrylate can have at least one acrylate group. In some alternatives, the at least one acrylate group is bound by an ester linkage to an opposing termini of a carbon chain. In some alternatives, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000 g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration that is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the method further comprises providing a second drug, wherein, the second drug comprises at least one amine group. In some alternatives, the second drug comprises at least two additional secondary amine groups one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the reacting step is performed for at least 1, 2, 3, 4, 5, 6, 7, 8, 9, 10, 12, 24, 36, 48 or 72 hours, or within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to the at least one drug of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least one primary amine group of the chemical spacer or at least one secondary amine group of the chemical spacer is attached to a carbon chain. In some alternatives, the spacer comprises isobutylamine. In some alternatives, the carbon chain can have at least or equal to 1, 5, 10, 15, 20, 25 or 30 carbon atoms or any number of carbon atoms within a range defined by any two of the aforementioned values. In some alternatives, the carbon chain has substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. Accordingly, some alternatives comprise the hydrogel prodrug manufactured by any of the approaches above and some alternatives comprise the hydrogel prodrug obtainable from said methods and some embodiments comprise any one or more of the hydrogel prodrugs as described above.

In a sixth aspect, a method of ameliorating or inhibiting cancer, HIV, a viral infection, pain, a bacterial infection, a neurological disorder, hemorrhaging, multiple sclerosis, diabetes, high blood pressure, Alzheimer's, or inhibiting a fungal growth in a subject in need is provided. The method of making the hydrogel prodrug can have the following steps: delivering the hydrogel prodrug manufactured by any one of the alternatives described herein, the hydrogel prodrug system of any one of the alternatives described herein, the hydrogel prodrug composition manufactured by any one of the alternatives described herein, the hydrogel prodrug of any one of the alternatives described herein or the hydrogel prodrug composition of any one of the alternatives described herein. The method can include the following: providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is drug comprises at least a two secondary amine groups. In some alternatives, wherein the at least one amine group comprises at least two secondary amine groups. In some alternatives, the method comprises reacting the at least one acrylate with the at least two secondary amine groups of the at least one drug. In some alternatives, at least one primary amine and/or at least one secondary amine are provided. In some alternatives, the at least one acrylate can have at least one acrylate group. In some alternatives, the at least one acrylate group is bound by an ester linkage to an opposing termini of a carbon chain. In some alternatives, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000 g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of at least or equal to 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration that is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the method further comprises providing a second drug, wherein, the second drug comprises at least one amine group. In some alternatives, the second drug comprises at least two additional secondary amine groups one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the protein is insulin or lysozyme. In some alternatives, the reacting step is performed for at least or equal to 1, 2, 3, 4, 5, 6, 7, 8, 9, 10, 12, 24, 36, 48 or 72 hours, or within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to the at least one drug of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least one primary amine group of the chemical spacer or at least one secondary amine group of the chemical spacer is attached to a carbon chain. In some alternatives, the spacer comprises isobutylamine. In some alternatives, the carbon chain can have at least or equal to 1, 5, 10, 15, 20, 25 or 30 carbon atoms or any number of carbon atoms within a range defined by any two of the aforementioned values. In some alternatives, the carbon chain has substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. The hydrogel prodrug delivery system can comprise the hydrogel prodrug manufactured by any one of alternatives described herein. In some alternatives of the hydrogel prodrug delivery system, the hydrogel prodrug comprises a peptide. In some alternatives of the hydrogel prodrug delivery system, the hydrogel prodrug comprises at least one drug. In some alternatives of the hydrogel prodrug delivery system, the at least one drug comprises a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the hydrogel prodrug delivery system, the hydrogel prodrug comprises a second, third, fourth, fifth, sixth, seventh, eighth, ninth or tenth drug. In some alternatives of the hydrogel prodrug delivery system, the second, third, fourth, fifth, sixth, seventh, eighth, ninth or tenth drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the hydrogel prodrug delivery system, the hydrogel prodrug comprises at least one acrylate. In some alternatives of the hydrogel prodrug delivery system, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives of the hydrogel prodrug delivery system, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives of the hydrogel prodrug delivery system, the cyclic carbon chains comprise saturated bonds, unsaturated bonds and/or heteroatoms. In some alternatives of the hydrogel prodrug delivery system, the acrylate comprises at least two acrylate groups and is a diacrylate. In some alternatives of the hydrogel prodrug delivery system, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives of the hydrogel prodrug delivery system, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives of the hydrogel prodrug delivery system, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second, third, fourth, fifth, sixth, seventh, eighth, ninth or tenth drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives of the hydrogel prodrug delivery system, the hydrogel prodrug further comprises a spacer. In some alternatives, the spacer comprises isobutylamine. In some alternatives of the hydrogel prodrug delivery system, the spacer comprises a hydrophilic group, such as a hydroxyl group. In some alternatives of the hydrogel prodrug delivery system, the spacer comprises a carbon chain. In some alternatives of the hydrogel prodrug delivery system, the carbon chain comprises at least or equal to 1, 5, 10, 15, 20, 25 or 30 carbon atoms or any number of carbon atoms within a range defined by any two of the aforementioned values. In some alternatives of the hydrogel prodrug delivery system, the carbon chain comprises substituted heterocarbons, unsubstituted heterocarbons, saturated carbon bonds, unsaturated carbon bonds, branched cyclic carbon chains and/or unbranched cyclic carbon chains. In some alternatives of the hydrogel prodrug delivery system, the branched or unbranched cyclic carbon chains are saturated. In some alternatives of the hydrogel prodrug delivery system, the branched or unbranched cyclic carbon chains are unsaturated. In some alternatives of the hydrogel prodrug delivery system, the branched or unbranched cyclic carbon chains comprise heteroatoms. In some alternatives of the hydrogel prodrug delivery system, the hydrogel prodrug is a compressed sheet, film, incorporated into a scaffold, support or a dressing. In some alternatives of the hydrogel prodrug delivery system, the hydrogel prodrug is shaped into a tablet, an implantable device, microparticle or a pill. In some alternatives of the hydrogel prodrug delivery system, the hydrogel prodrug comprises a polymer structure, wherein, the polymer structure is a poly (beta amino ester) (PBAE). In some alternatives of the hydrogel prodrug delivery system, the hydrogel prodrug comprises a polymer structure, wherein, the primary amine of the drug is incorporated into the polymer structure by conjugate addition to a vinyl group of the at least one acrylate molecules, resulting in a tertiary amine within the polymer backbone, or wherein, two secondary amines of a drug molecule are each incorporated into the polymer structure by conjugate addition to the vinyl group of an acrylate molecule, resulting in two tertiary amines incorporated into the polymer backbone. In some alternatives of the hydrogel prodrug delivery system, the polymer structure terminates with acrylate ends. In some alternatives of the hydrogel prodrug delivery system, the drug is incorporated into the polymer structure and wherein, the drug is covalently linked between two acrylates. In some alternatives of the hydrogel prodrug delivery system, the spacer is in between every 1, 2, 3, 4, 5, 6, 7, 8, 9, 10, 15, 20, 50, or 100 acrylates of the polymer structure, or any integer within a range defined by any two of the aforementioned integers. In some alternatives of the hydrogel prodrug delivery system, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives of the hydrogel prodrug delivery system, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives of the hydrogel prodrug delivery system, the hydrogel prodrug comprises a degradation time to release drugs for a period of at least or equal to 1 month, 2 months, 4 months, 8 months, 12 months, or any amount of time within a range defined by any two aforementioned values. In some alternatives of the hydrogel prodrug delivery system, the hydrogel prodrug comprises a targeting moiety. In some alternatives of the hydrogel prodrug delivery system, the targeting moiety is specific for a ligand on an organ, tissue or a cell. In some alternatives of the hydrogel prodrug delivery system, the targeting moiety is specific for a surface protein that is expressed during manifestation of a disease. In some alternatives of the hydrogel prodrug delivery system, the disease is cancer, cardiac disease, a neurological disease or a skin disease. In some alternatives of the hydrogel prodrug delivery system, the targeting moiety is specific for a tumor cell ligand on a tumor or a cancer antigen. In some alternatives of the hydrogel prodrug delivery system, the tumor is a solid tumor. In some alternatives, the hydrogel prodrug composition comprises providing a first polymer prodrug manufactured by anyone of the alternatives provided herein, providing a second polymer prodrug manufactured by anyone of the alternatives provided herein, blending the first and second polymer prodrugs to form a mixture and cross-linking the first and second polymer prodrugs thereby forming a hydrogel prodrug composition comprising at least two drugs. In some alternatives, the method of making the composition further comprises providing a third, fourth, fifth, sixth, seventh, eighth, ninth or tenth hydrogel prodrug and blending the third, fourth, fifth, sixth, seventh, eighth, ninth or tenth hydrogel prodrug with the first and second hydrogel prodrug during the blending step. In some alternatives, the hydrogel prodrug composition comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug composition comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug composition comprises the hydrogel prodrug composition comprises a degradation time to release drugs for a period of at least or equal to 1 month, 2 months, 4 months, 8 months, 12 months, or any amount of time within a range defined by any two aforementioned values. In some alternatives, the hydrogel prodrug composition comprises the first, second, third, fourth, fifth, sixth, seventh, eighth, ninth and/or tenth hydrogel prodrug further comprises providing a targeting moiety. In some alternatives, the hydrogel prodrug composition comprises the targeting moiety is specific for a ligand on an organ, tissue or a cell. In some alternatives, the hydrogel prodrug composition comprises the targeting moiety is specific for a surface protein that is expressed during manifestation of a disease. In some alternatives, the hydrogel prodrug composition comprises the disease is cancer, cardiac disease, a neurological disease or a skin disease. In some alternatives, the hydrogel prodrug composition comprises the targeting moiety is specific for a tumor cell ligand on a tumor or a cancer antigen. In some alternatives, the hydrogel prodrug composition comprises the tumor is a solid tumor. the hydrogel prodrug or the hydrogel prodrug composition comprises a nucleic acid analogue, amino ester-based drug, neurokinin agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives, the hydrogel prodrug or the hydrogel prodrug composition comprises acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the protein is insulin or lysozyme. In some alternatives, the hydrogel prodrug or the hydrogel prodrug composition is a compressed sheet, or incorporated into a scaffold, support or dressing. In some alternatives, the hydrogel prodrug or the hydrogel prodrug composition is shaped into a capsule, a tablet, microparticle or an implantable device. In some alternatives, the hydrogel prodrug or the hydrogel prodrug composition is delivered by applying the compressed sheet directly to a skin surface. In some alternatives, the hydrogel prodrug or the hydrogel prodrug composition is applied directly over a wound. In some alternatives, the hydrogel prodrug or the hydrogel prodrug composition is an implantable device, and wherein, the implantable device is placed subcutaneously at a site of a tumor to provide sustained chemotherapeutic release. In some alternatives, the hydrogel prodrug or the hydrogel prodrug composition is a microparticle, and wherein, the microparticle is injected into a tissue. Accordingly, some alternatives comprise the hydrogel prodrug manufactured by any of the approaches above and some alternatives comprise the hydrogel prodrug obtainable from said methods and some embodiments comprise any one or more of the hydrogel prodrugs as described above.

In a seventh aspect, a method of making a hydrogel prodrug, wherein the hydrogel prodrug is configured to degrade via hydrolysis and releasing at least one drug that is in a native, unaltered form of the drug is provided. The method comprises: a) providing at least one molecule that comprises at least one amine group (A); b) providing at least one diacrylate (D); c) reacting said at least one diacrylate with said at least one amine group of the at least one molecule, thereby producing at least one non-drug-containing poly (beta amino ester) (PBAE); d) providing a linear molecule (M), wherein the linear molecule (M) is terminated at one end with a carboxylic acid and terminated at the other end with a group reactive to the poly(beta amino ester); e) reacting the poly (beta amino ester) (PBAE) with the linear molecule (M) to form a carboxylic acid terminated polymer chain, wherein the carboxylic acid terminated polymer chain comprises a structure $[M-D-[A-D]_n-M]_m$ or $[M-A-[D-A]_n-M]_m$; f) providing a drug (X), wherein the drug comprises at least two hydroxyl groups; g) reacting the drug (X) with the carboxylic acid terminated polymer chain formed in step e), wherein the carboxylic acid terminated polymer chain is in a molar excess over the drug; thereby producing a copolymer comprising structure comprising: $[M-D-[A-D]_n-M-X]_m-M$, wherein the structure comprises at least one or more reactive terminal groups and ester bonds are formed; and optionally h) performing a cross linking reaction between the polymer produced in step g) with a molecule comprising 3 or more reactive hydroxyl groups or any other molecule with three or more groups capable of reacting with the at least one or more reactive terminal groups of the polymer produced in step g). the reacting of step g) or the cross linking reaction of step h) produces a copolymer comprising a drug ester of the drug in step f) and the at least one non-drug-containing poly (beta amino ester) (PBAE) connected by the linear molecule of step d), and wherein the copolymer comprises ester linkages. In some alternatives, the copolymer is cross linked into a hydrogel, wherein the hydrogel is capable of degrading at the ester linkages to release native drug. In some alternatives, the group reactive to the at least one non-drug-containing poly (beta amino ester) (PBAE) of the linear molecule comprises an amine, acrylate or methacrylate. In some alternatives, the at least one non-drug-containing poly (beta amino ester) (PBAE) terminates with a diacrylate and wherein the diacrylate reacts with the amine of the linear molecule or wherein the group reactive to the at least one non-drug-containing poly (beta amino ester) (PBAE) of the linear molecule comprises an acrylate or methacrylate and wherein the at least one non-drug-containing poly (beta amino ester) (PBAE) terminates with an amine, wherein the amine reacts with the acrylate or methacrylate of the linear molecule. In some alternatives, the diacrylate is in a molar excess over the at least one molecule that comprises the at least one amine group in step a) or wherein the at least one amine group in step a) is in a molar excess over the at least at least one diacrylate (D). In some alternatives, structure of the at least one non-drug-containing poly (beta amino ester) (PBAE) is D-[A-D]n or is A-[D-A]n. In some alternatives, the linear molecule is PEG. In some alternatives, the at least one amine group is a free primary amine group, a secondary amine group or comprises at least two secondary amine groups. In some alternatives, the drug (X) comprises 3 or more hydroxyl groups, and wherein the only steps a)-f) are performed. In some alternatives, the at least one drug (X) is a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psycho stimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir.

In an eighth aspect, a method of making a hydrogel prodrug, wherein the hydrogel prodrug is configured to degrade via hydrolysis and releasing at least one drug that is in a native, unaltered form of the drug is provided. The method comprises: a) providing at least one biodegradable polymer, wherein the at least one biodegradable polymer terminates with at least one acrylate or at least one amine; b) providing a linear molecule (M), wherein the linear molecule (M) is terminated at one end with a carboxylic acid and terminated at the other end with a group reactive to the at least one acrylate or the at least one amine of the biodegradable polymer; c) reacting the at least one acrylate or the at least one amine of the biodegradable polymer with the linear molecule (M) to form a carboxylic acid terminated polymer chain, wherein the carboxylic acid terminated polymer chain comprises a structure [M-D-[A-D]n-M]m or [M-A-[D-A]n-M]m; d) providing at least one drug (X), wherein the drug comprises at least two hydroxyl groups; e) reacting the at least one drug (X) with the carboxylic acid terminated polymer chain formed in step c), wherein the carboxylic acid terminated polymer chain is in a molar excess over the at least one drug (X); thereby producing a structure comprising: [M-D-[A-D]n-M-X]m-M, wherein the structure comprises at least one or more reactive terminal groups; and optionally f) performing a cross linking reaction between the polymer produced in step e) with a molecule comprising 3 or more reactive hydroxyl groups or any other molecule with three or more groups capable of reacting with the at least one or more reactive terminal groups of the polymer produced in step e). In some alternatives, the reacting of step e) or the cross linking reaction of step f) produces a copolymer comprising a drug ester of the drug in step d) and the at least one non-drug-containing poly (beta amino ester) (PBAE) connected by the linear molecule of step b), and wherein the copolymer comprises ester linkages. In some alternatives, the copolymer is cross linked into a hydrogel, wherein the hydrogel is capable of degrading at the ester linkages to release native drug.

In a ninth aspect, a hydrogel prodrug delivery system is provided, wherein the hydrogel prodrug delivery system comprises the hydrogel prodrug manufactured by any one of the alternatives provided herein. In some alternatives, in the method of making a hydrogel prodrug, the hydrogel prodrug is capable of biodegrading or is configured to degrade via hydrolysis and releasing at least one drug that is in a native, unaltered form of the drug is provided. The method of making the hydrogel prodrug comprises: a) providing at least one molecule that comprises at least one amine group (A); b) providing at least one diacrylate (D); c) reacting said at least one diacrylate with said at least one amine group of the at least one molecule, thereby producing at least one non-drug-containing poly (beta amino ester) (PBAE); d) providing a linear molecule (M), wherein the linear molecule (M) is terminated at one end with a carboxylic acid and terminated at the other end with a group reactive to the poly(beta amino ester); e) reacting the poly (beta amino ester) (PBAE) with the linear molecule (M) to form a carboxylic acid terminated polymer chain, wherein the carboxylic acid terminated polymer chain comprises a structure [M-D-[A-D]n-M]m or [M-A-[D-A]n-M]m; f) providing a drug (X), wherein the drug comprises at least two hydroxyl groups; g) reacting the drug (X) with the carboxylic acid terminated polymer chain formed in step e), wherein the carboxylic acid terminated polymer chain is in a molar excess over the drug; thereby producing a copolymer comprising structure comprising: [M-D-[A-D]n-M-X]m-M, wherein the structure comprises at least one or more reactive terminal groups and ester bonds are formed; and optionally h) performing a cross linking reaction between the polymer produced in step g) with a molecule comprising 3 or more reactive hydroxyl groups or any other molecule with three or more groups capable of reacting with the at least one or more reactive terminal groups of the polymer produced in step g). the reacting of step g) or the cross linking reaction of step h) produces a copolymer comprising a drug ester of the drug in step f) and the at least one non-drug-containing poly (beta amino ester) (PBAE) connected by the linear molecule of step d), and wherein the copolymer comprises ester linkages. In some alternatives, the copolymer is cross linked into a hydrogel, wherein the hydrogel is capable of degrading at the ester linkages to release native drug. In some alternatives, the group reactive to the at least one non-drug-containing poly (beta amino ester) (PBAE) of the linear molecule comprises an amine, acrylate or methacrylate. In some alternatives, the at least one non-drug-containing poly (beta amino ester) (PBAE) terminates with a diacrylate and wherein the diacrylate reacts with the amine of the linear molecule or wherein the group reactive to the at least one non-drug-containing poly (beta amino ester) (PBAE) of the linear molecule comprises an acrylate or methacrylate and wherein the at least one non-drug-containing poly (beta amino ester) (PBAE) terminates with an amine, wherein the amine reacts with the acrylate or methacrylate of the linear molecule. In some alternatives, the diacrylate is in a molar excess over the at least one molecule that comprises the at least one amine group in step a) or wherein the at least one amine group in step a) is in a molar excess over the at least one diacrylate (D). In some alternatives, structure of the at least one non-drug-containing poly (beta amino ester) (PBAE) is D-[A-D]n or is A-[D-A]n. In some alternatives, the linear molecule is PEG. In some alternatives, the at least one amine group is a free primary amine group, a secondary amine group or comprises at least two secondary amine groups. In some alternatives, the drug (X) comprises 3 or more hydroxyl groups, and wherein the only steps a)-f) are performed. In some alternatives, the at least one drug (X) is a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psycho stimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir.

In a tenth aspect, a hydrogel prodrug delivery system is provided, wherein the hydrogel prodrug delivery system comprises the hydrogel prodrug manufactured by anyone of the alternative methods described herein. In some alternatives of the method of making a hydrogel prodrug, the hydrogel prodrug is capable of biodegrading or is configured to degrade via hydrolysis and releasing at least one drug that is in a native, unaltered form of the drug is provided. The method of making the hydrogel prodrug comprises: a) providing at least one biodegradable polymer, wherein the at least one biodegradable polymer terminates with at least one acrylate or at least one amine; b) providing a linear molecule (M), wherein the linear molecule (M) is terminated at one end with a carboxylic acid and terminated at the other end with a group reactive to the at least one acrylate or the at least one amine of the biodegradable polymer; c) reacting the at least one acrylate or the at least one amine of the biodegradable polymer with the linear molecule (M) to form a carboxylic acid terminated polymer chain, wherein the carboxylic acid terminated polymer chain comprises a structure [M-D-[A-D]n-M]m or [M-A-[D-A]n-M]m; d) providing at least one drug (X), wherein the drug comprises at least two hydroxyl groups; e) reacting the at least one drug (X) with the carboxylic acid terminated polymer chain formed in step c), wherein the carboxylic acid terminated polymer chain is in a molar excess over the at least one drug (X); thereby producing a structure comprising: [M-D-[A-D]n-M-X]m-M, wherein the structure comprises at least one or more reactive terminal groups; and optionally f) performing a cross linking reaction between the polymer produced in step e) with a molecule comprising 3 or more reactive hydroxyl groups or any other molecule with three or more groups capable of reacting with the at least one or more reactive terminal groups of the polymer produced in step e). In some alternatives, the reacting of step e) or the cross linking reaction of step f) produces a copolymer comprising a drug ester of the drug in step d) and the at least one non-drug-containing poly (beta amino ester) (PBAE) connected by the linear molecule of step b), and wherein the copolymer comprises ester linkages. In some alternatives, the copolymer is cross linked into a hydrogel, wherein the hydrogel is capable of degrading at the ester linkages to release native drug.

In an eleventh aspect, a hydrogel prodrug delivery system is provided, wherein the hydrogel prodrug delivery system comprises a hydrogel prodrug, wherein the hydrogel prodrug comprises a copolymer, wherein the copolymer comprises a drug ester, a biodegradable polymer, wherein the drug ester and biodegradable polymer are non-covalently linked by a linear molecule. In some alternatives, the hydrogel prodrug is a compressed sheet, or incorporated into a scaffold, support, dressing or is shaped into a capsule, a tablet, microparticle or an implantable device. In some alternatives, the hydrogel prodrug comprises a least one drug (X). In some alternatives, the at least one drug (X) is a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psycho stimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir.

In a twelfth aspect, a method of inhibiting cancer, HIV, a viral infection, pain, a bacterial infection, a neurological disorder, hemorrhaging, multiple sclerosis, diabetes, high blood pressure, Alzheimer's, or inhibiting a fungal growth in a subject in need is provided. The method comprises providing the hydrogel prodrug delivery system of of any one of the alternatives herein to said subject in need. The hydrogel prodrug delivery system comprises the hydrogel prodrug manufactured by any one of the alternatives provided herein. In some alternatives, in the method of making a hydrogel prodrug, the hydrogel prodrug is capable of biodegrading or is configured to degrade via hydrolysis and releasing at least one drug that is in a native, unaltered form of the drug is provided. The method of making the hydrogel prodrug comprises: a) providing at least one molecule that comprises at least one amine group (A); b) providing at least one diacrylate (D); c) reacting said at least one diacrylate with said at least one amine group of the at least one molecule, thereby producing at least one non-drug-containing poly (beta amino ester) (PBAE); d) providing a linear molecule (M), wherein the linear molecule (M) is terminated at one end with a carboxylic acid and terminated at the other end with a group reactive to the poly(beta amino ester); e) reacting the poly (beta amino ester) (PBAE) with the linear molecule (M) to form a carboxylic acid terminated polymer chain, wherein the carboxylic acid terminated polymer chain comprises a structure [M-D-[A-D]n-M]m or [M-A-[D-A]n-M]m; f) providing a drug (X), wherein the drug comprises at least two hydroxyl groups; g) reacting the drug (X) with the carboxylic acid terminated polymer chain formed in step e), wherein the carboxylic acid terminated polymer chain is in a molar excess over the drug; thereby producing a copolymer comprising structure comprising: [M-D-[A-D]n-M-X]m-M, wherein the structure comprises at least one or more reactive terminal groups and ester bonds are formed; and optionally h) performing a cross linking reaction between the polymer produced in step g) with a molecule comprising 3 or more reactive hydroxyl groups or any other molecule with three or more groups capable of reacting with the at least one or more reactive terminal groups of the polymer produced in step g). the reacting of step g) or the cross linking reaction of step h) produces a copolymer comprising a drug ester of the drug in step f) and the at least one non-drug-containing poly (beta amino ester) (PBAE) connected by the linear molecule of step d), and wherein the copolymer comprises ester linkages. In some alternatives, the copolymer is cross linked into a hydrogel, wherein the hydrogel is capable of degrading at the ester linkages to release native drug. In some alternatives, the group reactive to the at least one non-drug-containing poly (beta amino ester) (PBAE) of the linear molecule comprises an amine, acrylate or methacrylate. In some alternatives, the at least one non-drug-containing poly (beta amino ester) (PBAE) terminates with a diacrylate and wherein the diacrylate reacts with the amine of the linear molecule or wherein the group reactive to the at least one non-drug-containing poly (beta amino ester) (PBAE) of the linear molecule comprises an acrylate or methacrylate and wherein the at least one non-drug-containing poly (beta amino ester) (PBAE) terminates with an amine, wherein the amine reacts with the acrylate or methacrylate of the linear molecule. In some alternatives, the diacrylate is in a molar excess over the at least one molecule that comprises the at least one amine group in step a) or wherein the at least one amine group in step a) is in a molar excess over the at least one diacrylate (D). In some alternatives, structure of the at least one non-drug-containing poly (beta amino ester) (PBAE) is D-[A-D]n or is A-[D-A]n. In some alternatives, the linear molecule is PEG. In some alternatives, the at least one amine group is a free primary amine group, a secondary amine group or comprises at least two secondary amine groups. In some alternatives, the drug (X) comprises 3 or more hydroxyl groups, and wherein the only the steps a)-f) are performed. In some alternatives, the at least one drug (X) is a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir. In some alternatives of the method of making a hydrogel prodrug, the hydrogel prodrug is capable of biodegrading or is configured to degrade via hydrolysis and releasing at least one drug that is in a native, unaltered form of the drug is provided. The method of making the hydrogel prodrug comprises: a) providing at least one biodegradable polymer, wherein the at least one biodegradable polymer terminates with at least one acrylate or at least one amine; b) providing a linear molecule (M), wherein the linear molecule (M) is terminated at one end with a carboxylic acid and terminated at the other end with a group reactive to the at least one acrylate or the at least one amine of the biodegradable polymer; c) reacting the at least one acrylate or the at least one amine of the biodegradable polymer with the linear molecule (M) to form a carboxylic acid terminated polymer chain, wherein the carboxylic acid terminated polymer chain comprises a structure [M-D-[A-D]n-M]m or [M-A-[D-A]n-M]m; d) providing at least one drug (X), wherein the drug comprises at least two hydroxyl groups; e) reacting the at least one drug (X) with the carboxylic acid terminated polymer chain formed in step c), wherein the carboxylic acid terminated polymer chain is in a molar excess over the at least one drug (X); thereby producing a structure comprising: [M-D-[A-D]n-M-X]m-M, wherein the structure comprises at least one or more reactive terminal groups; and optionally f) performing a cross linking reaction between the polymer produced in step e) with a molecule comprising 3 or more reactive hydroxyl groups or any other molecule with three or more groups capable of reacting with the at least one or more reactive terminal groups of the polymer produced in step e). In some alternatives, the reacting of step e) or the cross linking reaction of step f) produces a copolymer comprising a drug ester of the drug in step d) and the at least one non-drug-containing poly (beta amino ester) (PBAE) connected by the linear molecule of step b), and wherein the copolymer comprises ester linkages. In some alternatives, the copolymer is cross linked into a hydrogel, wherein the hydrogel is capable of degrading at the ester linkages to release native drug. In some alternatives, the hydrogel prodrug delivery system comprises a hydrogel prodrug, wherein the hydrogel prodrug comprises a copolymer, wherein the copolymer comprises a drug ester, a biodegradable polymer, wherein the drug ester and biodegradable polymer are non-covalently linked by a linear molecule. In some alternatives, the hydrogel prodrug is a compressed sheet, or incorporated into a scaffold, support, dressing or is shaped into a capsule, a tablet, microparticle or an implantable device. In some alternatives, the hydrogel prodrug comprises a least one drug (X). In some alternatives, the at least one drug (X) is a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psycho stimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir. In some alternatives, of the method of ameliorating, treating, or inhibiting cancer, HIV, a viral infection, pain, a bacterial infection, a neurological disorder, hemorrhaging, multiple sclerosis, diabetes, high blood pressure, Alzheimer's, or inhibiting a fungal growth in a subject in need, the hydrogel prodrug delivery system comprises a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir. In some alternatives, of the method of ameliorating, treating, or inhibiting cancer, HIV, a viral infection, pain, a bacterial infection, a neurological disorder, hemorrhaging, multiple sclerosis, diabetes, high blood pressure, Alzheimer's, or inhibiting a fungal growth in a subject in need, the hydrogel prodrug delivery system is provided to said subject by applying the compressed sheet directly to a skin surface. In some alternatives, of the method of ameliorating, treating, or inhibiting cancer, HIV, a viral infection, pain, a bacterial infection, a neurological disorder, hemorrhaging, multiple sclerosis, diabetes, high blood pressure, Alzheimer's, or inhibiting a fungal growth in a subject in need, the hydrogel prodrug is applied directly over a wound. In some alternatives, of the method of ameliorating, treating, or inhibiting cancer, HIV, a viral infection, pain, a bacterial infection, a neurological disorder, hemorrhaging, multiple sclerosis, diabetes, high blood pressure, Alzheimer's, or inhibiting a fungal growth in a subject in need, the hydrogel prodrug is an implantable device, and wherein, the implantable device is placed subcutaneously at a site of a tumor to provide a sustained chemotherapeutic release. In some alternatives, of the method of ameliorating, treating, or inhibiting cancer, HIV, a viral infection, pain, a bacterial infection, a neurological disorder, hemorrhaging, multiple sclerosis, diabetes, high blood pressure, Alzheimer's, or inhibiting a fungal growth in a subject in need, the hydrogel prodrug is a microparticle, and wherein, the microparticle is injected into a tissue.

BRIEF DESCRIPTION OF THE DRAWINGS

FIG. 10 A shows the wavelength scan of a drug free polymer and VS39 (tranexamic acid polymer). FIG. 10B shows the tranexamic acid polymer standard curve.

FIG. 11A shows the release kinetics for VS39, a hydrogel prodrug formulated to release tranexamic acid for four hours. FIG. 11B shows the release kinetics for VS45, a hydrogel prodrug formulated to release tranexamic acid for 20 hours.

FIG. 37 shows the absorbance spectrum of various insulin hydrogel prodrug batches after complete degradation in water.

DEFINITIONS

Figure 1:
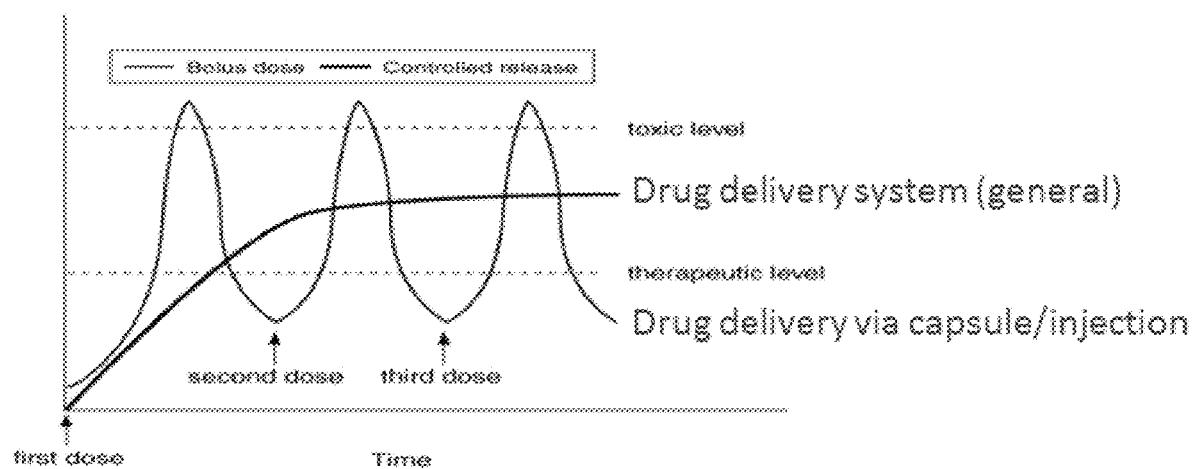
FIG. 1 shows the controlled release of a drug within a delivery system in comparison to a drug that is delivered by a tablet (pill, capsule) or an injection.

Unless defined otherwise, all technical and scientific terms used herein, have the same meaning as commonly understood by one of ordinary skill in the art to which the invention pertains.

"About" as used herein, when referring to a measurable value is meant to encompass variations of ±20% or ±10%, more preferably ±5%, even more preferably ±1%, and still more preferably ±0.1% from the specified value.

"Hydrogel prodrug," as used herein, refers to a network of polymer chains that can be hydrophilic and comprises therapeutics. The polymer chains are cross-linked and be composed of materials that can be degraded within a biological environment such as biodegradable polymers. Examples of polymers that can degrade within the body can include but are not limited to polyactides (PLA), polyglycolides (PGA), Poly (lactide-co-glycolides (PLGA), polyanhydrides and polyorthoesters. In the alternatives described herein, the hydrogel prodrug can comprise polymer prodrugs that are cross-linked to one another.

"Drug" as described herein, refers to chemical substances or formulations used in the treatment, cure, prevention, or diagnosis of disease or used to otherwise enhance physical or mental well-being. In the alternatives described herein, a drug is attached to a hydrogel prodrug for treatment. The drug can be a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the drug comprises a free primary amine or at least two secondary amine groups. In some alternatives, the drug comprises at least one primary amine, at least two secondary amines, or a combination of one or more primary amines and one or more secondary amines.

In some alternatives, the drug comprises nucleic acid analogues, tenofovir amino ester-based drugs, neurokinin 1 agonists, platinum-based amine-containing chemotherapeutics, anthracyclines, γ-aminobutyric acid-derived drugs, pregabalin, amino acid derivatives, aminated benzoic acid derivatives, or proteins of any size, such as insulin or lysozyme, or antibodies or binding fragments thereof, such as IgG or binding fragments thereof or hormone derivatives.

In some alternatives, the drug is a cancer therapeutic.

Without being limiting, the drug categories, which have been proven to be compatible with the hydrogel prodrug technology described herein include nucleic acid analogues such as the antiviral medications acyclovir, ganciclovir, or tenofovir; amino ester-based drugs, such as the anesthetics procaine or benzocaine; neurokinin 1 agonists such as the antiemetic aprepitant; platinum-based, amine-containing chemotherapeutics such as cisplatin or oxaliplatin; anthracyclines such as doxorubicin; γ-aminobutyric acid-derived drugs such as the seizure and pain medications gabapentin or pregabalin; amino acid derivatives, such as the synthetic lysine derivative anti-hemorrhage drug tranexamic acid; aminated benzoic acid derivatives, such as the anti-inflammatory aspirin derivative 5-aminosalicylic acid; proteins of any size, such as insulin or lysozyme, antibodies or binding fragments thereof, such as IgG or binding fragments thereof, or hormone derivatives, such as the synthetic thyroid hormone levothyroxine. In some alternatives of the hydrogel described herein, the drug is a nucleic acid analogue such as the antiviral medication acyclovir, or ganciclovir, or tenofovir amino ester-based drugs, such as the anesthetics procaine or benzocaine; neurokinin 1 agonists such as the antiemetic aprepitant; platinum-based, amine-containing chemotherapeutics such as cisplatin or oxaliplatin; anthracyclines such as doxorubicin; γ-aminobutyric acid-derived drugs such as the seizure and pain medications gabapentin or pregabalin; amino acid derivatives, such as the synthetic lysine derivative anti-hemorrhage drug tranexamic acid; aminated benzoic acid derivatives, such as the anti-inflammatory aspirin derivative 5-aminosalicylic acid; proteins of any size, such as insulin or lysozyme, antibodies or binding fragments thereof, such as IgG or binding fragments thereof or hormone derivatives, such as the synthetic thyroid hormone levothyroxine.

In some alternatives, the drugs for attachment to the hydrogel are from general drug families consisting of compounds containing a primary amine that are compatible with the hydrogel prodrug technology and may be delivered in a controlled manner using this technology. Without being limiting these drugs can include, antibiotics, amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines, pyrimidines, quinolones, fluoroquinolones, statins, steroids, sulfonamides, taxoides, tetracyclines, statins, chemotherapeutics, alkylating agents, platinum drugs, antimetabolites, cytotoxic antibiotics, topoisomerase inhibitors, mitotic inhibitors, corticosteroids, targeted enzyme inhibitors, antibody-drug conjugates, antibody fragments, protein fragments, oligopeptides, polypeptides, hormones, steroids, antipsychotics, anti-Alzheimer's drugs, cholesterol regulators, anesthetics, analgesics, antiepileptics, antivirals, anti-erectile dysfunction, antiarthritic drug, contraceptives, diabetes medication, enzyme inhibitors, psychostimulants or platelet aggregation inhibitors. In some of the alternatives of the hydrogel herein, the drug is doxorubicin, procaine, insulin or acyclovir.

In some alternatives of the hydrogel, the drug is an antibiotic. In some alternatives, the antibiotic is an amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones and fluoroquinolones, statins, steroids, sulfonamides, taxoides, or tetracyclines.

"Protein" as described herein, refers to a biomolecule or macromolecule made up of amino acid residues or a chain of peptides. A linear chain of amino acid residues is called a polypeptide. In some alternatives described herein, the hydrogel prodrug comprises a protein. In some alternatives, the protein comprises a free primary amine or at least two secondary amine groups to attach to the backbone of the hydrogel prodrug.

In some alternatives, the protein is insulin.

In some alternatives, the drug is aminated. Amination is the process by which an amine group is introduced into a molecule. This can be used to place any drug into any one of the alternative hydrogels described herein. Amination is a chemical reaction that can be appreciated by those skilled in the art.

"Acrylate" as described herein, refers to salts, esters and conjugate bases of acrylic acid and its derivatives. They can also be referred to as propionates (since acrylic acid is also known as 2-propenoic acid). The acrylate ion has the molecular formula CH2=CHCOO—. Acrylates comprise vinyl groups (a double bond), that is directly bound to a carbonyl carbon. Without being limiting, examples of monomeric acrylates can include methacrylates, methyl acrylate, ethyl acrylate, 2-Chloroethyl vinyl ether, 2-Ethylhexyl acrylate, hydroxyethyl methacrylate, butyl acrylate, butyl methacrylate and TMPTA. A diacrylate, as described herein, has two acrylate groups. Without being limiting, examples of diacrylates can include, for example, 1, 6 Hexanediol Diacrylate, polyethylene glycol diacrylate, polyethylene glycol 400 diacrylate, dipropylene glycol diacrylate, 1,6 hexanediol diacrylate, ethylene glycol diacrylate, poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) and diethylene glycol diacrylate (DEGDA). In some alternatives described herein, the acrylate used in manufacture of a polymer prodrug is methacrylates, methyl acrylate, ethyl acrylate, 2-Chloroethyl vinyl ether, 2-Ethylhexyl acrylate, hydroxyethyl methacrylate, butyl acrylate, butyl methacrylate and TMPTA. A diacrylate, as described herein, has two acrylate groups. Without being limiting, examples of diacrylates can include, for example, 1, 6 Hexanediol Diacrylate, polyethylene glycol diacrylate, polyethylene glycol 400 diacrylate, dipropylene glycol diacrylate, 1,6 hexanediol diacrylate, ethylene glycol diacrylate, poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the acrylate is biodegradable.

"Acrylate group" or acryloyl group is a form of an enone with the structure $H_2C=CH-C(=O)-$. It is an acyl group derived from acrylic acid. In some alternatives described herein, the acrylate comprises two acrylate groups and is therefore a diacrylate. In some alternatives described herein, the acrylate for manufacturing a polymer prodrug is a diacrylate. Diacrylates can include but is not limited to 1,3-Butanediol diacrylate, 1,6-Hexanediol diacrylate, Bisphenol A ethoxylate diacrylate, Poly(ethylene glycol) diacrylate, Ethylene glycol diacrylate, 1,4-Butanediol diacrylate, Pentaerythritol diacrylate monostearate, Glycerol 1,3Diglycerolate diacrylate, Poly(ethylene glycol) diacrylate, Di(ethylene glycol) diacrylate, Neopentyl glycol diacrylate, Tetra(ethylene glycol) diacrylate, Poly(propylene glycol) diacrylate, Tri(ethyleneglycol) diacrylate, Tri(propylene glycol) diacrylate, Bisphenol A glycerolate (1 glycerol/phenol) diacrylate, Tricyclo[$5.2.1.0^{2.6}$]decanedimethanol diacrylate, 1,6-Hexanediol ethoxylate diacrylate, Fluorescein O,O'-diacrylate, Bisphenol F ethoxylate (2 EO/phenol) diacrylate, Neopentyl glycol propoxylate (1 PO/OH) diacrylate, Poly(Disperse Red 19-p-phenylene diacrylate), Trimethylolpropane ethoxylate (1 EO/OH) methyl ether diacrylate, poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) and diethylene glycol diacrylate (DEGDA). In some alternatives, the diacrylate is 1,3-Butanediol diacrylate, 1,6-Hexanediol diacrylate, Bisphenol A ethoxylate diacrylate, Poly(ethylene glycol) diacrylate, Ethylene glycol diacrylate, 1,4-Butanediol diacrylate, Pentaerythritol diacrylate monostearate, Glycerol 1,3Diglycerolate diacrylate, Poly(ethylene glycol) diacrylate, Di(ethylene glycol) diacrylate, Neopentyl glycol diacrylate, Tetra(ethylene glycol) diacrylate, Poly (propylene glycol) diacrylate, Tri(ethyleneglycol) diacrylate, Tri(propylene glycol) diacrylate, Bisphenol A glycerolate (1 glycerol/phenol) diacrylate, Tricyclo[$5.2.1.0^{2.6}$] decanedimethanol diacrylate, 1,6-Hexanediol ethoxylate diacrylate, Fluorescein O,O'-diacrylate, Bisphenol F ethoxylate (2 EO/phenol) diacrylate, Neopentyl glycol propoxylate (1 PO/OH) diacrylate, Poly(Disperse Red 19-p-phenylene diacrylate), Trimethylolpropane ethoxylate (1 EO/OH) methyl ether diacrylate, poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the acrylate comprises a molecular weight of 170, 250, 575, 700, 1000, 2000, 3500, 5000, 10000, g/mol, or any other molecular weight within a range defined by any two of the aforementioned values.

"Primary amine group" as described herein, is when one of three hydrogen atoms in ammonia is replaced by an alkyl or aromatic. Important primary alkyl amines can include but is not limited to methylamine, ethanolamine (2-aminoethanol) and primary aromatic amines which can include aniline. Primary amine groups can be seen in all amino acids with the exception of proline. Amino acids with side chains that comprise a primary amine can include but is not limited to arginine, lysine, asparagine and glutamine. In some alternatives described herein, a drug can have at least one primary amine group.

"Secondary amines" as described herein, have two organic substituents (alkyl, aryl or both) bound to nitrogen (N) together with one hydrogen (or no hydrogen if one of the substituent bonds is double). Without being limiting, secondary amines can be found in some amino acids, for example, arginine, histidine, proline and tryptophan. In some alternatives described herein, a drug can have at least two secondary amine groups.

"Polymerization" as described herein, refers to a reaction in which molecules are covalently bound together to form a network of polymer chains or a three dimensional network of polymer chains. In some alternatives described herein, methods are performed to manufacture a polymer prodrug or a hydrogel prodrug, wherein, the polymer prodrug comprises polymerized drug to an acrylate molecule and the hydrogel prodrug comprises polymerized polymer prodrugs.

Figure 13:
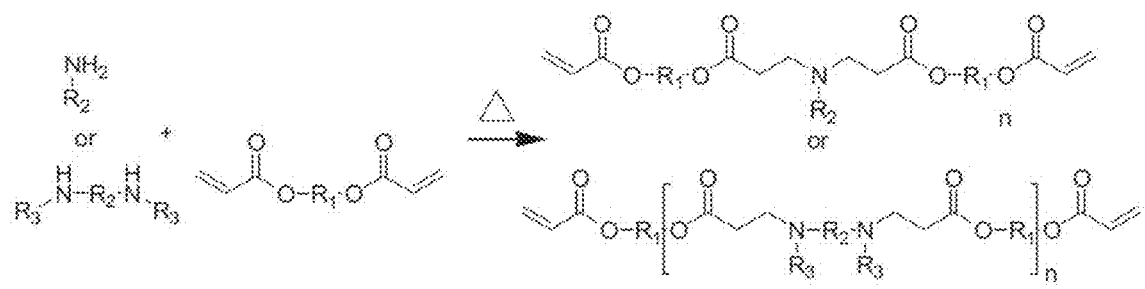
FIG. 13 shows an example of a polymerization schematic acquired from Anderson, et al. (A combinatorial library of photocrosslinkable and degradable materials. Advanced Materials 2006, 18, 2614-2618; incorporated by reference in its entirety herein). In this schematic, the amine molecule is the drug.

"Polymer prodrug" comprises a polymer carrier and a drug or prodrug. The prodrug can comprise a drug that is biologically inactive compound that can be metabolized in the body to produce the active drug. The drug can be a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the prodrug comprises at least one acrylate that is bound to a drug or prodrug. The polymer prodrug can also more generally refer to a drug incorporated into the backbone of a polymer, or attached directly as a side group to a polymer, or attached via a linker as a side group to a polymer. The drug may be freed enzymatically or hydrolytically from the polymer and released in its original, unaltered state, or it may be freed from the polymer in a modified, but still biologically active, state, for example, in soluble oligomeric form. In several alternatives, the formulations are focused on the first example (backbone incorporated)—the other exemplary alternatives (directly or indirectly attached as a side group) are well-characterized and are commonly used. In some alternatives, the prodrug is made by reacting an acrylate with at least one primary amine group or at least two secondary amine groups of the drug in a polymerization reaction. An example reaction is shown in FIG. 13.

"Cross-link" is a bond that can link one molecule to another or link a polymer chain to another chain or molecule. Cross-links can be found between at least two polymer chains, at least two molecules, at least two nucleic acids, at least two proteins or in combinations of the aforementioned groups described. In the alternatives described herein, the bond can be a covalent bond or an ionic bond. In some of the alternatives described herein, reactive groups that can participate in cross-linking can include primary and secondary amine groups.

"Cross-linking" is a reaction in which polymers, proteins, molecules, nucleic acids or combinations of the aforementioned groups are cross-linked together. In polymer chemistry, a synthetic polymer can be cross-linked to a drug, protein, nucleic acid, molecule, or any other type of material known to those skilled in the art that comprises groups that allows the material to be cross-linked to the synthetic polymer. The cross-link density can also play a role in the mechanical properties of the polymer. As known to those skilled in the act, low cross-link densities can decrease the viscosity of a polymer or lead to a very "gummy" type of a polymer, intermediate cross-link density can lead to a material that has elastomeric properties and potentially high strength, and a high level of cross-links can lead to a more rigid type of a polymer.

A "catalyst" as described herein refers to a substance that increases the rate of a chemical reaction without itself undergoing any permanent chemical change. In some alternatives described herein, the cross-linking is performed in the presence of a catalyst. In some alternatives, the catalyst is Tetramethylethylenediamine (TEMED).

A "free radical initiator" is a substance that can promote the production of free radical species under mild conditions in order to promote a free radical reaction. Examples of free radical initiators can include but are not limited to 4,4'-Azobis(4-cyanovaleric acid), 4,4'-Azobis(4-cyanovaleric acid), 1,1'-Azobis(cyclohexanecarbonitrile), azobisisobutyronitrile, 2,2'-azobis(2-methylpropionamidine) dihydrochloride granular, 2,2'-Azobis(2-methylpropionitrile), 2,2'-Azobis(2-methylpropionitrile), smmonium persulfate reagent grade, hydroxymethanesulfinic acid monosodium salt dehydrate, potassium persulfate, sodium persulfate, tert-Butyl hydroperoxide, tert-Butyl hydroperoxide, tert-Butyl hydroperoxide, tert-Butyl peracetate, cumene hydroperoxide, 2,5-Di(tert-butylperoxy)-2,5-dimethyl-3-hexyne, 2,5-Di(tert-butylperoxy)-2,5-dimethyl-3-hexyne, dicumyl peroxide, Luperox® 101, 2,5-Bis(tert-butylperoxy)-2,5-dimethyl-hexane technical grade, Luperox® 101XL45, 2,5-Bis(tert-butylperoxy)-2,5-dimethylhexane, Luperox® 224, 2,4-Pentanedione peroxide solution ~34 wt. % in 4-hydroxy-4-methyl-2-pentanone and N-methyl-2-pyrrolidone, Luperox® 231, 1,1-Bis(tert-butylperoxy)-3,3 ,5-trimethyl-cyclohexane, Luperox® 331M80, 1,1-Bis(tert-butylperoxy) cyclohexane, Luperox® 531M80, 1,1-Bis(tert-amylperoxy) cyclohexane solution, Luperox® A70S, Benzoyl peroxide, Luperox® A75, Benzoyl peroxide 75%, Luperox® A75FP, Benzoyl peroxide, Luperox® A98, Benzoyl peroxide, Luperox® AFR40, Benzoyl peroxide, Luperox® ATC50, Benzoyl peroxide, Luperox® DDM-9, 2-Butanone peroxide solution ~35 wt. % in 2,2,4-trimethyl-1,3-pentanediol diisobutyrate, Luperox® DHD-9, 2-Butanone peroxide solution, Luperox® DI, tert-Butyl peroxide, Luperox® LP, Lauroyl peroxide, Luperox® P, tert-Butyl peroxybenzoate, Luperox® TBEC, tert-Butylperoxy 2-ethylhexyl carbonate, and Luperox® TBH70X, tert-Butyl hydroperoxide solution.

In some alternatives described herein, the method for making a hydrogel prodrug comprises providing a free radical initiator. In some alternatives, the free radical initiator is 4,4'-Azobis(4-cyanovaleric acid), 4,4'-Azobis(4-cyanovaleric acid), 1,1'-Azobis(cyclohexanecarbonitrile), azobisisobutyronitrile, 2,2'-azobis(2-methylpropionamidine) dihydrochloride granular, 2,2 '-Azobis(2-methylpropionitrile), 2,2'-Azobis(2-methylpropionitrile), smmonium persulfate reagent grade, hydroxymethanesulfinic acid monosodium salt dehydrate, potassium persulfate, sodium persulfate, tert-Butyl hydroperoxide, tert-Butyl hydroperoxide, tert-Butyl hydroperoxide, tert-Butyl peracetate, cumene hydroperoxide, 2,5-Di(tert-butylperoxy)-2,5-dimethyl-3-hexyne, 2,5-Di(tert-butylperoxy)-2,5-dimethyl-3-hexyne, dicumyl peroxide, Luperox® 101, 2,5-Bis(tert-butylperoxy)-2,5-dimethylhexane technical grade, Luperox® 101XL45, 2,5-Bis(tert-butylperoxy)-2,5-dimethylhexane, Luperox® 224, 2,4-Pentanedione peroxide solution ~34 wt. % in 4-hydroxy-4-methyl-2-pentanone and N-methyl-2-pyrrolidone, Luperox® 231, 1,1-Bis(tert-butylperoxy)-3,3,5-trimethylcyclohexane, Luperox® 331M80, 1,1-Bis(tert-butylperoxy)cyclohexane, Luperox® 531M80, 1,1-Bis(tert-amylperoxy)cyclohexane solution, Luperox® A70S, Benzoyl peroxide, Luperox® A75, Benzoyl peroxide 75%, Luperox® A75FP, Benzoyl peroxide, Luperox® A98, Benzoyl peroxide, Luperox® AFR40, Benzoyl peroxide, Luperox® ATC50, Benzoyl peroxide, Luperox® DDM-9, 2-Butanone peroxide solution ~35 wt. % in 2,2,4-trimethyl-1,3-pentanediol diisobutyrate, Luperox® DHD-9, 2-Butanone peroxide solution, Luperox® DI, tert-Butyl peroxide, Luperox® LP, Lauroyl peroxide, Luperox® P, tert-Butyl peroxybenzoate, Luperox® TBEC, tert-Butylperoxy 2-ethylhexyl carbonate, Luperox® TBH70X, tert-Butyl hydroperoxide solution or ammonium persulfate (APS). In some alternatives, the free radical initiator is APS. In some alternatives, the free radical initiator is a light-activated free radical initiator. In some alternatives, the light-activated free radical initiator is DMPA.

"Heteroatom" as described herein, refers to an atom that is not a carbon or a hydrogen that is within a ring structure. Without being limiting, typical heteroatoms can be nitrogen, oxygen, Sulphur, phosphorus, chlorine, bromine and iodine. However, in a describing a protein, a heteroatom can be an atom bellowing to a small molecule cofactor rather than being part of the biopolymer or protein chain.

"Unsaturated carbon-carbon bond" refers to carbon-carbon double or triple bonds which can be found, for example, in alkenes or alkynes, respectively. "Saturated carbon-carbon bond" refers to a carbon-carbon bond in which the carbons are held together by single bonds.

"Chemical spacer" can serve as a spacer group within a hydrogel prodrug. In some alternatives, the hydrogel prodrug comprises a spacer or spacer group. In some alternatives, the chemical spacer comprises at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer comprises one or more primary amines, two or more secondary amine groups, or a combination of primary and secondary amines.

"Subject" or "patient," as described herein, refers to any organism upon which the alternatives described herein may be used or administered, e.g., for experimental diagnostic, prophylactic, and/or therapeutic purposes. Subjects or patients include, for example, animals. In some alternatives, the subject is mice, rats, rabbits, non-human primates, and humans. In some alternatives, the subject is a cow, sheep, pig, horse, dog, cat primate or a human. In some alternatives, the subject is human. In some alternatives, the subject is suffering from a disease, such as cancer.

"Specific" or "Specificity" can refer to the characteristic of a ligand for the binding partner or alternatively, the binding partner for the ligand, and can include complementary shape, charge and hydrophobic specificity for binding. Specificity for binding can include stereospecificity, regioselectivity and chemoselectivity. In some alternatives, the hydrogel prodrug further comprises a targeting moiety. The targeting moiety can be incorporated into or linked to the hydrogel prodrug. In some alternatives, the targeting moiety is specific for a tissue or a cell that is in need of treatment. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. In some alternatives, the targeting moiety is specific for a ligand on a tumor. In some alternatives, the targeting moiety is specific for a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the targeting moiety comprises a protein or portion thereof. In some alternatives, the targeting moiety comprises an antibody or portion thereof. In some alternatives, the targeting moiety comprises a small chain variable fragment (ScFv).

DETAILED DESCRIPTION

The alternatives described herein are directed to hydrogel prodrugs for the controlled release of therapeutics. The hydrogel prodrugs described herein can have drugs or prodrugs synthesized into a flexible hydrogel polymer material, which can come with multiple benefits. The hydrogel prodrug manufactured by the alternatives described herein, can then be localized to a particular treatment site and at very precise dosages. In the alternatives described herein, the preferred alternatives have a zero order drug release kinetic, which indicates that there is a constant therapeutic dosage which is not seen in drugs that are continuously given at intervals such as a pill, capsule or an injection or other currently known therapeutics on the market. Furthermore, the systems described herein can be flexible to use, easier to manufacture, and is shelf-stable in mild conditions.

Drug delivery systems have improved the delivery of drugs over time. As shown in FIG. 1, is a comparison of drug release kinetics over time in which a drug regimen is compared with a drug system with controlled release. As shown, the "bolus dose" curve indicates the kinetics of a basic pill or of an injection. The "controlled release" curve illustrates a generic drug delivery system. The curve for the bolus drug indicates that there is an initial burst of drug being released soon after the first dose. In this example, the levels of drug within this system can reach a toxic level before being quickly metabolized. This cyclic release and metabolism of the bolus drug can be seen with the second and the third dose. Regarding the drug delivery system, after the first initial dosage, the drug can be released in a controlled manner such that over time, the drug is within the biological system at a level that is above the therapeutic minimum and is below the toxic maximum. In the alternatives described herein, the hydrogel prodrug is designed to have improved release characteristics that allow release of the drug in which the concentrations of the drug is above the therapeutic minimum and below the toxic maximum.

Figure 2:
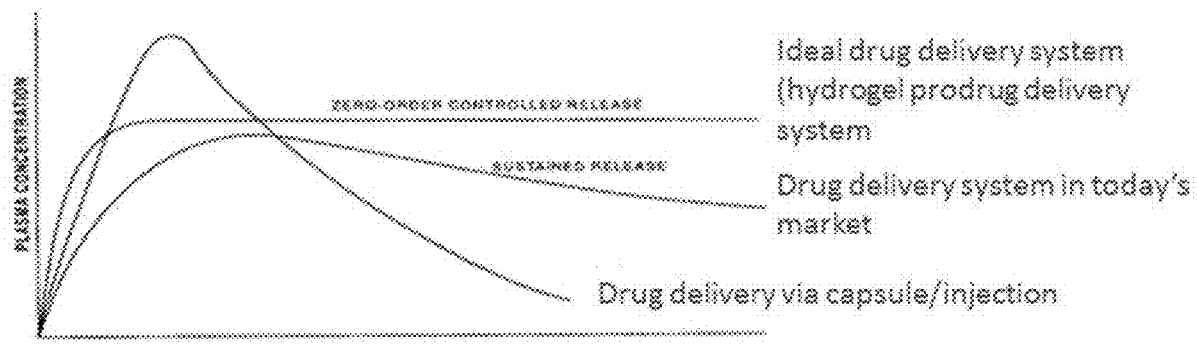
FIG. 2 shows a concentration profile of the hydrogel prodrug releasing a drug in comparison to an example drug release system, and a drug delivered via capsule or injection. The level of drug concentration in the plasma is shown over time after the first dosage.

The problem with today's drug delivery by capsule or injections have shown that there can be a spike in the concentration of the drug that then leads to a sustained release in which the drug concentration in the plasma goes down with time (plasma concentration vs. time) (See FIG. 2). As shown, most drug delivery systems are directed towards sustained release, in which there is an initial spike of drug in the plasma that slowly decreases in concentration over time. However in the alternatives described herein, the preferred release of the drug has zero order release kinetics, in which the drug is gradually released at a constant set dosage for a specific amount of time.

There are many barriers of the previously used polymeric drug delivery systems. There is a strong initial drug burst (dosage is "front loaded"), nonlinear release kinetics (FIG. 2), lack of material biocompatibility as well as degradation concerns. In to improve these existing systems, the alternatives described herein have been manufactured to have a zero initial burst and constant release rate of the drug.

In order to sustain the release of the drug at a constant concentration, the drugs are made to be an essential part of the material backbone of the hydrogel prodrug, in which the drug release and the polymer degradation occurs at the same time. In some existing release systems, the drugs are trapped within a polymer structure. This can lead to a drug release rate that is at a different rate than the polymer degradation. As such the polymer may remain when the drug release is complete. In order to synchronize the rates of drug release and polymer degradation, in the alternatives provided herein, the drugs are an essential part of the polymer backbone. Thus drug release and polymer degradation occurs simultaneously.

Previous existing systems of drug release polymers were also processed in methods that required multiple polymer processing steps, high temperatures, harsh solvents and detergents. Multiple processing can lead to production of byproducts which require extensive purification steps which can lead to loss of drug as well as product. Reaction conditions that require high temperatures, harsh solvents, or detergents can negatively impact drug activity or biocompatibility of the material. Furthermore, some systems also have the step of drug encapsulation which can lead to drug being lost during each processing step. Additionally, additives, such as plasticizers can also be required in older drug release systems.

In the alternatives described herein, the methods for making the hydrogel prodrug compositions have a one-step drug polymer synthesis. As there is little to no byproducts formed, there is no need for purification in some alternatives. The one step synthesis also leads to the drug being incorporated during the one step polymerization and cross-linking into the desired geometry.

The existing systems also have the disadvantage in that the microarchitecture and molecular geometry could be a limiting factor. For example, each dosage form requires extensive and specific processing conditions. Unfortunately the same polymer used to form microparticles, for example, may not be suitable to make thin films or other forms of the drug. In the alternatives, described herein, the hydrogel prodrug and hydrogel prodrug compositions are soft flexible materials that can be cast into any shape. Without being limiting the hydrogel prodrug compositions can be in the form of thin flexible films, implants, microparticles and pills.

The use of a hydrogel prodrug formulation as described herein can exhibit zero-order release kinetics, which would keep the drug at a steady concentration in a subject that is being treated.

PBAE Structures
General Structure of the Polymer Backbone

Figure 3:
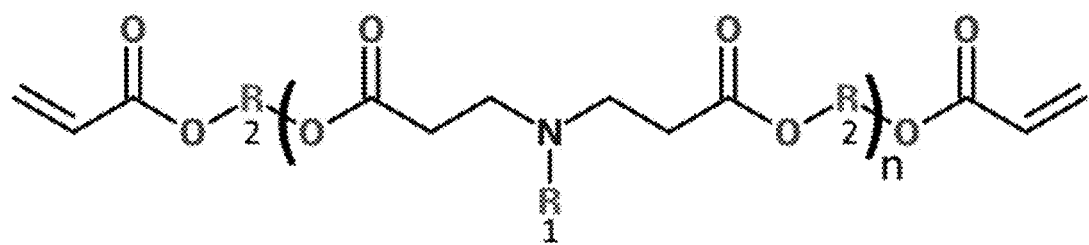
FIG. 3 shows a general PBAE structure, which is a generalized structure of the backbone of the hydrogel prodrugs produced.

Poly(beta amino ester)s (PBAEs) is a class of polymers. A general PBAE structure is shown in FIG. 3.

In some alternatives, when there is only one amine and one diacrylate, the copolymer that is synthesized is an alternating copolymer.

Figure 4:
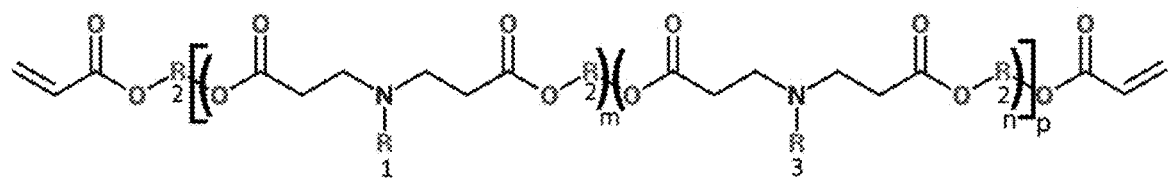
FIG. 4 shows a general structure of a periodic (not random) PBAE containing two diacrylates and one amine.

However, in some alternatives, wherein there are multiple amines and diacrylates (this is the case for several working alternatives and formulations described herein), there can be some degree of randomness when it comes to the exact sequence of amines and diacrylates. This is typical of these types of polymers, and is not central to the technology unless there is evidence that controlling the periodicity of the monomers provides some benefit. A general structure of a periodic (not random) PBAE containing two diacrylates and one amine is shown in FIG. 4.

PBAEs containing two amines and one diacrylate are likely to adopt a random sequence. Conceivably, PBAEs containing two amines and two diacrylates, or even greater numbers of each component, can be synthesized. Figures for these higher-order polymers are not included, because the complexity of the structures becomes immense very quickly due to the potential number of permutations.

In some alternatives, PBAEs containing two amines (one of which is an amine-containing drug), and one or two diacrylates are provided. In some alternatives, formulations can also be synthesized using additional amines and diacrylates in order to incorporate additional drugs or modulate the physical or chemical properties of the material. These higher order polymers would thus permit a single formulation to release multiple drugs at the same rate. In some alternatives, the hydrogel prodrug comprises multiple drugs wherein the drugs are released at the same rate. The amine containing drug will be part of the backbone of the hydrogel prodrug. In some alternatives, the drug is incorporated into the backbone of the hydrogel prodrug.

It is also envisioned that two separate polymer prodrugs can be created, in which each polymer prodrug contains its own drug and is formulated to release a drug at a certain rate, and then blending these two polymer prodrugs together to create a mixture that is subsequently cross-linked. This is distinct from directly synthesizing a copolymer, because the final hydrogel will contain two (or more, depending on the number of polymers mixed) distinct regions, each with its own characteristic degradation rate. This would permit a single formulation to release multiple drugs at distinct rates.

In some alternatives, the hydrogel prodrug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and tenofovir, valsartan, hydrochloraothiazide, lisdexamfetamine, mesalamine, memantine, pemetrexed, fingolimod, sitagliptin, metformin or darunavir. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the protein is insulin or lysozyme.

Cross-Linking the Polymer into a Hydrogel Prodrug

Figure 5:
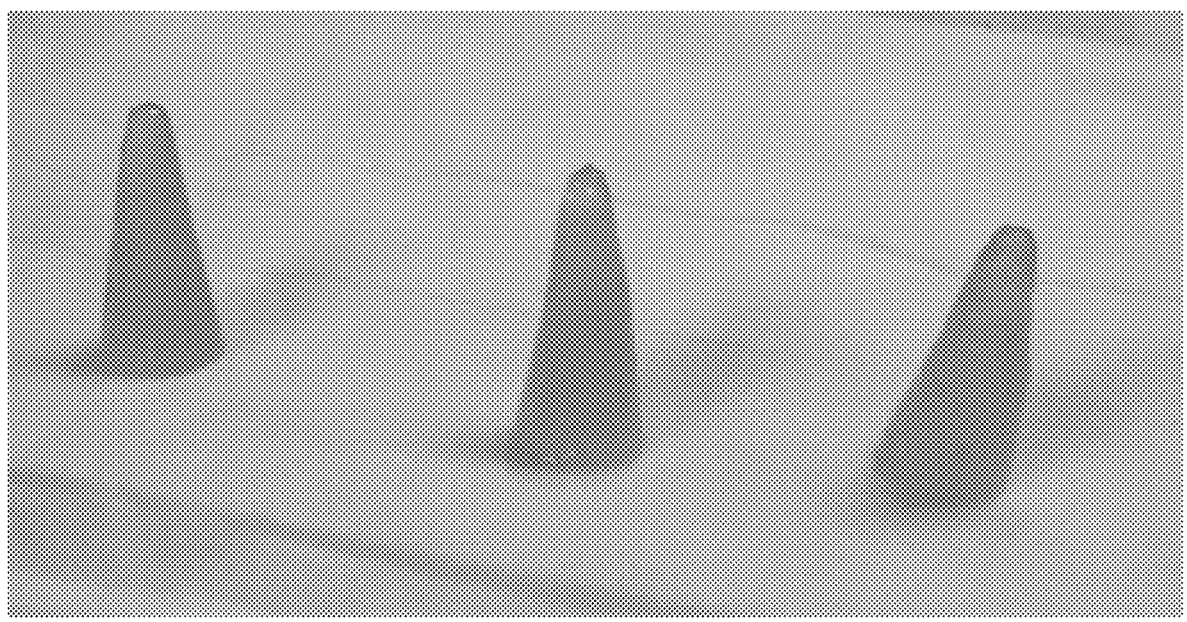
FIG. 5 shows a mold casted polymer prodrug. The polymer prodrug can be placed into a mold prior to cross-linking. Upon cross-linking, the polymer prodrug solidifies into a flexible solid material, a hydrogel prodrug, in the shape of the mold. As shown, the polymer prodrugs were cast into microcentrifuge tubes, and the resulting hydrogel prodrugs seen here, made from tranexamic acid, retain the conical tube shape. These conical hydrogels were used for subsequent drug release studies.

In some alternatives, the polymer prodrug can be cross-linked within a mold. As shown in FIG. 5, is a drug cross-linked into a hydrogel prodrug in the shape of a cone, in this exemplary alternative, it is tranexamic acid cross-linked into a conical shaped polymer (FIG. 5). The hydrogel prodrugs can swell in water and are biodegradable. The degradation is controlled by altering the material chemistry. In the alternatives described herein, the hydrogels synthesized are made entirely from market-available drugs and FDA approved material. As such, there are no toxic ingredients or by-products. Physically the material is soft, flexible and able to be manufactured into any desired shape, such as a flat sheet, pill, implant or microparticles. In terms of scale, these particular samples can be smaller than the head of a pencil, but 1 the size and shape can be easily controlled. These hydrogel prodrugs can be made from market-available drugs and FDA approved material. As such there are no toxic ingredients or toxic byproducts.

Figure 6:
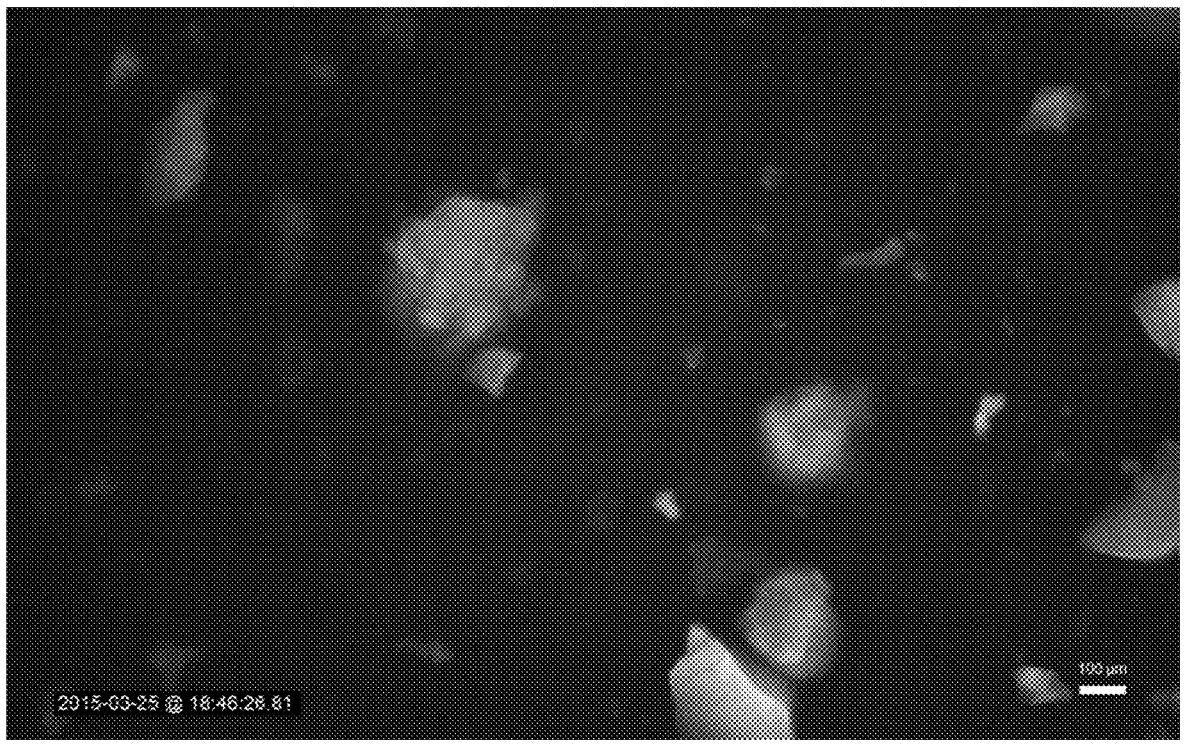
FIG. 6 shows a microparticle formulation of the hydrogel prodrug.

As shown in FIG. 6, the hydrogel prodrug can be made into a microparticle formulation. Hydrogel prodrugs can be ground into microparticles capable of being suspended in aqueous solutions and injected. As seen in the micrograph FIG. 6, particles range in size from less than 10 microns to 200-300 microns in diameter.

In some alternatives, the hydrogel prodrug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction drugs, anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and tenofovir, valsartan, hydrochloraothiazide, lisdexamfetamine, mesalamine, memantine, pemetrexed, fingolimod, sitagliptin, metformin or darunavir. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the hydrogel prodrug comprises a protein. In some alternatives the protein is lysozyme or insulin.

Co-Polymerization of Mesalamine with a Polymer

Figure 7A:
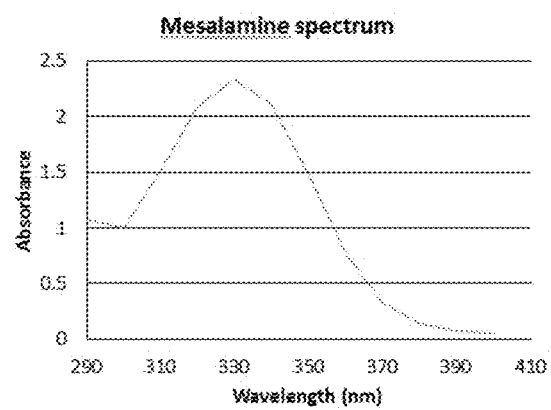
FIGS. 7A and 7B shows the detection of mesalamine from a hydrogel prodrug. 7A shows the wavelength scan of mesalamine. 7B is the mesalamine standard curve.
Figure 7B:
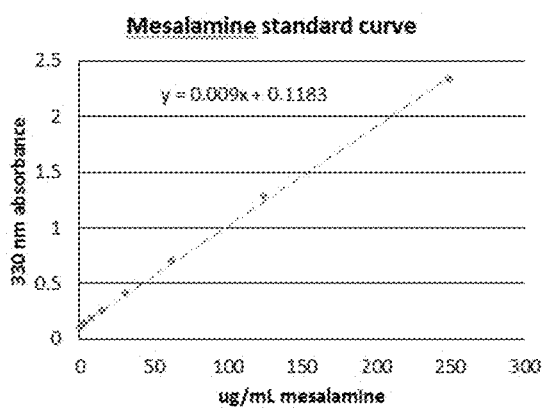

A hydrogel prodrug was manufactured to contain mesalamine, a commonly used anti-inflammatory. The mesalamine polymer was synthesized by first dissolving 500 mg of the drug mesalamine (about 3.3 mmol) in 2 mL of the spacer chemical isobutylamine (1472 mg, about 20.1 mmol). Thus, the total quantity of amines is about 23.4 mmol. Then, this solution was added to one of the following diacrylates or diacrylate mixtures, depending on the formulation. For faster-degrading hydrogel prodrugs, the amine solution was added to 16 g PEG575DA (about 27.8 mmol). For slower-degrading hydrogel prodrug, the amine solution was added to a mixture of 5.3 g PEG575DA (about 9.3 mmol) and 3.96 g DEGDA (about 18.5 mmol). The amine-diacrylate mixture was vortexed until the amine solution was fully dissolved in the diacrylate. This solution was reacted at 75° C. in a covered vial under constant stirring for 48 hours to polymerize, resulting in an acrylate-terminated mesalamine polymer prodrug containing a molar ratio of 1.2:1 diacrylate: amine. This mesalamine polymer prodrug was stored at 4° C. until use. To create a mesalamine hydrogel prodrug, 500 mg of mesalamine polymer prodrug was weighed. Relative to the mass of polymer prodrug, 3% APS (15 mg) was dissolved in 150 μL DMSO. Relative to the mass of polymer prodrug, 4.5% TEMED (22.5 mg, 28.976 uL) was added to the APS solution and vortexed to thoroughly mix. Then, this mixture was added to the 500 mg of mesalamine polymer prodrug, and was thoroughly mixed. This mixture was placed in a bath sonicator for 15 minutes, and then allowed to cross-link for 24 hours. The cross-linking reaction produced mesalamine hydrogel prodrug, which was washed serially in ethanol to remove unreacted components and the soluble fraction, and then dried thoroughly and stored in dry conditions. As shown in FIG. 7, is a wavelength scan to find the absorbance of mesalamine alone in order to detect mesalamine in a hydrogel prodrug. Mesalamine was dissolved in isobutylamine (200 mg/mL) and diluted in water (2 mg/mL) to mimic supernatant collected in release studies, and this solution exhibited a characteristic spectrum (left) with a local maximum at 330 nm. The optical absorbance of mesalamine followed the Beer-Lambert law in the working range of <300 ug/mL, so a linear standard curve at 330 nm (right) was used to calculate drug concentration for release studies.

Figure 8:
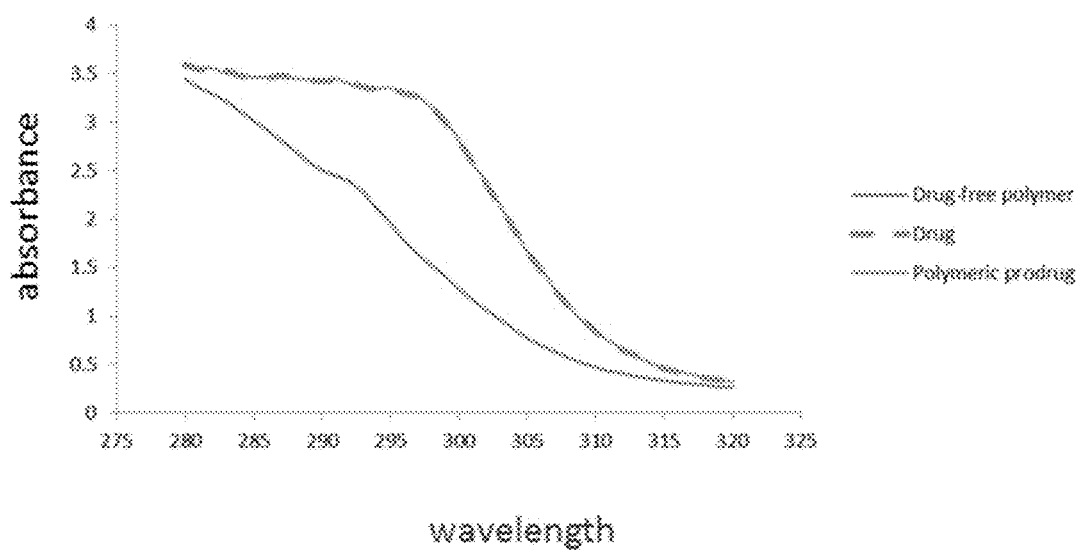
FIG. 8 shows a wavelength scan comparing the peaks of drug-free polymer, drug (mesalamine) and polymeric drug (mesalamine).

As shown in FIG. 8, the peaks for the polymeric prodrug and drug overlap, indicating that the drug is incorporated into the polymeric prodrug (hydrogel prodrug). As a control, the drug free polymer is shown, and does not have a high absorbance at 330 nm.

Figures 9A, 9B:
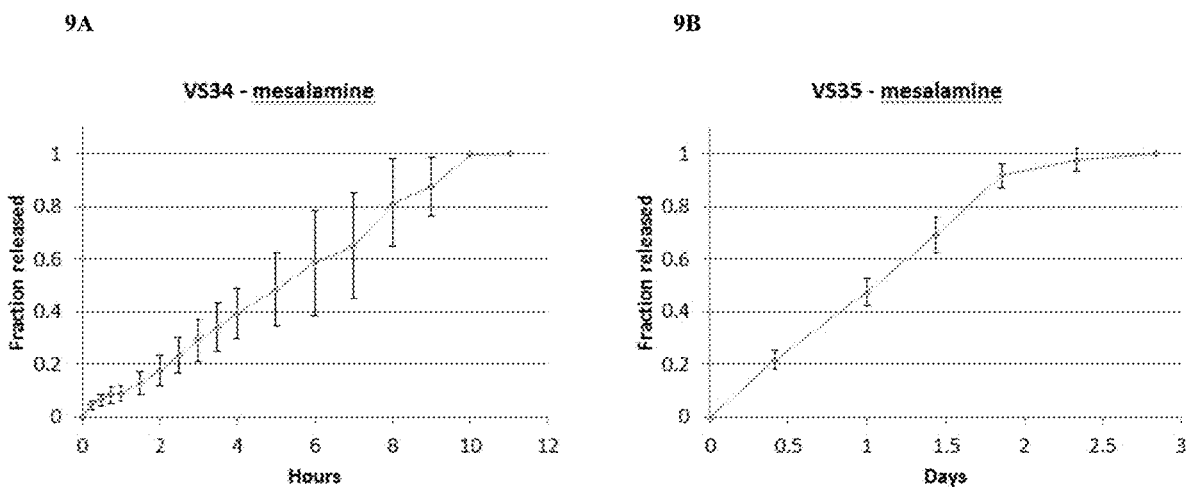
FIGS. 9A-9B show the near linear release of a drug (mesalamine) over 10 hours (Formulation VS34) and the near linear release of a drug (mesalamine) over 3 days (formulation VS35) using two formulations of a hydrogel prodrug in which both types release mesalamine.

As shown in FIGS. 9A and 9B, the hydrogel prodrug can be designed to release mesalamine for a short term or long term treatment. As shown in FIGS. 9A-9B, Mesalamine hydrogel prodrugs were formulated to release mesalamine for 10 hours (VS34, left), or for 2 days (VS35, right). Release studies were conducted by immersing 500 mg hydrogel prodrug samples in 10 mL water at 37 C with constant gentle shaking, and sampling the supernatant at intervals with replacement of the sampled volume. For each formulation, the same reaction conditions were used, and only the chemical nature of the diacrylate was varied. Both formulations exhibited zero-order release, and the completion of drug release coincided with the complete degradation (no visible material remaining) of the hydrogel. As shown, the co-polymerized mesalamine had a near-linear release of drugs over hours and days as desired. PEG575DA is a more hydrophilic molecule than DEGDA, owing to its higher number of ethylene glycol repeat units, and therefore hydrogels containing a higher PEG575DA content tend to degrade more quickly than those with a higher DEGDA content. The degradation time can be extended by increasing the DEGDA:PEG575DA ratio, which decreases the hydrophilicity of the polymer and therefore delays hydrolytic cleavage of ester bonds in the polymer backbone. Conceivably, any number of diacrylates can be used individually or combined in place of the diacrylates used in these formulations in order to customize the degradation and drug release kinetics of these hydrogel prodrugs. In addition to the hydrophilicity of the diacrylate, the size of the molecule is inversely related to crosslink density, which means shorter diacrylate molecules will lead to more densely crosslinked hydrogel prodrugs. Densely crosslinked hydrogel prodrugs conceivably degrade more slowly than loosely crosslinked hydrogel prodrugs.

In some alternatives, the degradation time of the hydrogel prodrug is extended by manufacturing a hydrogel prodrug with an increased hydrophobic content. In some alternatives, the hydrophobic content of the hydrogel prodrug is increased by addition of DEGDA during the polymerization reaction or the cross-linking reaction. In some alternatives, the hydrophobic content of the hydrogel prodrug is increased by addition of excess diacrylate. In some alternatives, the hydrophobic content of the hydrogel prodrug is increased by addition of excess diacrylate which can lead to a prolonged release of the drug.

Co-Polymerization of Tranexamic Acid with a Polymer

Figures 10A, 10B:
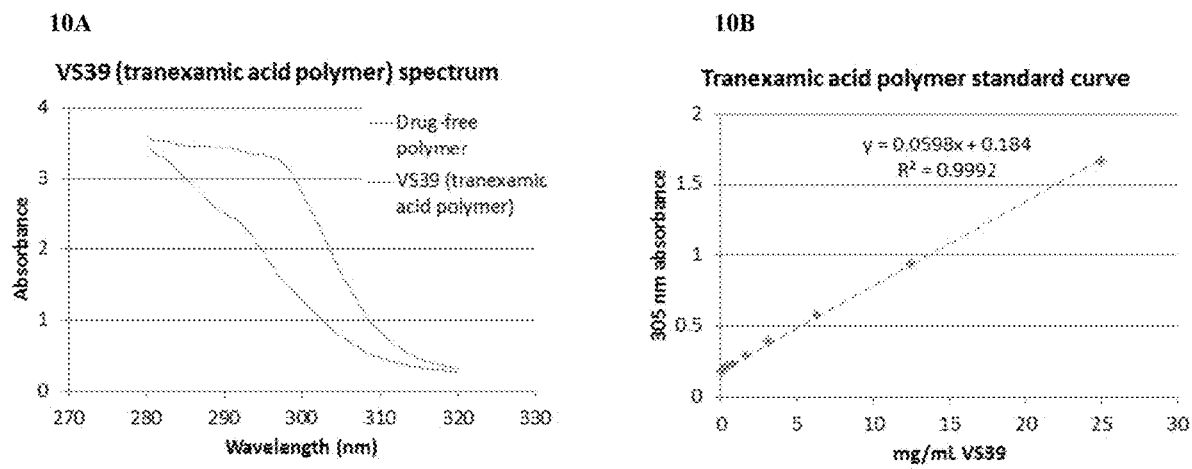
FIGS. 10A-10B shows the detection of tranexamic acid from a hydrogel.

A hydrogel prodrug was manufactured to contain tranexamic acid, a commonly used anti-fibrinolytic used to prevent hemorrhage. A tranexamic acid polymer was synthesized by first dissolving 75 mg of the drug tranexamic acid (about 0.48 mmol) in 500 µL of deionized water. To this solution, 440 µL of the spacer chemical isobutylamine (324 mg, about 4.4 mmol) was added. Thus, the total quantity of amines is about 4.48 mmol. Then, this solution was added to one of the following diacrylates or diacrylate mixtures, depending on the formulation. For faster-degrading hydrogel prodrugs, the amine solution was added to 3.1 g PEG575DA (about 5.4 mmol). For slower-degrading hydrogel prodrug, the amine solution was added to a mixture of 1 g PEG575DA (about 1.8 mmol) and 771.1 g DEGDA (about 3.6 mmol). The amine-diacrylate mixture was vortexed until the amine solution was fully dissolved in the diacrylate. This solution was reacted at 70 C in a covered vial under constant stirring for 48 hours to polymerize, resulting in an acrylate-terminated tranexamic acid polymer prodrug containing a molar ratio of 1.2:1 diacrylate:amine. This tranexamic acid polymer prodrug was stored at 4 C until use. To create a mesalamine hydrogel prodrug, 500 mg of tranexamic acid polymer prodrug was weighed. Relative to the mass of polymer prodrug, 3% APS (15 mg) was dissolved in 150 µL DMSO. Relative to the mass of polymer prodrug, 4.5% TEMED (22.5 mg, 28.976 uL) was added to the APS solution and vortexed to thoroughly mix. Then, this mixture was added to the 500 mg of tranexamic acid polymer prodrug, and was thoroughly mixed. This mixture was placed in a bath sonicator for 15 minutes, and then allowed to cross-link for 24 hours. The cross-linking reaction produced mesalamine hydrogel prodrug, which was washed serially in ethanol to remove unreacted components and the soluble fraction, and then dried thoroughly and stored in dry conditions. FIGS. 10A and 10B shows a wavelength scan of tranexamic acid from a hydrogel and a hydrogel without any drug as a control. As shown, tranexamic acid polymers exhibited a characteristic spectrum (FIG. 10A) distinct from drug-free polymers using the same acrylate and spacer. The optical absorption of tranexamic acid polymer followed the Beer-Lambert law in the working range of <30 mg/mL, so a linear standard curve at 305 nm (FIG. 10B) was used to calculate drug concentration for release studies.

Figure 11A:
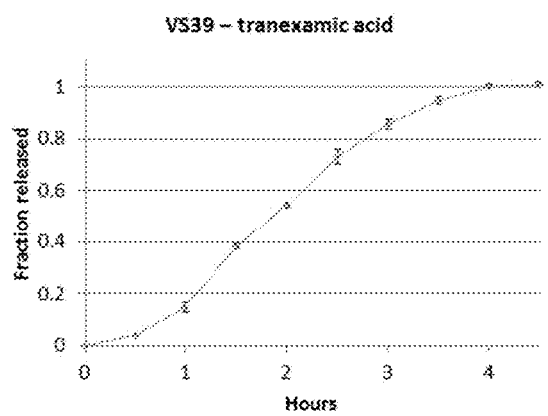
FIGS. 11A-11B shows the tranexamic acid release kinetics for two different formulations of the hydrogel prodrugs containing the tranexamic acid.
Figure 11B:
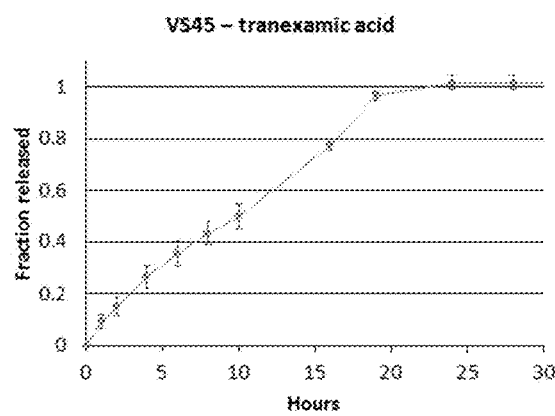

As shown in FIGS. 11A and 11B, use of the formulations of hydrogel prodrug herein, lead to a drug release system that can allow non-linear release of a drug over several hours. In an exemplary alternative described herein, tranexamic acid, an antibifrinolytic used to prevent hemorrhaging was cross linked to a polymer backbone, to make a hydrogel prodrug containing tranexamic acid. The hydrogel prodrug demonstrated a near linear release of drug for over 4 hours. Alternatively, a tranexamic acid hydrogel prodrug was formulated using a formulation that differed only by increasing the DEGDA content of the diacrylate from 0% to 66.6%, and resulted in linear release of drug over 20 hours. Release studies were conducted by immersing 500 mg hydrogel prodrug samples in 10 mL water at 37 C with constant gentle shaking, and sampling the supernatant at intervals with replacement of the sampled volume.

PEG575DA is a more hydrophilic molecule than DEGDA, owing to its higher number of ethylene glycol repeat units, and therefore hydrogels containing a higher PEG575DA content tend to degrade more quickly than those with a higher DEGDA content. The degradation time can be extended by increasing the DEGDA:PEG575DA ratio, which decreases the hydrophilicity of the polymer and therefore delays hydrolytic cleavage of ester bonds in the polymer backbone. Conceivably, any number of diacrylates can be used individually or combined in place of the diacrylates used in these formulations in order to customize the degradation and drug release kinetics of these hydrogel prodrugs. In addition to the hydrophilicity of the diacrylate, the size of the molecule is inversely related to crosslink density, which means shorter diacrylate molecules will lead to more densely crosslinked hydrogel prodrugs. Densely crosslinked hydrogel prodrugs conceivably degrade more slowly than loosely crosslinked hydrogel prodrugs.

In some alternatives, the degradation time of the hydrogel prodrug is extended by manufacturing a hydrogel prodrug with an increased hydrophobic content. In some alternatives, the hydrophobic content of the hydrogel prodrug is increased by addition of DEGDA during the polymerization reaction or the cross-linking reaction. In some alternatives, the hydrophobic content of the hydrogel prodrug is increased by addition of excess diacrylate. In some alternatives, the hydrophobic content of the hydrogel prodrug is increased by addition of excess diacrylate which can lead to a prolonged release of the drug.

Figure 12A:
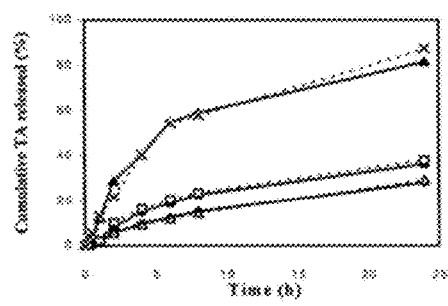
FIGS. 12A and 12B show a comparison of tranexamic acid release in a biological system in two existing delivery systems.
Figure 12B:
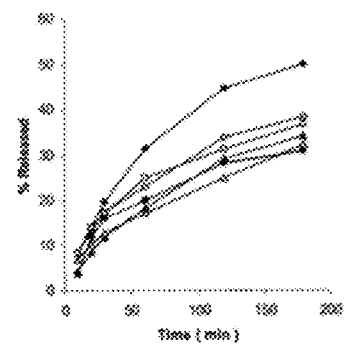

As shown in FIGS. 12A-12B, the two graphs, FIGS. 12A-12B show release of tranexamic acid using two delivery systems typical of those used in the market or in development today. Critical to note is that they appear more logarithmic than linear, indicating a gradual decrease in dosage level. FIG. 12A shows the leakage rates of tranexamic acid in an encapsulated liposome formulation over a 24 hour period (J Cosmet Sci. 2002 November-December; 53(6):375-86; included by reference in its entirety herein). FIG. 12B shows the release of tranexamic acid in an admixed hydrogel formulation in less than a 4 hour delivery time period (J Cosmet Sci. 2007; May-June; 58(3): 215-227; included by reference in its entirety herein). In both experiments, the two formulations rapidly approach a delivery level that is less than 100% of the drug in the delivery system sample. Both formulations release the drug slower and slower over time, indicating that the dose is changing. Neither of these studies demonstrated a 100% drug release, because the degradation time of the delivery system and drug release were not connected.

These types of problems are solved with the alternative hydrogel prodrugs described herein. In the alternatives provided, the hydrogel prodrug demonstrated control over longer term (weeks-months) drug-release kinetics. Ongoing experiments were focused on testing prolonged release (1-7 days) tranexamic acid hydrogels and extended release (1-2 weeks) formulations for each drug. As other drug candidates are fine-tuned, these can also be included in the manufacture of the hydrogel prodrug which is expected to have longer time-release kinetics as well.

In the alternative hydrogel prodrugs provided herein, the hydrogel prodrug showed a controlled release over an extended time period. The controlled release of the hydrogel prodrug was a zero-order controlled release. The control release of the hydrogel prodrug is important for maintaining constant and consistent drug levels in the target tissues or the cells of the subject that is being treated. As such, the controlled release allows the release of a drug into its environment at a rate that is constant even as the concentration of the drug in its environment decreases. In some alternatives, the extended period of time in which the drug is released is at least or equal to 3 days, 5 days, 7 days, 14 days, 30 days, 60 days, 120 days or 240 days or any number of days within a range in between any two aforementioned values. In some alternatives, the extended period of time is at least or equal to 3 days, 5 days, 7 days, 14 days, 30 days or 60 days or any number of days within a range in between any two aforementioned values.

The hydrogel prodrugs provided herein demonstrated proof of concept for longer-term (weeks to months) drug release. For example, hydrogel prodrugs were formulated to have prolonged release (1-7 days) for tranexamic acid. In some alternatives, the hydrogel prodrug is formulated to release tranexamic acid for at least or equal to 1, 2, 3, 4, 5, 6, or 7 days or any number of days in between a range defined by any two aforementioned values. Hydrogel prodrugs with tranexamic acid and mesalamine were also formulated to have sustained release (1-2 weeks). In some alternatives, the hydrogel prodrug is formulated to release tranexamic acid or mesalamine for at least or equal to 1, 2, 3, 4, 5, 6, 7, 8. 9. 10, 11, 12, 13 or 14 days or any number of days in between a range defined by any two aforementioned values. Further experimentation also indicated short term (hours) and prolonged (1-7 days) release for additional drug candidates. In some alternatives, the hydrophobic content of the hydrogel prodrug is increased by addition of excess diacrylate which can lead to a prolonged release of the drug.

The hydrogel prodrugs manufactured by the alternatives described demonstrated controlled biodegradation as well as controlled bioactivity. In some alternatives, the hydrogel prodrugs mass loss was correlated with the drug release indicating that the drug release was occurred concurrently with the bulk polymer degradation. Further experimentation showed that one could monitor molecular weights and identify chemical structure of the released species, which would allow one to characterize what forms the drug and polymer linkers are taking as they are released. Measurement of the bioactivity of the released drugs also proves that the drugs maintain their therapeutic qualities after being released from the hydrogel prodrug formulation.

Modified Geometry Development

The hydrogel prodrug of the alternatives described herein demonstrate a physical flexibility which will allow the drug to be tailored for specific applications that call for unique release durations. Modifying the geometry of the hydrogel prodrug can demonstrate that these hydrogel prodrugs can be made into any 3D shape. Without being limiting, these hydrogel prodrugs can be created into thin films that can be laid on top of wounds or at a surgical site such as wound dressings for delivery of multiple drugs. Similarly these thin strips can be modified into a form like Listerine Pocketpacks® strips which can be used for local antibiotic or pain-relief delivery after a dental or medical procedure. In some alternatives, the hydrogel prodrug can be in the form of a microparticle or an implant. The microparticles can be injectable into a variety of tissues, which the implants can be for subcutaneous use or as a surgical implant at a specific treatment site. In some alternatives, the hydrogel prodrug is a microparticle. In some alternatives, the microparticle is for injections. In some alternatives, the hydrogel prodrug is an implant. In some alternatives, a bioadhesive is used with the hydrogel prodrug or hydrogel prodrug system.

In some alternatives, excipients are used with the hydrogel prodrug or hydrogel prodrug system when they are used in injections, for example. In some alternatives, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, water, saline, dextrose, mannitol, lactose, lecithin, albumin, sodium glutamate, cysteine hydrochloride, and the like. In addition, if desired, the injectable pharmaceutical formulations can contain minor amounts of nontoxic auxiliary substances, such as wetting agents, pH buffering agents, and/or polyvinylpyrrolidone (PVP).

For injection, the hydrogel prodrugs can be formulated in solutions, preferably in physiologically compatible buffers such as Hanks' solution, Ringer's solution, or physiological saline buffer. For such transmucosal administration, penetrants appropriate to the barrier to be permeated are used with the system. Such penetrants are generally known in the art. Use of pharmaceutically acceptable carriers to formulate the ingredients herein disclosed for the practice of the invention into dosages suitable for systemic administration is within the scope of the invention. With proper choice of carrier and suitable manufacturing practice, the hydrogel prodrug disclosed herein, in particular, those formulated for intravenous injection of hydrogel prodrug microparticles.

Additionally, suspensions of the active ingredients can be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents that increase the solubility of the ingredients to allow for the preparation of highly concentrated solutions. In some alternatives, the vehicle for the hydrogel prodrug microparticles for injection comprises lipophilic solvent, fatty oil, organic oil, or liposome. In some alternatives, the vehicle is sesame oil, soybean, grapefruit or almond oils, or synthetic fatty acid esters, such as ethyl oleate or triglycerides, or liposomes.

The hydrogel prodrug can comprise a backbone that can support attachment of therapeutics and drugs. In some alternatives, the hydrogel prodrug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the hydrogel prodrug comprises a chemotherapeutic, an anti-viral, an anti-HIV antiviral, and anti-AIDS antiviral, pain medications, antibiotics, immunosuppressant, steroid, hormone, peptide, protein or an analgesic. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and tenofovir, valsartan, hydrochloraothiazide, lisdexamfetamine, mesalamine, memantine, pemetrexed, fingolimod, sitagliptin, metformin or darunavir.

In some alternatives, the hydrogel prodrug comprises pregabalin, glatiramer acetate, emtricitabine, sitagliptin, celecoxib, emtricitabine, sitagliptin, celecoxib, emtricitabine, tenofovir, valsartan, hydrochlorothiazide, lisdexamfetamine, memantine, pemetrexed, fingolimod, sitagliptin, metformin or darunavir. In some alternatives, the drug is for treatment of a neurological disorder, multiple sclerosis, diabetes, high blood pressure or Alzheimer's. In some alternatives, the hydrogel prodrug is an HIV antiviral, a Cox-2 inhibitor, a chemotherapeutic or a psychostimulant. In some alternatives, the hydrogel prodrug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir.

In some alternatives, the hydrogel prodrug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and tenofovir, valsartan, hydrochloraothiazide, lisdexamfetamine, mesalamine, memantine, pemetrexed, fingolimod, sitagliptin, metformin or darunavir. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid.

Formulations for Injection

The hydrogel polymers described herein can be used for injection of the drug into tissue in need of therapy, or as just an injectable drug. Hydrogel prodrugs can be ground into microparticles that are capable of being suspended in aqueous solutions and injected. As shown in FIG. 6, the microparticles can range in size from less than 10 microns to 200 to 300 microns in diameter. In some alternatives a hydrogel prodrug delivery system is provided. The hydrogel prodrug can be manufactured by anyone of the alternative methods described herein. In some alternatives, the hydrogel prodrug is ground into microparticles and is suspended in an aqueous solution for injection. In some alternatives, the microparticle comprises a diameter of at least or equal to 1, 5, 10, 20, 30, 40, 50, 60, 70, 80, 90, 100, 200 or 300 microns or any other diameter within a range defined by any two of the aforementioned values.

The microparticles can be prepared by wet grinding, high pressure homogenization and combinations thereof.

The manufacture of the injectable must meet sterile conditions which can include heat sterilization, chemical sterilization, filter sterilization and irradiation.

The microparticle can be prepared into an injectable formulation for the controlled release of the drug(s) into the surrounding tissue or media. The microparticles can then release the drug over an extended period of time in a manner to produce a constant level of drug in a subject. The microparticles are to be biodegradable and biocompatible.

The microparticles can be administered to a subject in need wherein the microparticles are suspended in an aqueous solution either by injection (intravenously, subcutaneously or intramuscularly). The aqueous solution can be a pharmaceutically acceptable suspending medium to suspend the microparticles. In some alternatives, the pharmaceutically acceptable suspending medium is sterile water, phosphate buffered saline, or a solution of carboxymethylcellulose. In some alternatives, the pharmaceutically acceptable medium comprises hyaluronic acid or derivative thereof. In some alternatives, the hyaluronic acid or derivative thereof is dissolved in physiological saline. In some alternatives, the pharmaceutically acceptable medium comprises an isotonic agent, and optionally, an anti-oxidant. In some alternatives the isotonic agent is sodium chloride or mannitol.

In some alternatives, the drug for injection within a hydrogel comprises nucleic acid analogues, tenofovir amino ester-based drugs, neurokinin 1 agonists, platinum-based amine-containing chemotherapeutics, anthracyclines, γ-aminobutyric acid-derived drugs, pregabalin, amino acid derivatives, aminated benzoic acid derivatives, proteins of any size, such as insulin or lysozyme, or antibodies or binding fragments thereof, such as IgG or binding fragments thereof or hormone derivatives.

In some alternatives, the drug for injection within a hydrogel is a cancer therapeutic.

Without being limiting, the drug categories which have been proven to be compatible with this new hydrogel prodrug technology for injection includes nucleic acid analogues such as the antiviral medications acyclovir, or ganciclovir, or tenofovir, amino ester-based drugs, such as the anesthetics procaine or benzocaine, neurokinin 1 agonists such as the antiemetic aprepitant, platinum-based, amine-containing chemotherapeutics such as cisplatin or oxaliplatin, anthracyclines such as doxorubicin, γ-aminobutyric acid-derived drugs such as the seizure and pain medications gabapentin or pregabalin, amino acid derivatives, such as the synthetic lysine derivative anti-hemorrhage drug tranexamic acid, aminated benzoic acid derivatives, such as the anti-inflammatory aspirin derivative 5-aminosalicylic acid, proteins of any size, such as insulin or lysozyme, antibodies or binding fragments thereof, such as IgG or a binding fragment thereof, and hormone derivatives, such as the synthetic thyroid hormone levothyroxine. In some alternatives of the hydrogel described herein, the drug is a nucleic acid analogue such as the antiviral medication acyclovir, or ganciclovir, and tenofovir amino ester-based drugs, such as the anesthetics procaine or benzocaine, neurokinin 1 agonists such as the antiemetic aprepitant, platinum-based, amine-containing chemotherapeutics such as cisplatin or oxaliplatin, anthracyclines such as doxorubicin, γ-aminobutyric acid-derived drugs such as the seizure and pain medications gabapentin or pregabalin, amino acid derivatives, such as the synthetic lysine derivative anti-hemorrhage drug tranexamic acid, aminated benzoic acid derivatives, such as the anti-inflammatory aspirin derivative 5-aminosalicylic acid, proteins of any size, such as insulin or lysozyme, antibodies or binding fragments thereof, such as IgG or binding fragments thereof or hormone derivatives, such as the synthetic thyroid hormone levothyroxine.

In some alternatives, the drugs for attachment to the hydrogel for injection are from general drug families including compounds containing a primary amine that are compatible with the hydrogel prodrug technology and may be delivered in a controlled manner using this technology. Without being limiting these drugs can include, antibiotics, amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones and fluoroquinolones, statins, steroids, sulfonamides, taxoides, tetracyclines, statins, chemotherapeutics, alkylating agents, platinum drugs, antimetabolites, cytotoxic antibiotics, topoisomerase inhibitors, mitotic inhibitors, corticosteroids, targeted enzyme inhibitors, antibody-drug conjugates, antibody fragments, protein fragments, oligopeptides, polypeptides, hormones, steroids, antipsychotics, anti-Alzheimers, cholesterol regulators, anesthetics, analgesics, antiepileptics, antivirals, anti-erectile dysfunction, anti-arthritic drug, contraceptives, diabetes medication, enzyme inhibitors, psychostimulants and/or platelet aggregation inhibitors. In some of the alternatives of the hydrogel herein, the drug is doxorubicin, procaine, insulin or acyclovir.

In some alternatives of the hydrogel for injection, the drug is an antibiotic. In some alternatives, the antibiotic is an amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones and fluoroquinolones, statins, steroids, sulfonamides, taxoides, and/or tetracyclines. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid.

Mold Casting of the Hydrogel Prodrug

Without being limiting, the hydrogel prodrug can be used in the form of an implant, sheet, film, support or a dressing. As shown in FIG. 5, the hydrogel prodrug can be molded into a desired shape depending upon its use. During the manufacture of the hydrogel prodrug, the at least one acrylate with the at least one primary amine group or at least two secondary amine groups of the at least one drug can be reacted to produce at least one polymer prodrug by a polymerization reaction. The polymer prodrug can then be placed in a mold for the cross-linking reaction. As shown in FIG. 5, the polymer prodrug was placed into a mold prior to cross-linking. Upon cross-linking, the polymer prodrug solidified into a flexible solid material, the hydrogel prodrug, in the shape of the mold. As shown, the polymer prodrugs were cast into microcentrifuge tubes, and the resulting hydrogel prodrugs seen here, made from tranexamic acid, retained the conical tube shape. These conical hydrogels were used for subsequent drug release studies. Alternatively, the hydrogel prodrugs could be ground in order to produce microparticles for injecting as shown in FIG. 6.

In some alternatives, the drug in the form of an implant, sheet, film, support or a dressing comprises nucleic acid analogues, tenofovir amino ester-based drugs, neurokinin 1 agonists, platinum-based amine-containing chemotherapeutics, anthracyclines, γ-aminobutyric acid-derived drugs, pregabalin, amino acid derivatives, aminated benzoic acid derivatives, proteins of any size, such as insulin or lysozyme, antibodies or binding fragments thereof, such as IgG or a binding fragment thereof or hormone derivatives.

In some alternatives, the drug in the form of an implant, sheet, film, support or a dressing is a cancer therapeutic.

In some alternatives, the hydrogel that is in the form of an implant, sheet, film, support or a dressing, comprises nucleic acid analogues such as the antiviral medications acyclovir, ganciclovir, tenofovir amino ester-based drugs, such as the anesthetics procaine or benzocaine, neurokinin 1 agonists such as the antiemetic aprepitant, platinum-based, amine-containing chemotherapeutics such as cisplatin or oxaliplatin, anthracyclines such as doxorubicin, γ-aminobutyric acid-derived drugs such as the seizure or pain medications gabapentin or pregabalin, amino acid derivatives, such as the synthetic lysine derivative anti-hemorrhage drug tranexamic acid, aminated benzoic acid derivatives, such as the anti-inflammatory aspirin derivative 5-aminosalicylic acid, proteins of any size, such as insulin or lysozyme, antibodies or binding fragments thereof, such as IgG or binding fragments thereof, and hormone derivatives, such as the synthetic thyroid hormone levothyroxine. In some alternatives of the hydrogel described herein, the drug is a nucleic acid analogues such as the antiviral medications acyclovir, ganciclovir, or tenofovir amino ester-based drugs, such as the anesthetics procaine or benzocaine, neurokinin 1 agonists such as the antiemetic aprepitant, platinum-based, amine-containing chemotherapeutics such as cisplatin or oxaliplatin, anthracyclines such as doxorubicin, γ-aminobutyric acid-derived drugs such as the seizure and pain medications gabapentin or pregabalin, amino acid derivatives, such as the synthetic lysine derivative anti-hemorrhage drug tranexamic acid, aminated benzoic acid derivatives, such as the anti-inflammatory aspirin derivative 5-aminosalicylic acid, proteins of any size, such as insulin or lysozyme, antibodies or binding fragments thereof, such as IgG or hormone derivatives, such as the synthetic thyroid hormone levothyroxine.

In some alternatives, the hydrogel that is in the form of an implant, sheet, film, support or a dressing comprises a drug selected from a general drug family, wherein the family consists of compounds containing a primary amine that are compatible with the hydrogel prodrug technology and may be delivered in a controlled manner using this technology. Without being limiting these drugs can include, antibiotics, amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones, fluoroquinolones, statins, steroids, sulfonamides, taxoides, tetracyclines, statins, chemotherapeutics, alkylating agents, platinum drugs, antimetabolites, cytotoxic antibiotics, topoisomerase inhibitors, mitotic inhibitors, corticosteroids, targeted enzyme inhibitors, antibody-drug conjugates, antibody fragments, protein fragments, oligopeptides, polypeptides, hormones, steroids, antipsychotics, anti-Alzheimers, cholesterol regulators, anesthetics, analgesics, antiepileptics, antivirals, anti-erectile dysfunction, anti-arthritic drug, contraceptives, diabetes medication, enzyme inhibitors, psychostimulants, or platelet aggregation inhibitors. In some of the alternatives of the hydrogel herein, the drug is doxorubicin, procaine, insulin or acyclovir.

In some alternatives of the hydrogel, the drug is an antibiotic. In some alternatives, the antibiotic is an amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones and fluoroquinolones, statins, steroids, sulfonamides, taxoides, or tetracyclines. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the drug is a protein, such as insulin or lysozyme.

Overview of the Synthesis Procedure

The drug-containing hydrogels, hydrogel prodrugs, can be created using two main steps.

For synthesizing the polymer prodrug, a drug that has at least one free primary amine group or at least two secondary amine groups is provided. A diacrylate is also provided. In the first step, a liquid polymer (polymer prodrug) is created from a reaction between the amine(s) and diacrylate(s). In the alternatives described herein, the amine(s) is from at least one primary amine or at least two secondary amines within the drug(s). In the alternatives described herein, a linear polymer is formed which follows the chemical sequence: ~Diacrylate-amine-diacrylate-amine-diacrylate~, etc. If multiple diacrylates and/or multiple amines are included in the synthesis reaction, then any of the diacrylate or amine components can occupy the appropriate position on the chain. The primary amine group of the drug can participate directly in the condensation reaction with two diacrylates, resulting in a polymer containing the drug within its backbone, such that the drug is part of the backbone. During the reaction, the amine acts as the linker between diacrylate species. The reaction can be prepared using a molar excess of diacrylate, resulting in acrylate-terminated polymers. A 1.2:1 molar ratio of diacrylate:amine can be used, although conceivably any ratio exceeding 1:1 would create acrylate-terminated polymers. In some alternatives described herein, at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values.

This first step results in a polymer (usually a viscous liquid) belonging to the class of poly(beta amino ester)s (PBAEs). PBAEs have been studied primarily as a means of delivering DNA in a liquid carrier formulation, but they can also be cross-linked. An example of a PBAE structure is shown in FIG. 3.

In a second step, the polymer prodrug, which can be in a liquid form, can be cross-linked using a free radical initiator, causing the free acrylate end groups of the polymer to form carbon-carbon single bond cross-links. This is a standard curing process used in many commercial polymer systems. The reason excess diacrylate is used in the synthesis reaction is to take advantage of these terminal carbon-carbon double bonds that can participate in the cross-linking step. In some alternatives, the polymer prodrug has free acrylate end groups, wherein the acrylate end groups participate in cross-linking steps.

The resulting hydrogel prodrugs can then degrade due to hydrolysis of ester bonds in the polymer backbone. The drug can be liberated from the hydrogel prodrug once the molecular weight is reduced enough to allow drug, or drug-containing oligomers, to become soluble. Because the drug release from the hydrogel prodrug is dependent on degradation, henceforth "degradation" and drug "release" can be used interchangeably.

Chemical Components of Some Alternative Hydrogel Prodrugs

In some alternatives, the working formulation can contain Diacrylate 1, comprising Poly(ethylene glycol) 400 diacrylate (PEG400DA) or diethylene glycol diacrylate (DEGDA). Conceivably, any biocompatible diacrylate of sufficiently low molecular weight to be cleared from the body can be utilized. Such diacrylates may range from a molecular weight as low as 160 g/mol to as high as 1,000 g/mol. In some alternatives, the molecular weight of the diacrylate comprises a weight of 160 g/mol, 200 g/mol, 250 g/mol, 300 g/mol, 350 g/mol, 400 g/mol, 450 g/mol, 500 g/mol, 550 g/mol, 600 g/mol, 650 g/mol, 700 g/mol, 750 g/mol, 800 g/mol, 850 g/mol, 900 g/mol, 950 g/mol or 1000 g/mol, or any amount in g/mol within a range defined by any two of the aforementioned values. Dimethacrylates can also be used.

In some alternatives, the properties of the components, such as molecular weight, hydrophilicity, steric factors, for example, can be primarily responsible for the degradation rate of the polymer. For example, PEG400DA polymers can degrade more rapidly (hours) than DEGDA polymers (>6 months). In some alternatives, hydrogel prodrugs made from PEG400DA can degrade completely within 4, 5, 6, 7, 8, 9 or 10 hours or any amount of time within a range defined by any two aforementioned values.

In some alternatives, a drug containing a primary amine is used in the synthesis of the hydrogel prodrug. In some alternatives, the drug comprises acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. The amine in the drug can act as the linker between diacrylate species. As such, this component contributes (generally to a smaller degree than the diacrylate) to the degradation rate of the polymer. For example, in formulations containing PEG400DA and isobutylamine (Amine 2, a non-drug primary amine that is used to serve as a spacer to reduce steric hindrance from Amine 1), hydrogels made with tranexamic acid as Amine 1 (a drug containing a primary amine) degrade in approximately 4 hours, while hydrogels made with 5-aminosalicylic acid as Amine 1 degrade in approximately 10 hours.

Amine 2 (optional, depending on steric hindrance of Amine 1) as described herein, is a non-drug primary amine that serves as a spacer to reduce steric hindrance from Amine 1. A non-drug primary amine that serves as a spacer to reduce steric hindrance is typically attached to a small linear hydrocarbon chain with few or no bulky groups or branches attached. This amine can modify the degradation rate. Amines attached to linear hydrocarbons with no branches lead to faster degradation than amines attached to branched or bulky groups. In some alternatives described herein, the hydrogel prodrug comprises spacers, wherein the spacers are derived from a non-drug primary amine that serves as a spacer to reduce steric hindrance from a drug that is covalently linked through an amine group to the hydrogel prodrug polymers.

A second diacrylate can also be used in the polymerization reaction. This second diacrylate can be used to modify the degradation rate of the hydrogel. In some exemplary alternatives, hydrogels containing tranexamic acid and containing a 2:1 ratio of DEGDA:PEG400DA degrade in approximately 19 hours, and hydrogels containing 5-aminosalicylic acid and containing a 2:1 ratio of DEGDA:PEG400DA degrade in approximately 50 hours. These degradation times are approximately 5 times longer than hydrogels made using only PEG400DA.

Manufacture (Synthesis) of a Hydrogel Prodrug

Drugs containing at least one free primary amine or at least two secondary amines can be incorporated into a polymer prodrug used in cross-linking into a hydrogel prodrug. The drug can be in an aqueous form or in a solid form. If drug is a solid, the drug is dissolved in appropriate solvent. The solvent for use should be miscible with the other diacrylate and amine components.

Some drugs are directly soluble in the liquid amine. In this case, no additional solvent is required. For some drugs, the solvent of choice is water. Optionally, the aqueous solution can comprise PBAE.

During the synthesis reaction of the polymer prodrug, the water component is evaporated during the synthesis reaction due to the high temperature (if the reaction vessel is not sealed airtight), or evaporated immediately following the synthesis reaction. Otherwise, residual water can cause hydrolysis of the polymer. Use of water in the reactions however is important as it can allow many drugs that have been reported to be non-compatible with this reaction for due to their poor solubility in organic solution. Surprisingly, the use of water did not cause degradation and allowed the incorporation of drugs into the hydrogel polymer. In some alternatives of manufacturing the hydrogel prodrug, water is used as a solvent to dissolve the drug or prodrug.

Prior to the synthesis reaction, some drugs are dissolved in an aqueous solution containing organic solvents. Without being limiting, examples of organic solvents can include ethanol or methanol, which can also be evaporated from the formulation following synthesis of the polymer.

Additionally, organic solvents with low volatility, such as dimethyl sulfoxide (DMSO), can be extracted using standard techniques such as lyophilization, dialysis, or affinity precipitation after synthesis, or they can be removed using similar techniques after cross-linking of the polymer into a hydrogel.

After dissolving the drug, the components (all diacrylates and amines, including drug or drug solution) are all mixed in a flask and heated to the appropriate temperature (typically 50-90 C) under constant stirring. The temperature can be at least or equal to 50° C., 55° C., 60° C., 65° C., 70° C., 75° C., 80° C., 85° C. or 90° C. or any other temperature within a range defined by any two of the aforementioned values.

The reaction is then allowed to proceed to completion ("completion" is typically defined as a desired molecular weight as determined by GPC, or as the conversion of carbon-carbon double bonds to a certain percentage (typically 90%+) as determined by FTIR). The reaction typically takes 8-72 hours to complete, with lower temperatures requiring longer reaction times. In some alternatives, the reaction is allowed to proceed for 7, 8, 9, 10, 12, 24, 36, 48, 60 or 72 hours or any amount of time within a range defined by any two of the aforementioned values. The drug or the solvent may necessitate temperatures at the low end of this range, and thus, longer reaction times. Different amines and diacrylates can also require specific reaction times to reach completion.

In some alternatives, visual appearance of the reacted polymers can be used to determine the completion of the reaction. For example, successfully reacted polymers can be homogeneous in appearance, with a color characteristic of the drug. For example, 5-aminosalicylic acid polymers are purple-brown, tranexamic acid polymers are yellow, and doxorubicin polymers are purple. In some alternatives, the reacted polymers become a viscous liquid which has a consistency similar to honey. However, if the drug or polymer is dissolved in a solvent, such as DMSO, which does not evaporate out, it will reduce the viscosity of the polymer.

In order to quench the reaction, the polymer prodrug can also be cooled and stored at 4° C.

After completion of the reaction, the polymer prodrugs are prepared for cross-linking into flexible solids (hydrogel prodrug). Chemical cross-linking is accomplished by adding a free radical initiator such as ammonium persulfate, and optionally adding a catalyst, such as Tetramethylethylenediamine (TEMED). 1-10% w/w APS relative to polymer mass can be used with 1-10% w/w TEMED. In some alternatives described herein, 1%, 2%, 3%, 4%, 5%, 6%, 7%, 8%, 9% or 10% w/w APS relative to polymer mass is used or any percent w/w APS within a range defined by any two of the aforementioned values is used in the cross-linking reaction. In some alternatives described herein, 1%, 2%, 3%, 4%, 5%, 6%, 7%, 8%, 9% or 10% w/w TEMED relative to polymer mass is used or any percent w/w TEMED within a range defined by any two of the aforementioned values is used in the cross-linking reaction. The chemical cross-linking can be allowed to proceed overnight (6-12 hours). Some chemical cross-linking reactions require 48 hours to completely cross-link. In some alternatives, the chemical cross-linking is allowed to proceed for at least or equal to 1, 2, 3, 4, 5, 6, 7, 7, 8, 9, 10, 12, 14, 16, 18, 20, 22, 24, 26, 28, 30, 32, 34, 36, 38, 40, 42, 44, 46 or 48 hours or any number of hours within a range defined by any two of the aforementioned values. In the case in which the polymer prodrug is a liquid, the polymer prodrug can be cast within a mold in which the cross-linking reaction can occur to produce a desired shape of the hydrogel prodrug when solidified.

In some alternatives, the cross-linking can be performed by photocross-linking. Photocross-linking can be accomplished by adding a light-activated free radical initiator (photoinitiator). A photoinitiator is any chemical compound that decomposes into free radicals when exposed to light. Examples of photoinitiators can include but is not limited to Azobisisobutyronitrile (AIBN), benzoyl peroxide, 2,2-dimethoxy-2-phenylacetophenone (DMPA), polyethlene glycol diacrylate (PEGDA), trimethylolpropane triacrylate (TPT), acryloyl chloride and camphorquinone. In some alternatives, the cross-linking is performed by photocross-linking with a photoinitiator or light-activated free radical initiator. In some alternatives the photoinitiator or light-activated free radical initiator is Azobisisobutyronitrile (AIBN), benzoyl peroxide, 2,2-dimethoxy-2-phenylacetophenone (DMPA), polyelthene glycol diacrylate (PEGDA), trimethylolpropane triacrylate (TPT), acryloyl chloride or camphorquinone. In some alternatives, the light-activated free radical initiator is DMPA. In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, 1% w/w DMPA is used. Brief (1-10 minutes) exposure to UV light results in complete cross-linking. In some alternatives, the cross-linking reaction is performed under UV radiation for at least or equal to 1, 2, 3, 4, 5, 6, 7, 8, 9 or 10 minutes or any time within a range defined by any two of the aforementioned values.

Photocross-linking is more rapid than chemical cross-linking, and can be used on thin, translucent materials. If the UV light cannot penetrate deep enough into the material, this can result in heterogeneous cross-linking in which the surface is cross-linked, while the underlying material is not.

After completion of the cross-linking step, the hydrogel prodrug can be immersed in a solvent such as ethanol to remove any unreacted components. The hydrogel prodrug can then be dried and stored at room temperature with desiccant. It is important to keep the hydrogel prodrug dry, as an aqueous environment will hydrolytically degrade the hydrogel prodrug at a rate determined primarily by the chemical composition of the hydrogel.

When the hydrogel prodrug is in an aqueous solution, the hydrogel prodrug can visibly swell and become more translucent as they retain water, and gradually collapse into wisps of material that disappear. The disappearance of material has been observed to coincide with the completion of drug release.

In some alternatives, the hydrogel prodrug can be manufactured in a 3D printer. A 3D printer can be used to synthesize a 3D object, of any shape or geometry. In some alternatives herein, the cross-linking step in the manufacturing of the hydrogel prodrug is performed within a 3D printer. Without being limiting 3D printing of drugs can be used to create a capsule to be swallowed or an implant that is made into a desired shape. In some alternatives, the hydrogel prodrug is manufactured in a 3D printer in which the hydrogel prodrug is an antibiotic implant, an antibiotic formulation or a hydrogel prodrug comprising an analgesic. In some alternatives, the hydrogel prodrug comprises a drug wherein the drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an antiviral, an analgesic, an antibiotic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the drug is a protein. In some alternatives, the protein comprises insulin or lysozyme.

In some alternatives, the method of making the hydrogel prodrug comprises manufacturing the polymer prodrug, placing the polymer prodrug within a 3D printer and cross linking the polymer prodrug within the 3D-printer thereby producing the hydrogel prodrug and printing the hydrogel prodrug into a desired shape by the 3D printer. In some alternatives, a light source is used in the cross-linking step. In some alternatives, the 3D printing method is performed within an enclosed chamber. In some alternatives, the 3D printing is controlled by a computer program. Without being limiting, examples of commercially available 3D printers includes Objet260Connex™, Objet260 Connexl™ and Objet 260Connex3™.

Physical Forms of the Hydrogels

Without being limiting, the liquid polymer can be cast into any shape, the geometry of the hydrogels can be tailored to the desired application. These materials are soft and flexible, and can be compressed or stretched considerably before they tear. By way of example, and not of limitation, a hydrogel can be in the form of a thin film, a pill, microparticles, nano-particles, capsules, implantable rods or discs or a capsule. Implantable rods are envisioned to be similar in form to Nexplanon which is a rod containing progesterone and is used as a birth control implant for women.

For example, a thin film can be created that can be applied onto a large surface area. This is envisioned to be similar in form to a Listerine® strip, in which the hydrogel prodrug strip can contain antibiotics or anti-inflammatory drugs, which can be applied by a dentist onto the gumline during cleaning procedures to clear up an infection.

Alternatively, the thin films containing tranexamic acid (an anti-hemorrhage drug) can be layered onto a bandage, which can be applied to a battlefield wound by a field medic to prevent subjects from bleeding out.

The same tranexamic acid hydrogel could also be packed into a wound to mechanically staunch the bleeding and pharmaceutically prevent further bleeding.

The same tranexamic hydrogel could be processed into micro- or nanoparticles (this can be done mechanically by grinding, or can be done during the hydrogel synthesis by performing the cross-linking reaction in an excess of solvent) and introduced in a variety of ways: injected into tissue as a suspension, coated onto medical equipment to be released at the site of treatment, coated onto a bandage and applied similarly to the thin film, or other methods of treatments that are known to one skilled in the art.

The 5-aminosalicylic acid hydrogel can also be processed into any of the previously mentioned forms.

Any of these hydrogels can be formulated into oral tablets; the hydrogel may be processed into particles, or a solid capsule (likely with a common coating to mediate exposure to the acidic digestive environment), and taken orally to provide sustained systemic drug release.

In some alternatives, a hydrogel prodrug comprising a chemotherapeutic can be injected as particles directly into or onto a tumor, or a solid implant can be placed subcutaneously or at the site of the tumor to provide sustained chemotherapeutic release.

Additionally, in some alternatives, an un-cross-linked drug polymer can also be applied in novel ways, such as in an injection or in a wound treatment. In some alternatives, a bioadhesive is used with the hydrogel prodrug or hydrogel prodrug system.

Reaction Schemes

Figure 14:
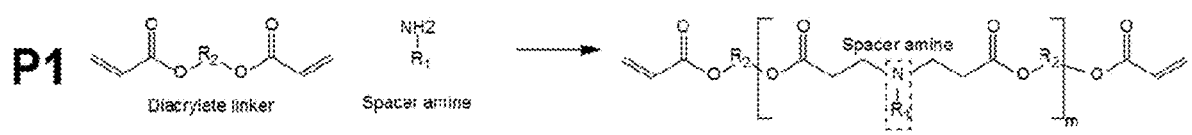
FIG. 14 shows reaction scheme P1, involving at least one diacrylate linker and a non-drug (spacer) amine.

Provided herein are methods that may be used to prepare the hydrogels described in the instant application. In one alternative, a drug-free hydrogel may be prepared according to reaction scheme P1 as shown in FIG. 14. Reaction scheme P1 shows the reaction between at least one diacrylate linker and a spacer having one primary amine moiety to form a polymeric compound via conjugate addition of the amine to the β-carbon of the α,β-unsaturated carbonyl moiety of the acrylate. In some alternatives, the primary amine spacer may be replaced with a spacer that contains more than one secondary amine moiety.

Figure 16:
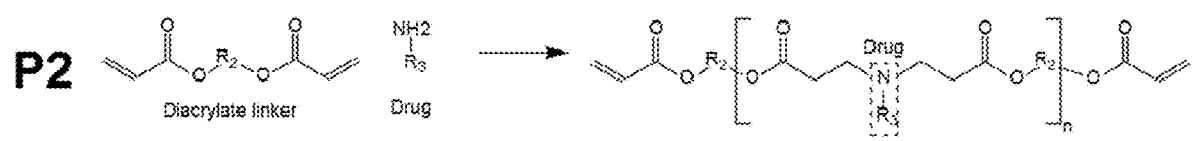
FIG. 16 shows reaction scheme P2, involving at least one diacrylate linker and at least one drug.

In some alternatives, a hydrogel prodrug may be prepared according to reaction scheme P2 as shown in FIG. 16. Reaction scheme P2 shows the reaction between at least one diacrylate linker and a drug compound having one primary amine moiety to form a polymeric compound via conjugate addition of the amine to the β-carbon of the α,β-unsaturated carbonyl moiety of the acrylate. In some alternatives, the drug compound may be a drug compound that contains more than one secondary amine moiety.

Figure 15:
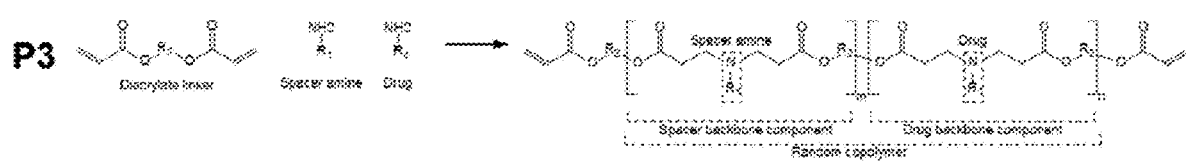
FIG. 15 shows reaction scheme P3, involving at least one diacrylate linker and one drug.

In some alternatives, a hydrogel prodrug may be prepared according to reaction scheme P3 as shown in FIG. 15. Reaction scheme P3 shows the reaction between at least one diacrylate linker and a mixture of a spacer compound having one primary amine moiety and a drug compound having one primary amine moiety to form a polymeric compound via conjugate addition of the amine of the spacer and/or drug to the β-carbon of the α,β-unsaturated carbonyl moiety of the acrylate. The resulting product is a random copolymer having both a spacer backbone component and a drug backbone component. In some embodiments, the properties of the hydrogels produced according to FIG. 15 is dependent of the ratio of spacer compound to drug compound used. In some alternatives, the spacer compound may contain more than one secondary amine moiety. In some alternatives, the drug compound may contain more than one secondary amine moiety. In some alternatives, the drug compound and spacer compound may both contain one primary amine moiety. In some alternatives, the drug compound and spacer compound may both contain more than one secondary amine moiety. In some alternatives, the drug compound may contain one primary amine moiety and the spacer compound may contain more than one secondary amine moiety. In some alternatives, the spacer compound may contain one primary amine moiety and the drug compound may contain more than one secondary amine moiety.

Figure 17:
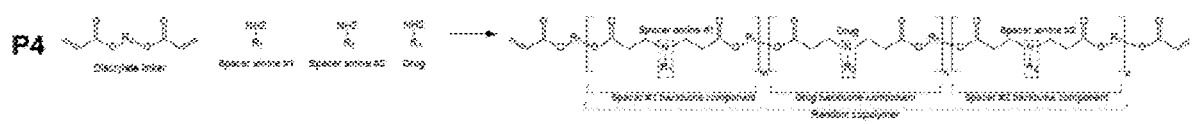
FIG. 17 shows reaction scheme P4, involving at least one diacrylate linker and at least two non-drug spacer amines and at least one drug.

In some alternatives, a hydrogel prodrug may be prepared according to reaction scheme P4 as shown in FIG. 17. Reaction scheme P4 shows the reaction between at least one diacrylate linker and a mixture of two or more different spacer compounds each having one primary amine moiety and a drug compound having one primary amine moiety to form a polymeric compound via conjugate addition of the amine of the spacers and/or drug to the β-carbon of the α,β-unsaturated carbonyl moiety of the acrylate. The resulting product is a random copolymer having both a spacer backbone components derived from each of the different spacer compounds and a drug backbone component. In some embodiments, the properties of the hydrogels produced according to FIG. 17 are dependent of the ratio of spacer compound to drug compound used.

Figure 18:
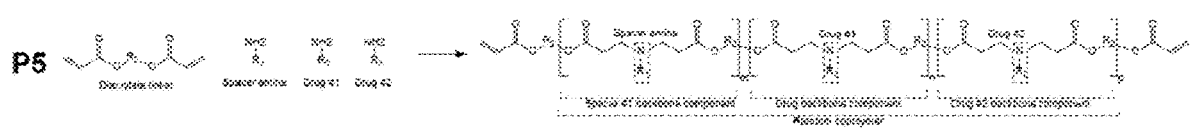
FIG. 18 shows reaction scheme P5, involving at least one diacrylate linker and at least one non-drug spacer amine and at least two drugs.

In some alternatives, a hydrogel prodrug may be prepared according to reaction scheme P5 as shown in FIG. 18. Reaction scheme P5 shows the reaction between at least one diacrylate linker and a mixture of a spacer compound having one primary amine moiety and a mixture of two or more drug compound having one primary amine moiety to form a polymeric compound via conjugate addition of the amine of the spacer and/or drugs to the β-carbon of the α,β-unsaturated carbonyl moiety of the acrylate. The resulting product is a random copolymer having a spacer backbone component and a drug backbone component derived from each of the different spacer compounds. In some embodiments, the properties of the hydrogels produced according to FIG. 18 are dependent of the ratio of spacer compound to drug compounds used. In some alternatives, the spacer compound may contain more than one secondary amine moiety. In some alternatives, each of the drug compounds may independently contain more than one secondary amine moiety. In some alternatives, each of the drug compounds and the spacer compound may independently contain one primary amine moiety. In some alternatives, each of drug compounds may be a small molecule drug. In some alternatives, each of drug compounds may be a large molecule drug (e.g., IgG or a binding fragment thereof). In some alternatives, one of the drug compounds may be a small molecule drug and the remaining drug compounds may be large molecule drugs. In some alternatives, a hydrogel prodrug prepared according to reaction scheme P5 may release to different drugs. In some alternatives, a hydrogel prodrug prepared according to reaction scheme P5 may release two or more or a plurality of different drugs. In some alternatives, a hydrogel prodrug prepared according to reaction scheme P5 may release three different drugs. In some alternatives, a hydrogel prodrug prepared according to reaction scheme P5 may release more than three different drugs.

Figure 19:
FIG. 19 shows reaction scheme P6, involving at least two diacrylate linkers and at least one non-drug spacer amine and at least one drug.

In some alternatives, a hydrogel prodrug may be prepared according to reaction scheme P6 as shown in FIG. 19. Reaction scheme P6 shows the reaction between at least two diacrylate linkers and at least one non-drug spacer having a primary amine moiety and at least one drug having a primary amine moiety to form a polymeric compound via conjugate addition of the amine of the spacer and/or drug to the β-carbon of the α,β-unsaturated carbonyl moiety of the acrylate linkers. The resulting product is a random copolymer having spacer backbone components derived from each of the different spacers and a drug backbone component derived from the drug compound. Preparation of a hydrogel prodrug according to reaction scheme P6 may allow further control over the degradation kinetics and physical properties of the hydrogel prodrugs. For example, in some alternatives, preparation of a hydrogel prodrug according to reaction scheme P6 may result in a hydrogel prodrug with an extended lifespan as compared to a hydrogel prodrug prepared using an alternative preparation. In some embodiments, the properties of the hydrogels produced according to FIG. 19 are dependent of the ratio of spacer compound to drug compounds used. In some embodiments, the properties of the hydrogels produced according to FIG. 19 are dependent of the ratio of different diacrylate linkers used. In some alternatives, the spacer compound may contain more than one secondary amine moiety. In some alternatives, the drug compound may contain more than one secondary amine moiety. In some alternatives, each of the drug compound and the spacer compound may independently contain one primary amine moiety. In some alternatives, the drug compound may contain more than one secondary amine moiety and the spacer compound may contain a primary amine moiety. In some alternatives, the spacer compound may contain more than one secondary amine moiety and the drug compound may contain a primary amine moiety.

Figure 20:
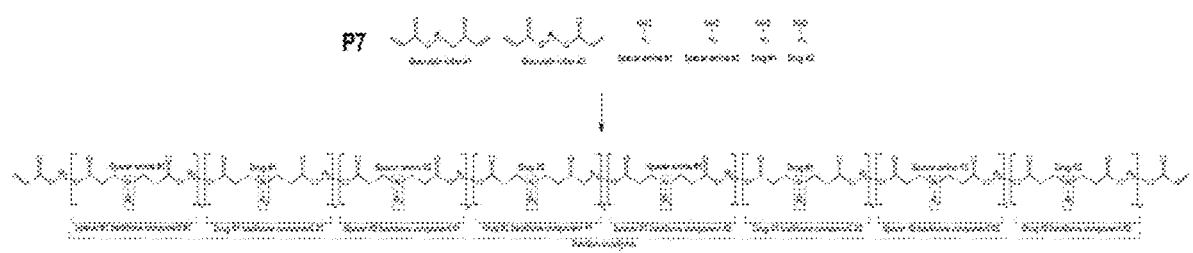
FIG. 20 shows reaction scheme P7, involving at least two diacrylate linkers and at least two spacer amines and at least two drugs.

In some alternatives, a hydrogel prodrug may be prepared according to reaction scheme P7 as shown in FIG. 20. Reaction scheme P7 shows the reaction between at least two diacrylate linkers and at least two non-drug spacers having a primary amine moiety and at least two drug compounds having a primary amine moiety to form a polymeric compound via conjugate addition of the amine moiety of the spacer and/or drug to the β-carbon of the α,β-unsaturated carbonyl moiety of the acrylate linkers. The resulting product is a random copolymer having the general structure shown in FIG. 20. Reaction scheme P7 is a generalized combination of schemes P4, P5, and P6, and allows any combination of two or more diacrylates, and/or two or more drugs and/or two or more drug spacers.

In some alternatives, the polymeric compounds prepared using any of the reactions schemes described herein may be further modified using chemical methods known in the art. For example, polymeric compounds formed using any one of reaction schemes P1-P7 may be crosslinked using methods including, but not limited to, those described herein.

Drug Release Studies

All drug release studies were performed by immersing 50-200 mg of hydrogel prodrug samples in 5-10 mL deionized water on an orbital shaker and periodically collecting 1 mL samples, with replacement. Spectra of both polymer prodrugs and fully degraded hydrogel prodrug samples were used to identify peaks that correlated to drug concentrations. Background absorbance values were subtracted using a drug-free hydrogel control, and the background-subtracted absorbance values were corrected for the sampling volume replaced at each time point.

All drug release graphs show the cumulative total of drug released expressed as a fraction (Mt/M∞, here labeled as the cumulative fraction) as a function of time, in hours.

Using reaction scheme P3 (FIG. 15), hydrogel prodrugs were created using poly(ethylene glycol 575) diacrylate as the diacrylate and isobutylamine as the spacer amine to create hydrogels that fully degraded in a matter of hours. The same formulations were then modified using reaction scheme P6 by replacing a fraction of the diacrylate moles with an equal molar amount of diethylene glycol diacrylate, creating hydrogel prodrugs that degraded fully over the course of days to weeks. All formulations utilized an isobutylamine:drug ratio between 9:1 and 99:1. In some alternatives, formulations utilize an isobutylamine:drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios.

All formulations produced generally linear release kinetics from the beginning of the experiment until the complete degradation of the material, with some exceptions. Doxorubicin, for all formulations, exhibited a lag period where minimal drug release occurred, followed by a linear release period. This lag period ranged from hours to days, depending on the formulation. All other formulations released drug steadily for the duration of their lifespans. Procaine and acyclovir each had certain formulations that appeared to produce biphasic release, with an initial high linear release rate and a subsequent lower linear release rate for the remainder of the release period. This effect was not present in acyclovir P3, but was seen in acyclovir P6. It is known that synthesis parameters, including reaction temperature, reaction duration, and reactant concentration, as well as other factors such as post-reaction washing and drying of the hydrogels, can modulate the release kinetics and, in particular, they may modulate the initial drug release behavior. It is notable that none of the formulations exhibited an appreciable initial burst release, which is a characteristic of most currently available drug delivery systems and is often a negative aspect of these systems that must be overcome to obtain desirable release kinetics. It is also important that the completion of drug release coincides with the complete disappearance of visible hydrogel material, indicating that material degradation does not occur without drug release, and conversely, drug release does not occur without material degradation.

All large molecules tested, ranging in size from small (insulin, 5.8 kDa) medium (lysozyme, 14.3 kDa) to large (IgG, 158 kDa) exhibited near-perfect linear release kinetics with zero burst for release periods ranging from hours to days, suggesting that this technology is particularly well-suited for delivery of large molecule and antibody drugs. In some alternatives, the molecules for use as a drug are 1, 5, 10, 20, 40, 60, 120, 240, 360 or 500 kDa or any other molecular weight in a range in between any two aforementioned values. As discussed, the advantage of this type of release would be the steady concentration of drug in a subject that is being treated. In the alternatives described herein, the hydrogel prodrug can be manufactured by any one of the reaction schemes provided herein.

Without being limiting, the drug categories, which have been proven to be compatible with this new hydrogel prodrug technology include nucleic acid analogues such as the antiviral medications acyclovir, ganciclovir, tenofovir amino ester-based drugs, such as the anesthetics procaine or benzocaine, neurokinin 1 agonists such as the antiemetic aprepitant, platinum-based, amine-containing chemotherapeutics such as cisplatin or oxaliplatin, anthracyclines such as doxorubicin, γ-aminobutyric acid-derived drugs such as the seizure and pain medications gabapentin or pregabalin, amino acid derivatives, such as the synthetic lysine derivative anti-hemorrhage drug tranexamic acid, aminated benzoic acid derivatives, such as the anti-inflammatory aspirin derivative 5-aminosalicylic acid, proteins of any size, such as insulin or lysozyme, antibodies or binding fragments thereof, such as IgG or binding fragments thereof, and hormone derivatives, such as the synthetic thyroid hormone levothyroxine. In some alternatives of the hydrogel described herein, the drug is a nucleic acid analogue such as the antiviral medication acyclovir, ganciclovir, or tenofovir amino ester-based drugs, such as the anesthetics procaine or benzocaine, neurokinin 1 agonists such as the antiemetic aprepitant, platinum-based, amine-containing chemotherapeutics such as cisplatin or oxaliplatin, anthracyclines such as doxorubicin, γ-aminobutyric acid-derived drugs such as the seizure and pain medications gabapentin or pregabalin, amino acid derivatives, such as the synthetic lysine derivative anti-hemorrhage drug tranexamic acid, aminated benzoic acid derivatives, such as the anti-inflammatory aspirin derivative 5-aminosalicylic acid, proteins of any size, such as insulin or lysozyme, antibodies or binding fragments thereof, such as IgG or hormone derivatives, such as the synthetic thyroid hormone levothyroxine.

In some alternatives, the drugs for attachment to the hydrogel are from general drug families including compounds containing a primary amine that are compatible with the hydrogel prodrug technology and may be delivered in a controlled manner using this technology. Without being limiting these drugs can include, antibiotics, amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones and fluoroquinolones, statins, steroids, sulfonamides, taxoides, tetracyclines, statins, chemotherapeutics, alkylating agents, platinum drugs, antimetabolites, cytotoxic antibiotics, topoisomerase inhibitors, mitotic inhibitors, corticosteroids, targeted enzyme inhibitors, antibody-drug conjugates, antibody fragments, protein fragments, oligopeptides, polypeptides, hormones, steroids, antipsychotics, anti-Alzheimers, cholesterol regulators, anesthetics, analgesics, antiepileptics, antivirals, anti-erectile dysfunction, anti-arthritic drug, contraceptives, diabetes medication, enzyme inhibitors, psychostimulants and/or platelet aggregation inhibitors. In some of the alternatives of the hydrogel herein, the drug is doxorubicin, procaine, insulin or acyclovir.

In some alternatives of the hydrogel, the drug is an antibiotic. In some alternatives, the antibiotic is an amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones and fluoroquinolones, statins, steroids, sulfonamides, taxoides, or tetracyclines. In some alternatives, the drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an antiviral, an analgesic, an antibiotic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the drug is a protein. In some alternatives, the protein comprises insulin or lysozyme.

Any drug containing an available primary or multiple secondary amines, or any drug that can be aminated, is likely to be compatible within this system. For each drug, the functionality of the drug delivery system will depend on the choice of diacrylate or diacrylates, spacer amine or spacer amines, and/or concentrations thereof.

In some alternatives, a drug can be modified to add a functional group such as adding a linker with an amine group so that a drug without an accessible amine can be added to a hydrogel. Amination is a process by which an amine group is introduced into a molecule and can be appreciated by those of skill in the art.

Drug Release Study Summary Table

Provided below is a table that summarizes the drug release studies performed (Table 1).

TABLE 1

Summary of drug release studies. DA1:DA2 is the molar ratio of poly(ethylene glycol 575) diacrylate to diethylene glycol diacrylate. The crosslink method indicates whether the crosslinking process is chemically-initiated, photo initiated using UV light, or whether the material self-crosslinked. The reaction scheme refers to schemes P1-P7 defined previously.

| Study Code | Drug | DA1:DA2 | Crosslink method | Reaction scheme | $t_{100}$ |
|---|---|---|---|---|---|
| VR002 | Acyclovir | 1:0 | Chemical | P3 | 10 |
| VR023 | Acyclovir | 1:2 | Chemical | P6 | 80 |
| VR009 | Aprepitant | 1:0 | Chemical | P3 | 10 |
| VR027 | Aprepitant | 1:2 | Chemical | P6 | 75 |
| VR032 | Benzocaine | 1:2 | Chemical | P6 | 300 |

TABLE 1-continued

Summary of drug release studies. DA1:DA2 is the molar ratio of poly(ethylene glycol 575) diacrylate to diethylene glycol diacrylate. The crosslink method indicates whether the crosslinking process is chemically-initiated, photo initiated using UV light, or whether the material self-crosslinked. The reaction scheme refers to schemes P1-P7 defined previously.

| Study Code | Drug | DA1:DA2 | Crosslink method | Reaction scheme | $t_{100}$ |
|---|---|---|---|---|---|
| VR013 | Cisplatin | 1:0 | Chemical | P3 | 10 |
| VR034 | Cisplatin | 1:2 | Chemical | P6 | 150 |
| VR011 | Doxorubicin | 1:0 | None; self-crosslinked | P3 | 4 |
| VR026 | Doxorubicin | 1:4 | None; self-crosslinked | P6 | 250 |
| VR028 | Doxorubicin | 1:6 | None; self-crosslinked | P6 | 600 |
| VR014 | Gabapentin | 1:0 | Chemical | P3 | 7 |
| VR015 | Gabapentin | 1:0 | Chemical | P3 | 8 |
| VR019 | Ganciclovir | 1:0 | Chemical | P3 | 6 |
| VR036 | IgG | 1:0 | Chemical | P3 | 10 |
| VR038 | IgG | 1:1 | Chemical | P6 | 48 |
| VR010 | Insulin | 1:2 | Chemical | P6 | 12 |
| VR031 | Insulin | 1:0 | Chemical | P3 | 125 |
| VR006 | Levothyroxine | 1:0 | UV | P3 | 2 |
| VR020 | Levothyroxine | 1:2 | UV | P6 | 120 |
| VR007 | Lysozyme | 1:0 | Chemical | P3 | 20 |
| VR008 | Lysozyme | 1:0 | UV | P3 | 11 |
| VR017 | Oxaliplatin | 1:0 | Chemical | P3 | 4 |
| VR018 | Oxaliplatin | 1:0 | Chemical | P3 | 5 |
| VR016 | Pregabalin | 1:0 | Chemical | P3 | 11 |
| VR024 | Pregabalin | 1:2 | Chemical | P6 | 40 |
| VR004 | Procaine | 1:0 | Chemical | P3 | 8 |
| VR022 | Procaine | 1:2 | Chemical | P6 | 132 |
| VR035 | Tenofovir disoproxil | 1:0 | Chemical | P3 | 10 |
| VR001 | Tranexamic acid | 1:0 | Chemical | P3 | 4 |

Degraded Hydrogel Prodrug Spectra

Figure 21:
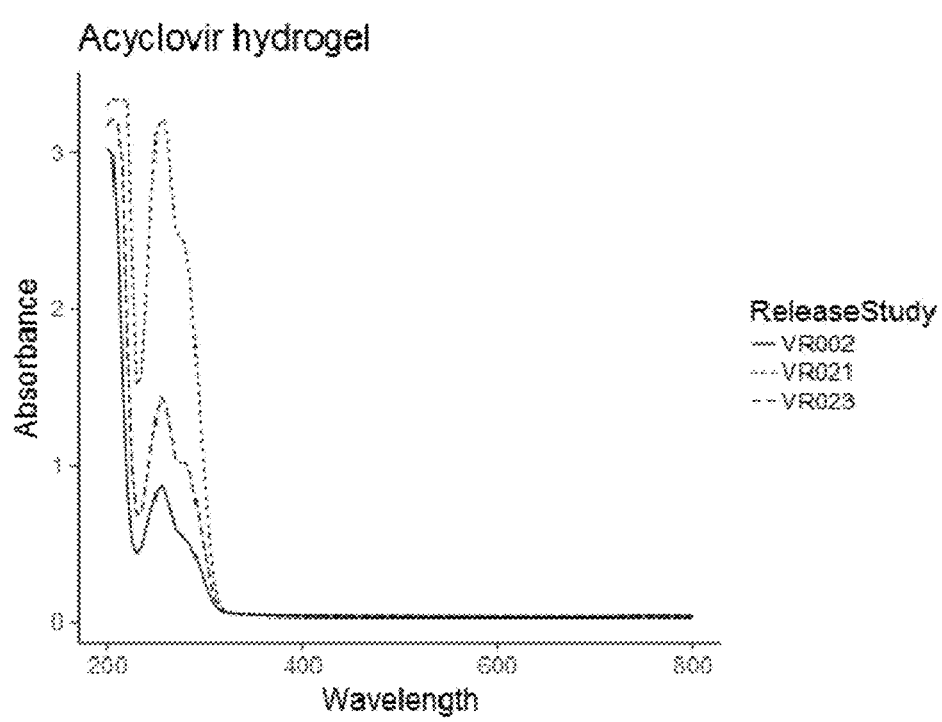
FIG. 21 shows the absorbance spectrum of various acyclovir hydrogel prodrug batches after complete degradation in water.
Figure 23:
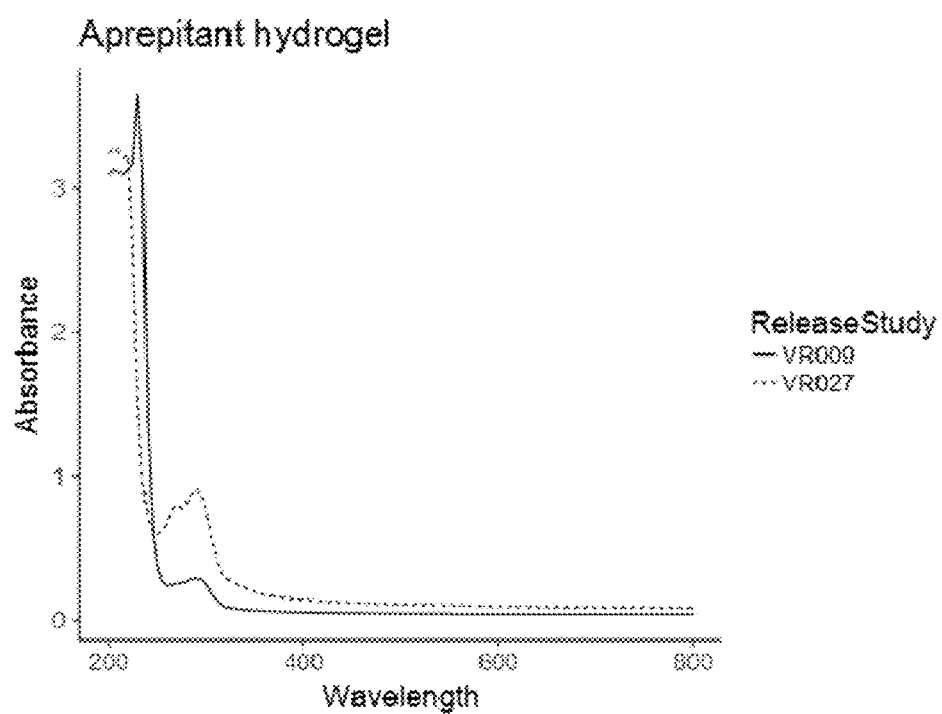
FIG. 23 shows the absorbance spectrum of various aprepitant hydrogel prodrug batches after complete degradation in water.
Figure 25:
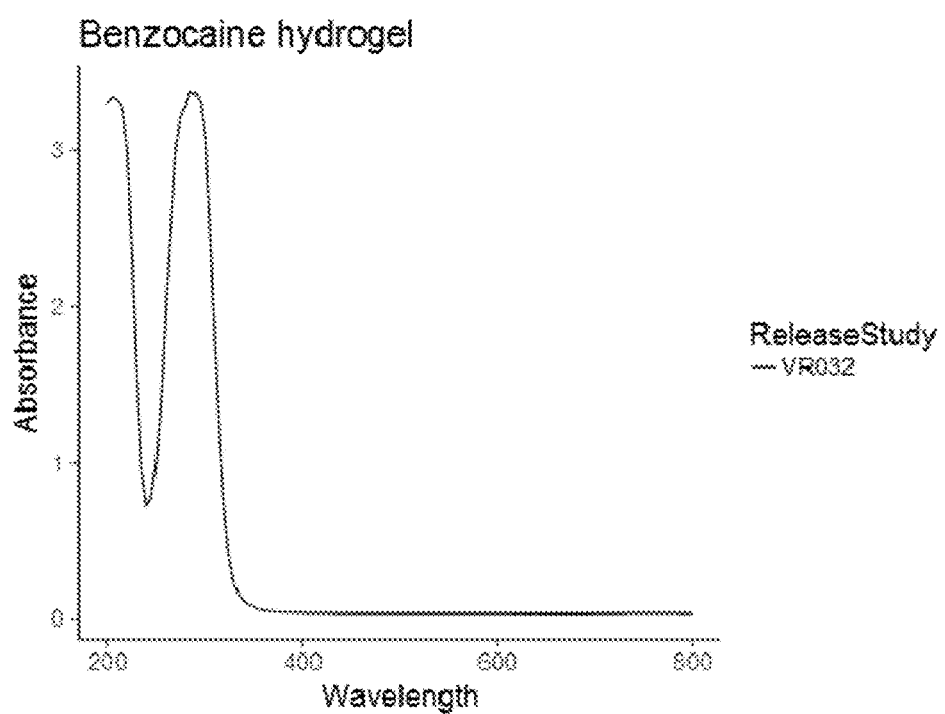
FIG. 25 shows the absorbance spectrum of a benzocaine hydrogel prodrug after complete degradation in water.
Figure 27:
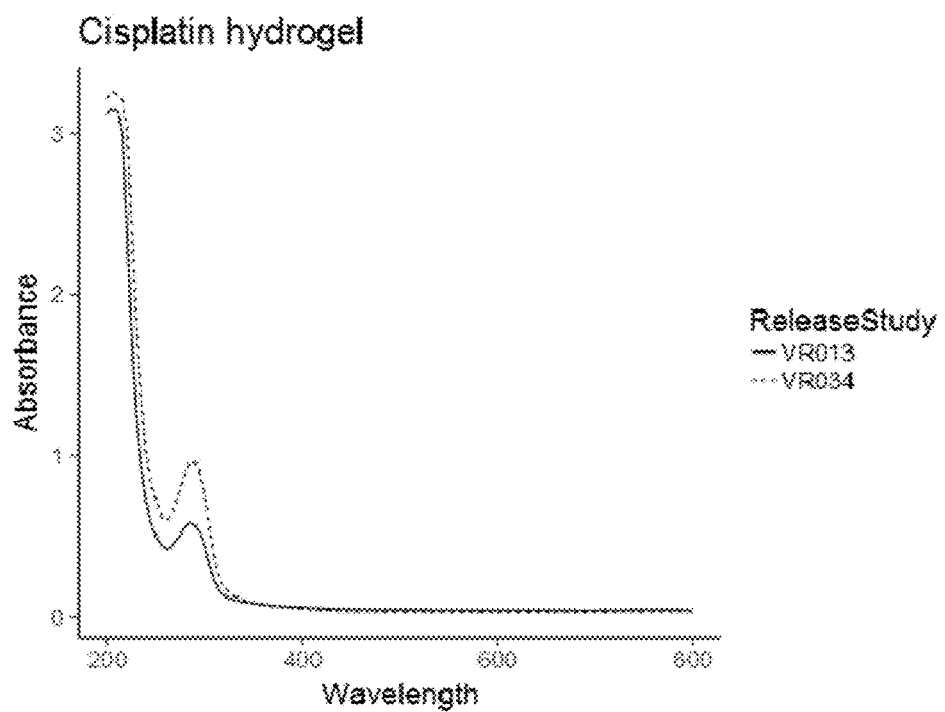
FIG. 27 shows the absorbance spectrum of various cisplatin hydrogel prodrug batches after complete degradation in water.
Figure 29:
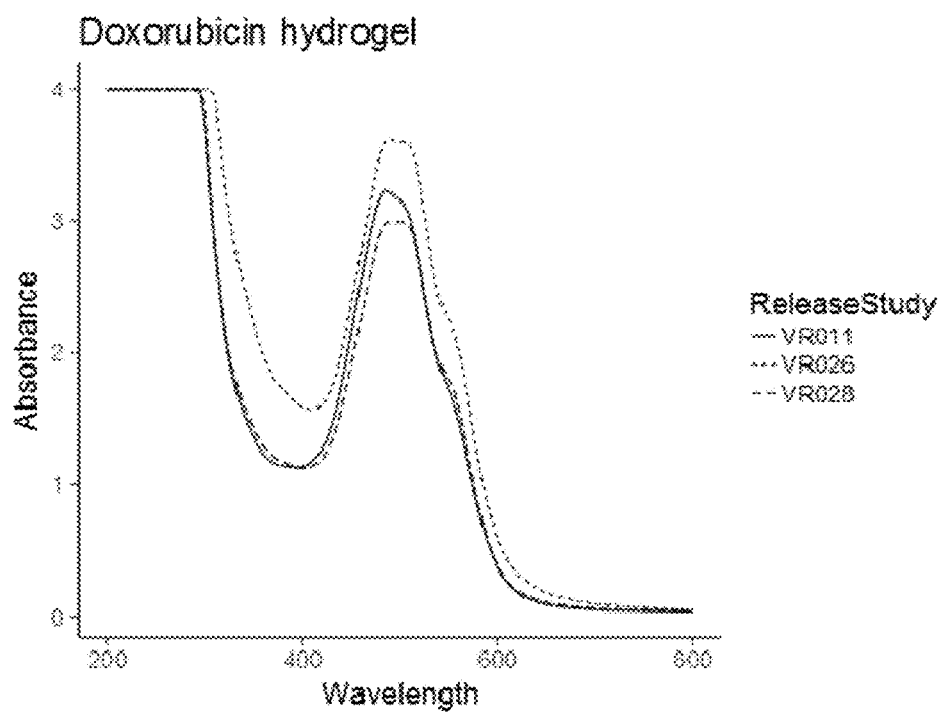
FIG. 29 shows the absorbance spectrum of various doxorubicin hydrogel prodrug batches after complete degradation in water.
Figure 31:
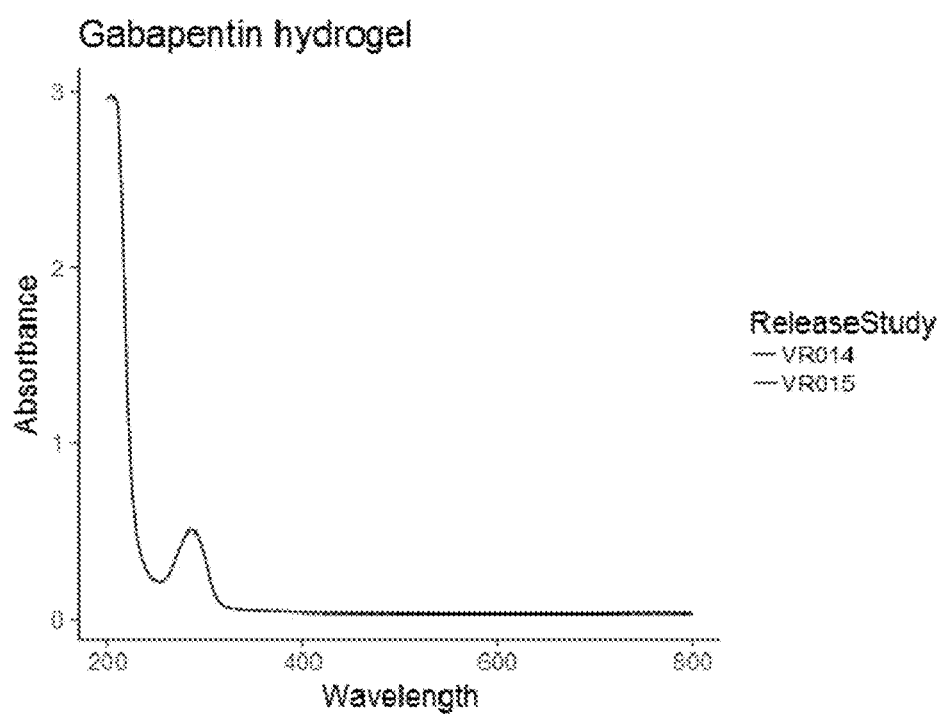
FIG. 31 shows the absorbance spectrum of various gabapentin hydrogel prodrug batches after complete degradation in water.
Figure 33:
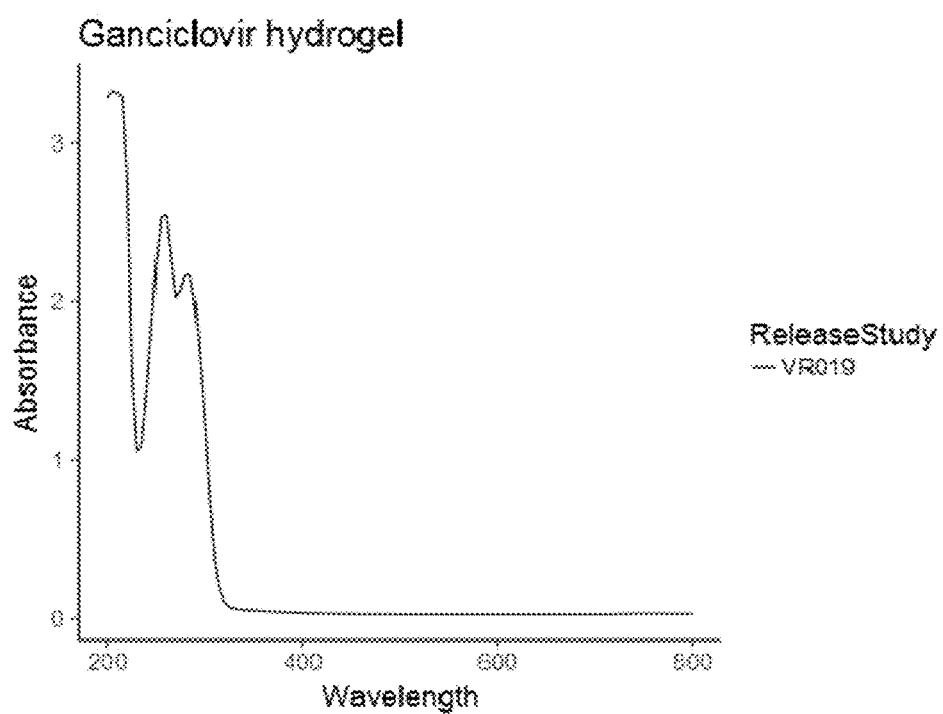
FIG. 33 shows the absorbance spectrum of various ganciclovir hydrogel prodrug batches after complete degradation in water.
Figure 35:
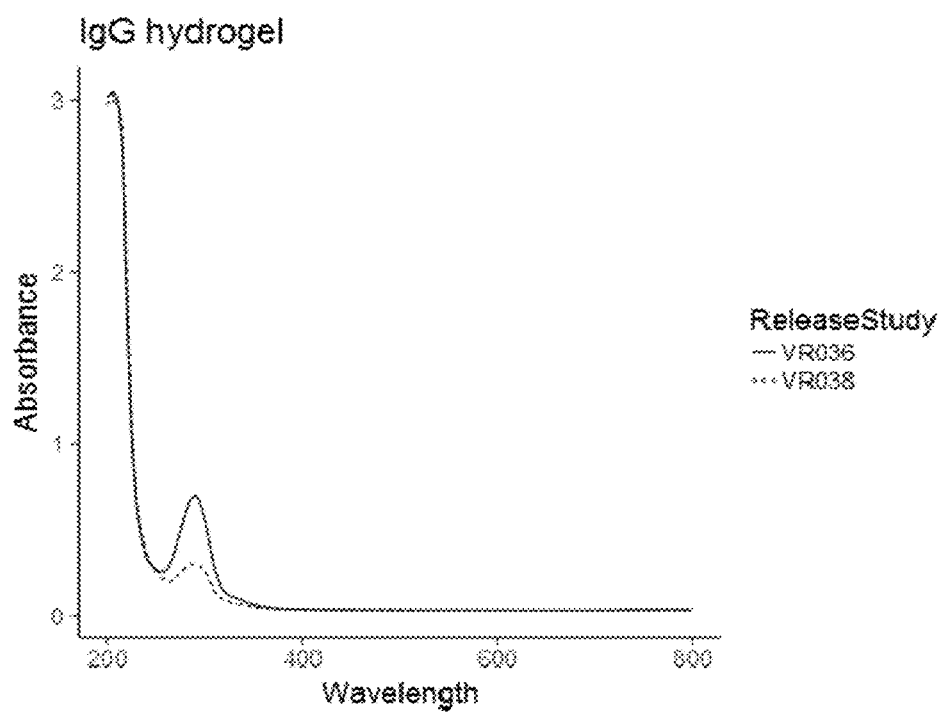
FIG. 35 shows the absorbance spectrum of various Immunoglobulin G (IgG) hydrogel prodrug batches after complete degradation in water.
Figure 39:
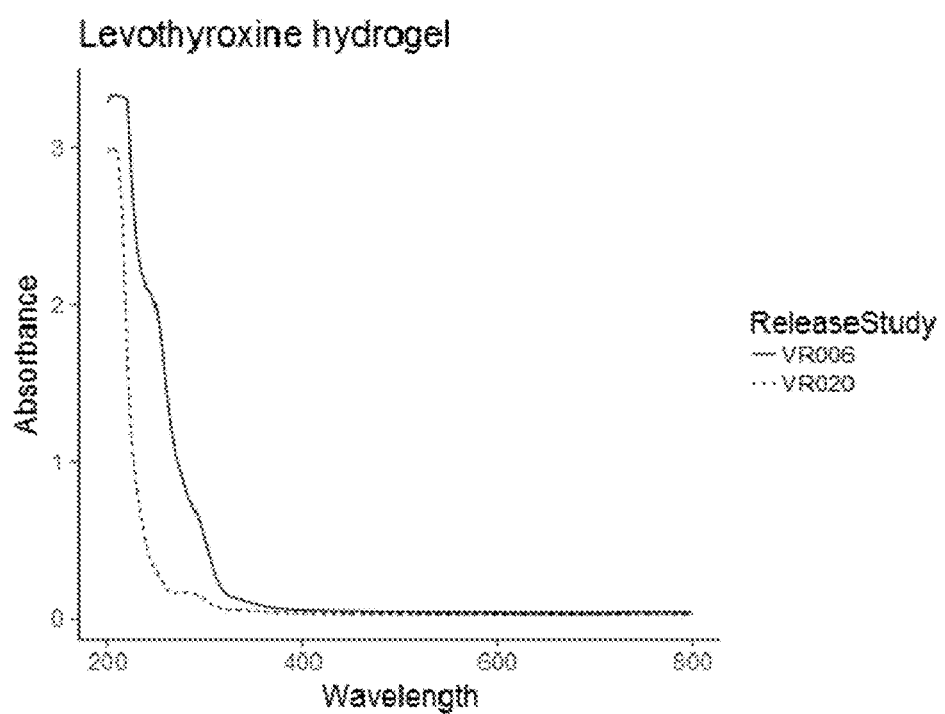
FIG. 39 shows the absorbance spectrum of various levothyroxine hydrogel prodrug batches after complete degradation in water.
Figure 41:
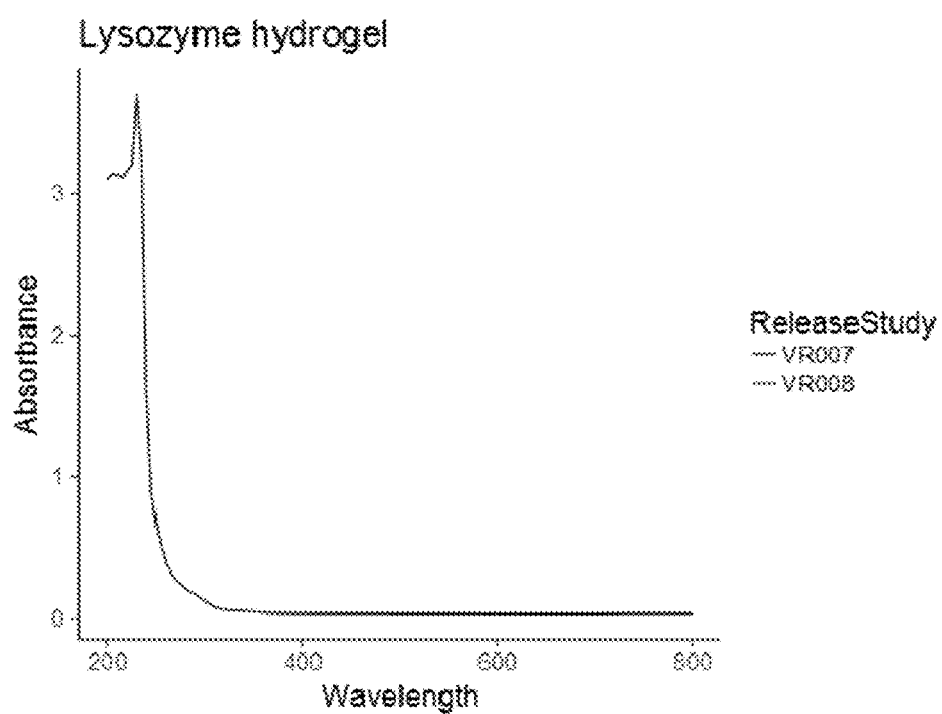
FIG. 41 shows the absorbance spectrum of various lysozyme hydrogel prodrug batches after complete degradation in water.
Figure 43:
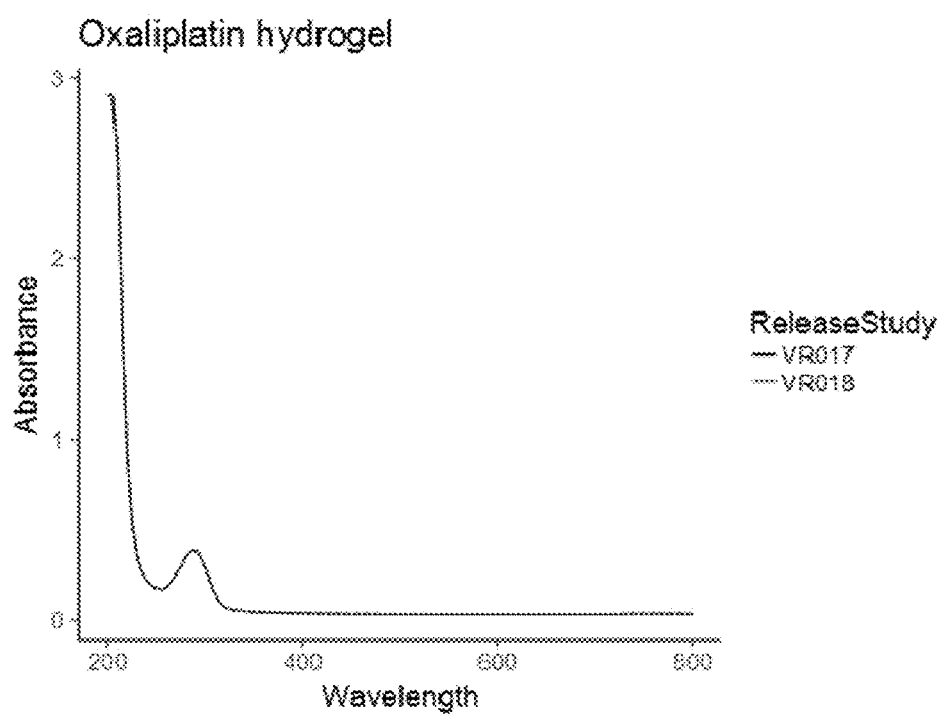
FIG. 43 shows the absorbance spectrum of various oxaliplatin hydrogel prodrug batches after complete degradation in water.
Figure 45:
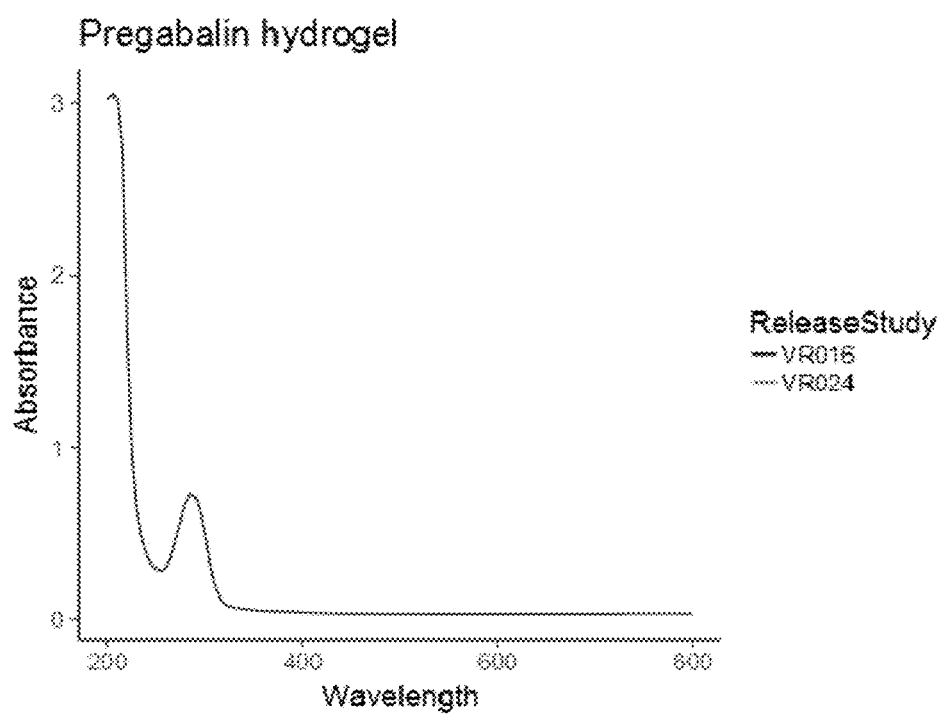
FIG. 45 shows the absorbance spectrum of various pregabalin hydrogel prodrug batches after complete degradation in water.
Figure 47:
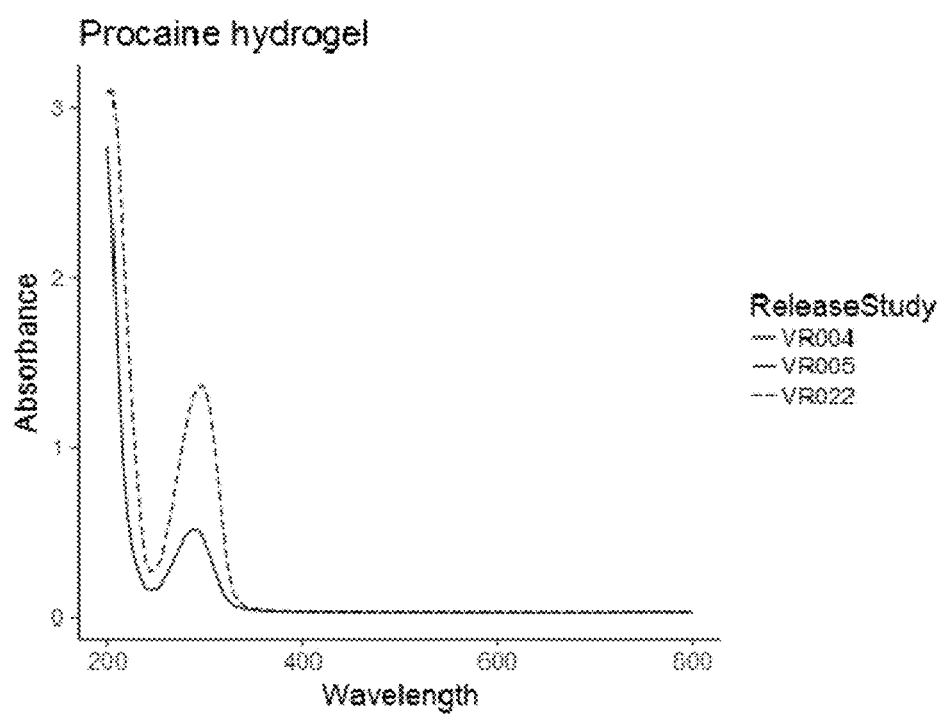
FIG. 47 shows the absorbance spectrum of various procaine hydrogel prodrug batches after complete degradation in water.
Figure 49:
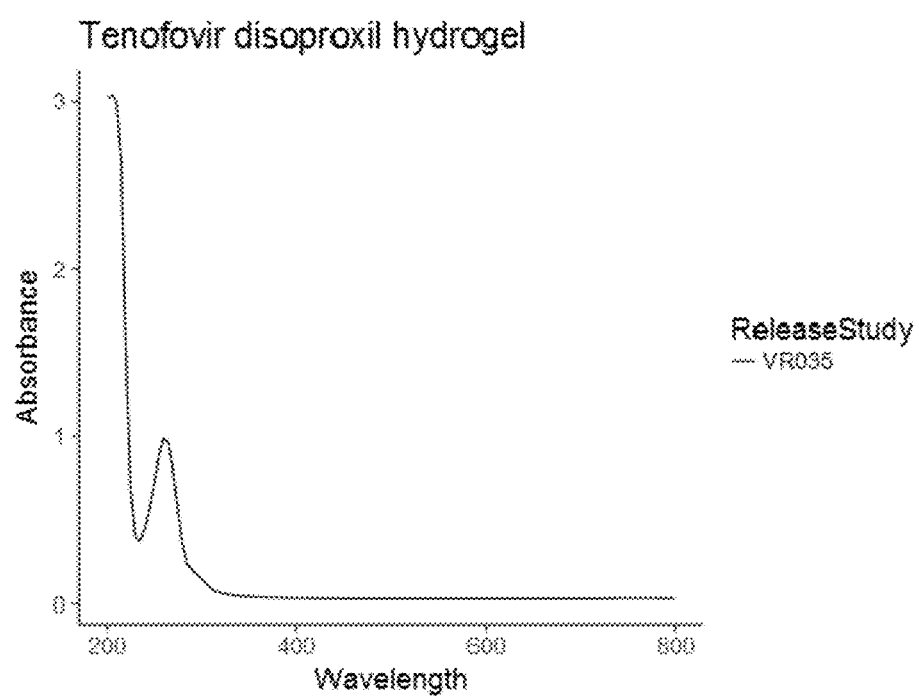
FIG. 49 shows the absorbance spectrum of a tenofovir disproxil hydrogel prodrug after complete degradation in water.
Figure 51:
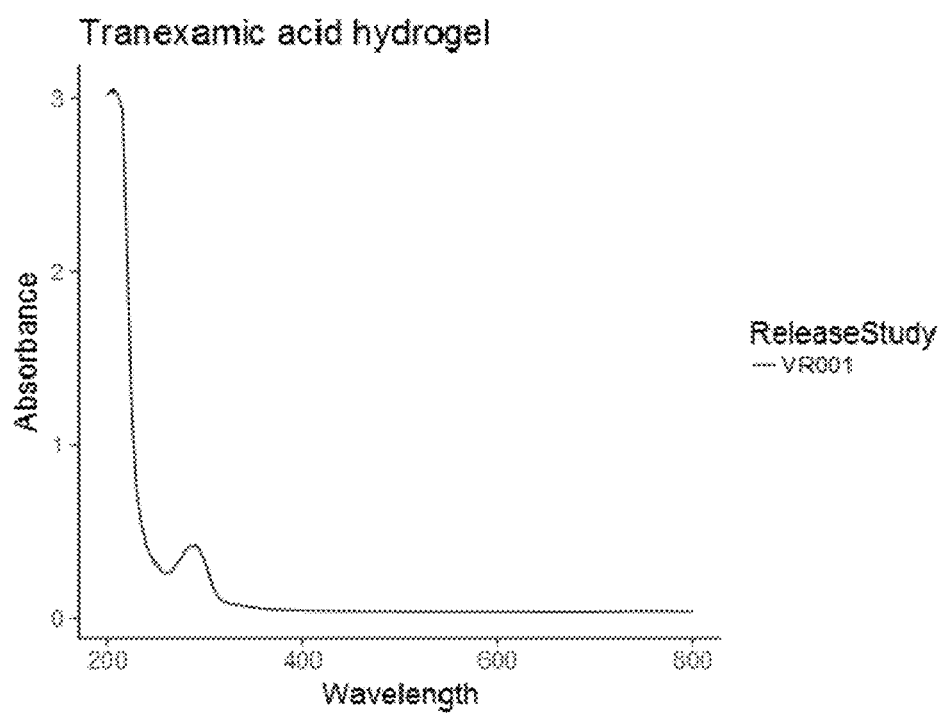
FIG. 51 shows the absorbance spectrum of a tranexamic acid hydrogel prodrug after complete degradation in water.

Absorbance spectra were measured for fully degraded hydrogel prodrugs to determine the peaks to be used when measuring drug concentrations. Terminal time points from release studies were used to generate all spectra below. The intensity of the peaks is arbitrary since these samples were of unknown concentration. Absorbance spectra of degraded hydrogels were performed on hydrogels containing acyclovir (FIG. 21), aprepitant (FIG. 23), benzocaine (FIG. 25), cisplatin (FIG. 27), doxorubicin (FIG. 29), gabapentin (FIG. 31), ganciclovir (FIG. 33), IgG (FIG. 35), Insulin (FIG. 37), levothyroxine (FIG. 39), lysozyme (FIG. 41), oxalipatin (FIG. 43), pregabalin (FIG. 45), procaine (FIG. 47), tenofovir disoproxil (FIG. 49) and tranexamic acid (FIG. 51).

Drug Release Graphs

Figure 22:
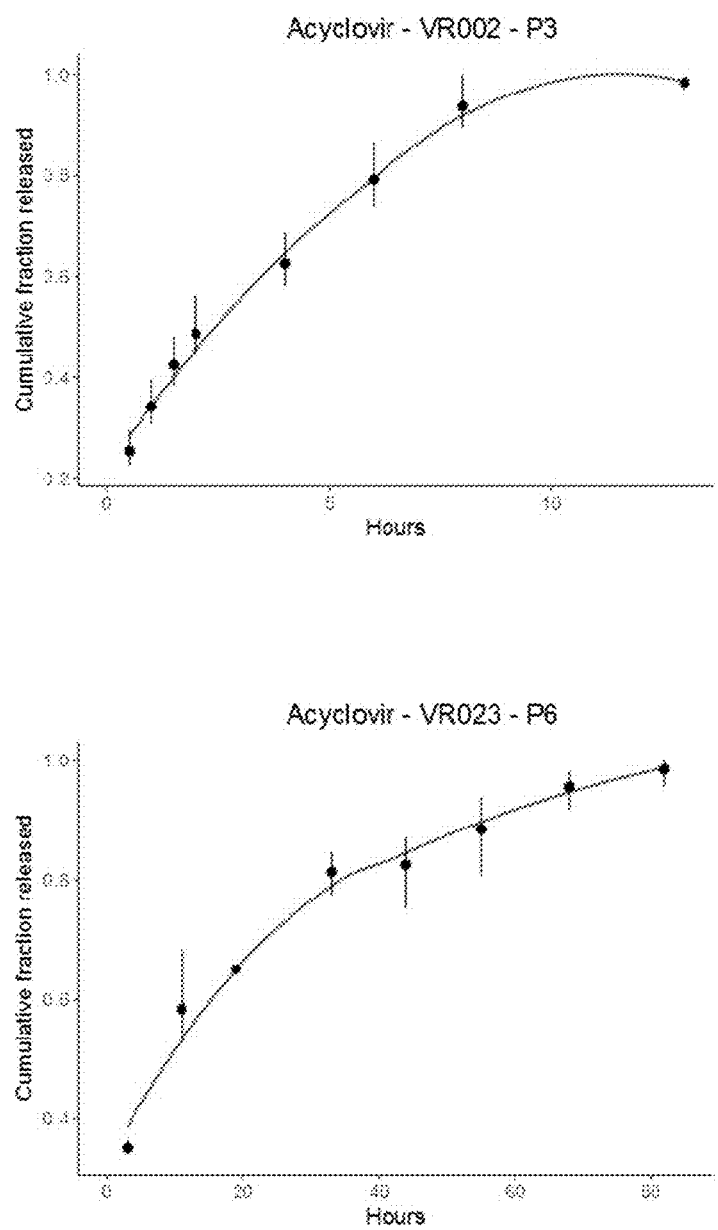
FIG. 22 shows the drug release from acyclovir hydrogel prodrugs prepared using reaction schemes P3 and P6.
Figure 24:
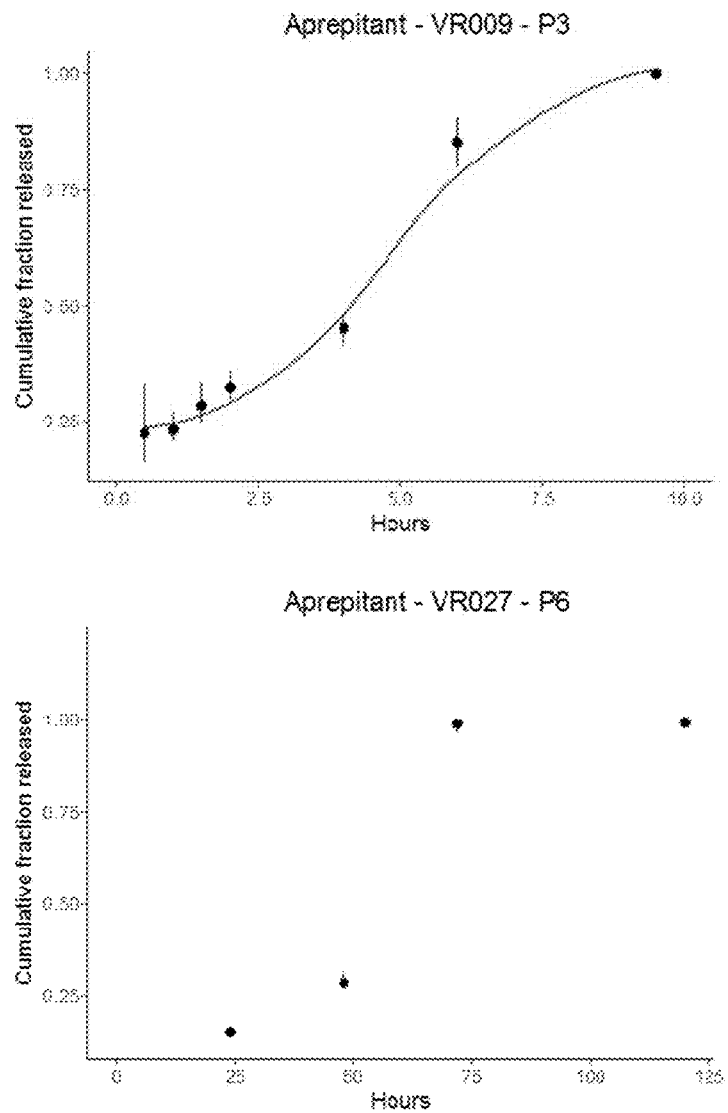
FIG. 24 shows the drug release from aprepitant hydrogel prodrugs prepared using reaction schemes P3 and P6.
Figure 26:
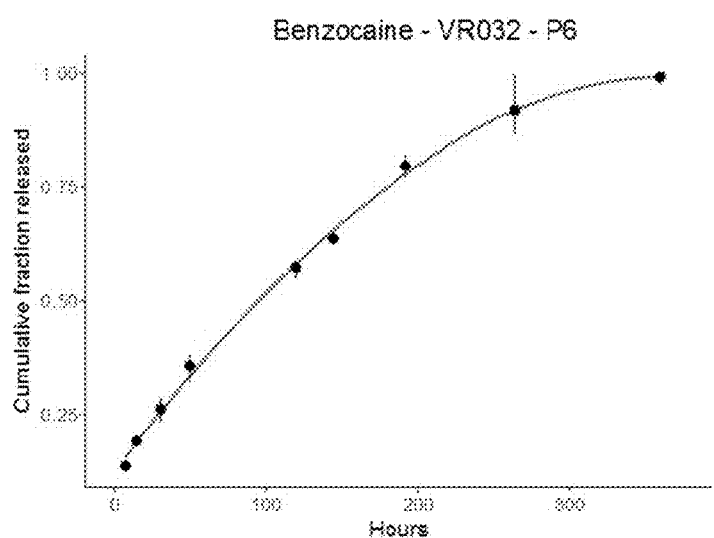
FIG. 26 shows the drug release from a benzocaine hydrogel prodrug prepared using reaction scheme P6.
Figure 28:
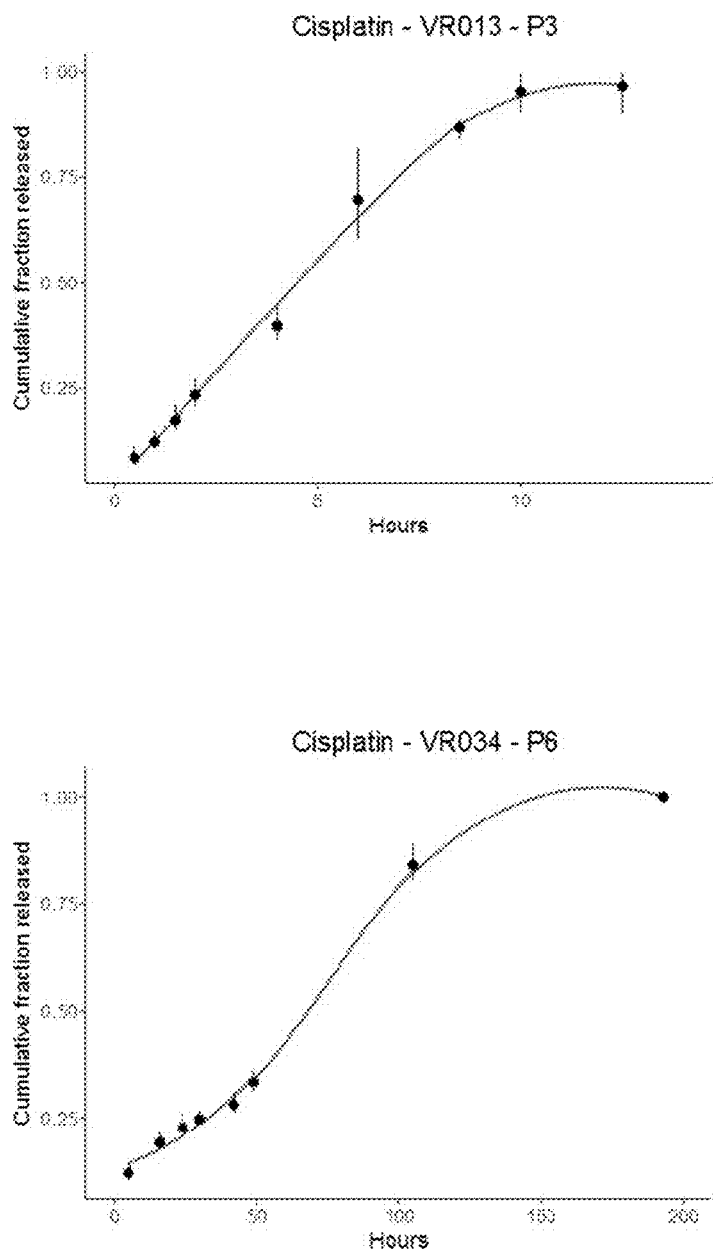
FIG. 28 shows the drug release from cisplatin hydrogel prodrugs prepared using reaction schemes P3 and P6.
Figure 30:
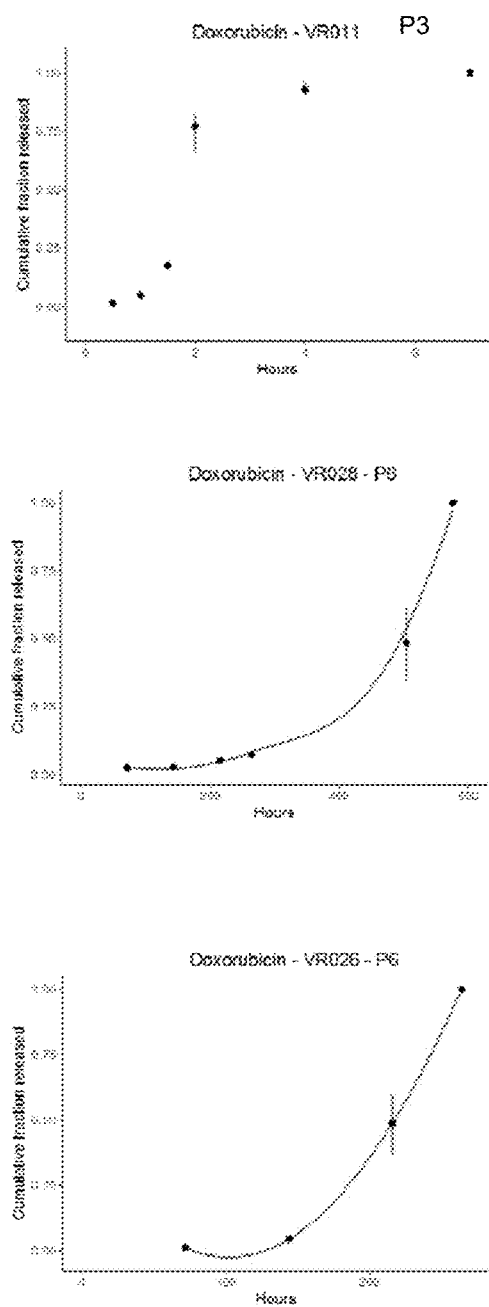
FIG. 30 shows the drug release from doxorubicin hydrogel prodrugs prepared using reaction schemes P3 and P6.
Figure 32:
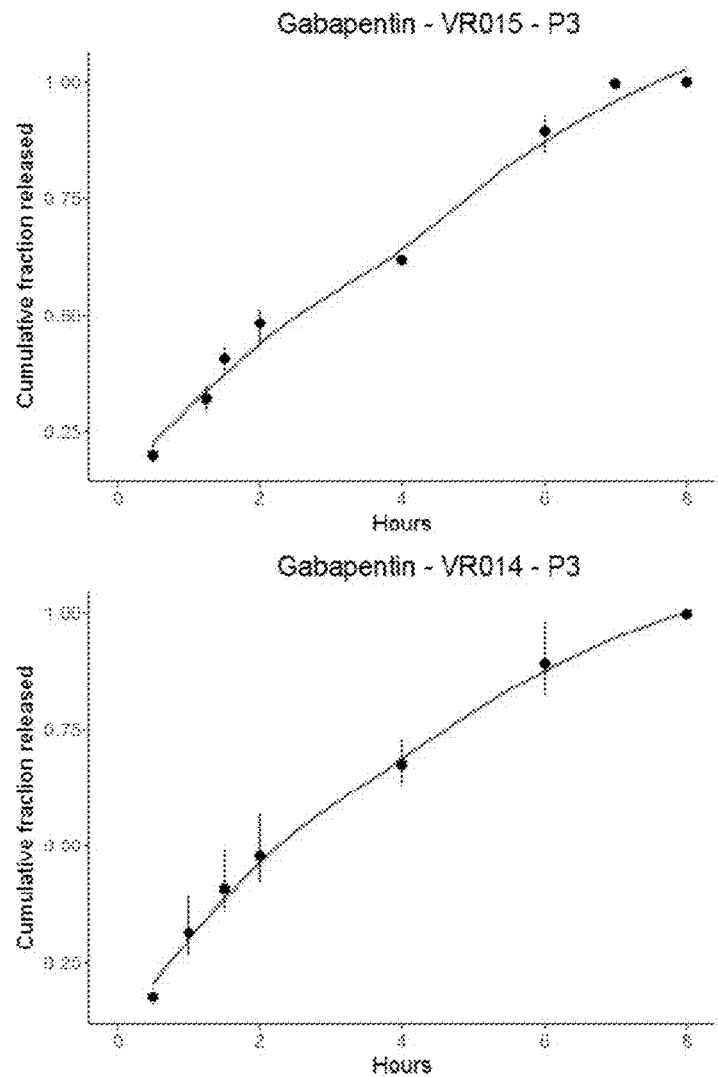
FIG. 32 shows the drug release from gabapentin hydrogel prodrugs prepared using reaction schemes P3 and P6.
Figure 34:
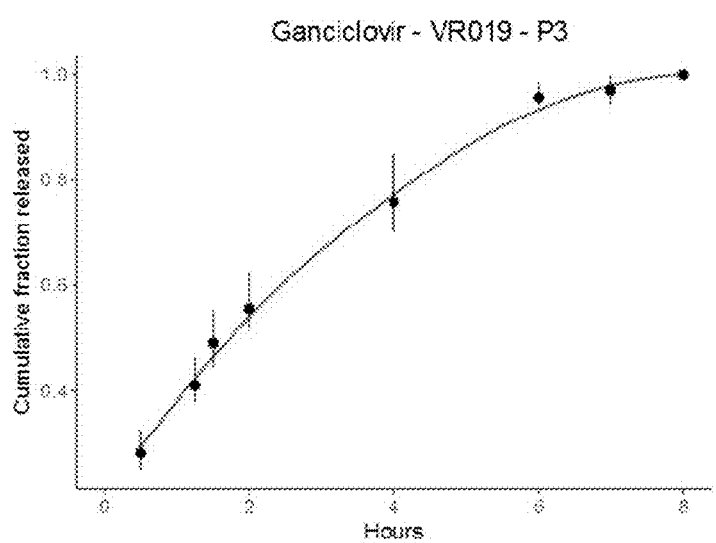
FIG. 34 shows the drug release from a ganciclovir hydrogel prodrug prepared using reaction scheme P3.
Figure 36:
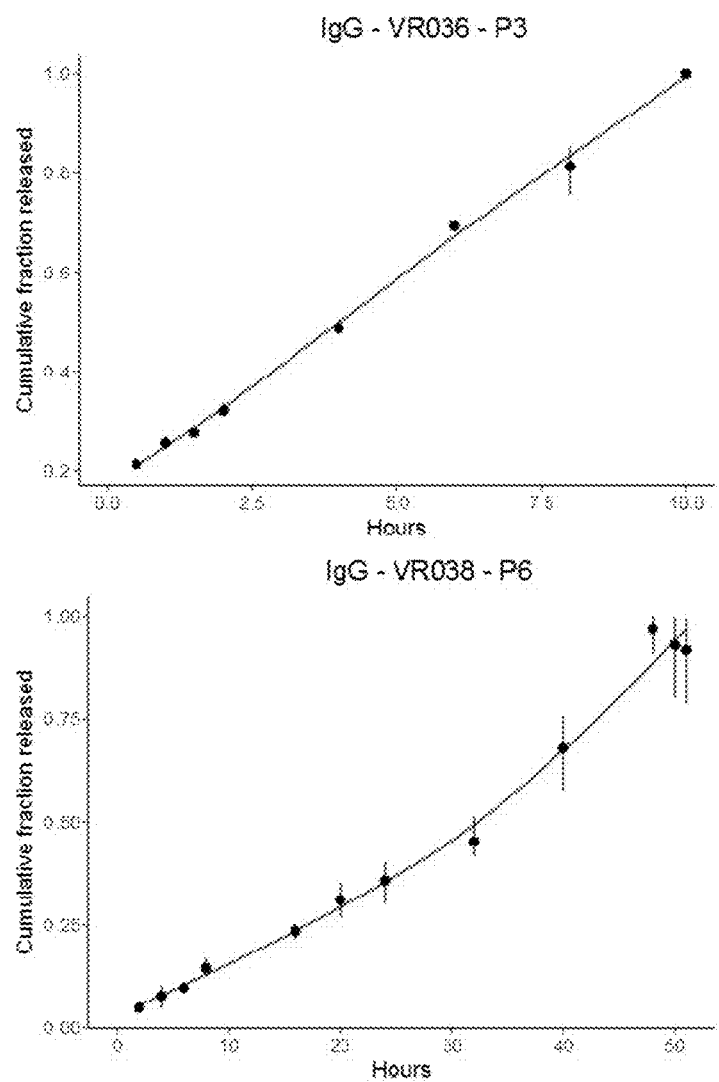
FIG. 36 shows the drug release from IgG hydrogel prodrugs prepared using reaction schemes P3 and P6.
Figure 38:
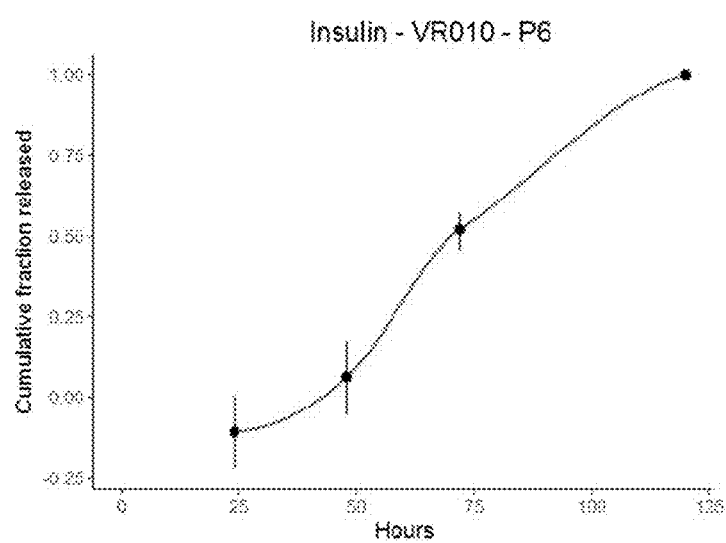
FIG. 38 shows the drug release from insulin hydrogel prodrugs prepared using reaction schemes P3 and P6.
Figure 40:
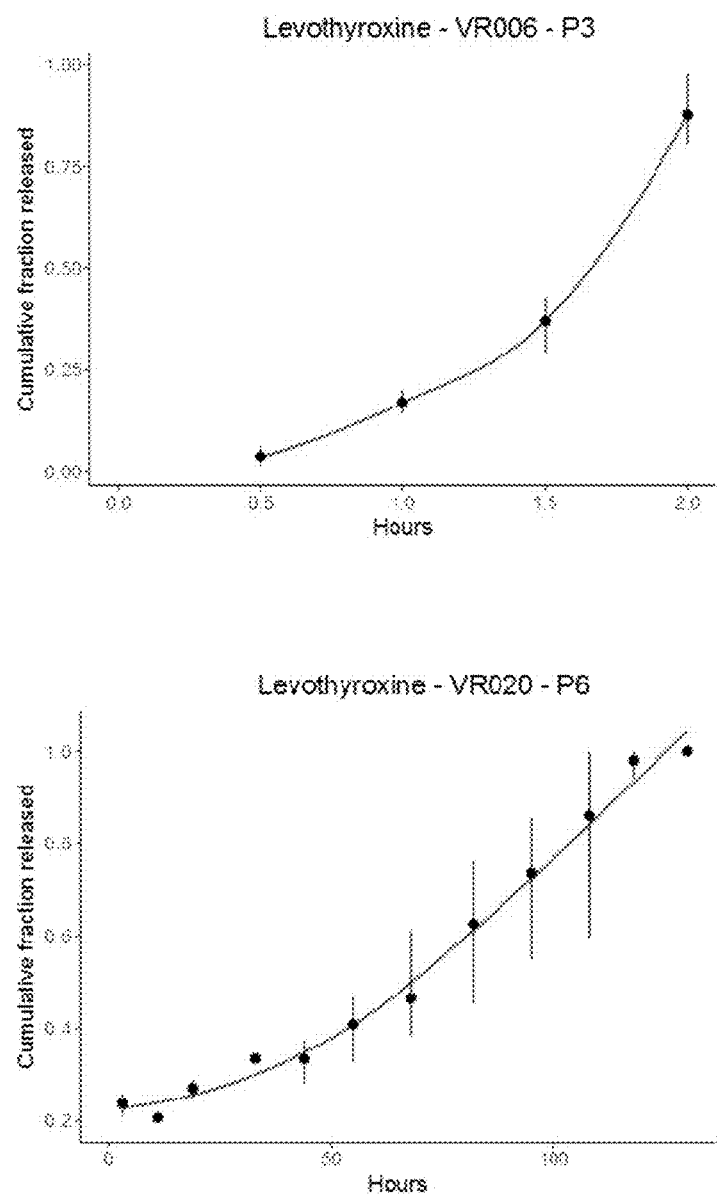
FIG. 40 shows the drug release from levothyroxine hydrogel prodrugs prepared using reaction schemes P3 and P6.
Figure 42:
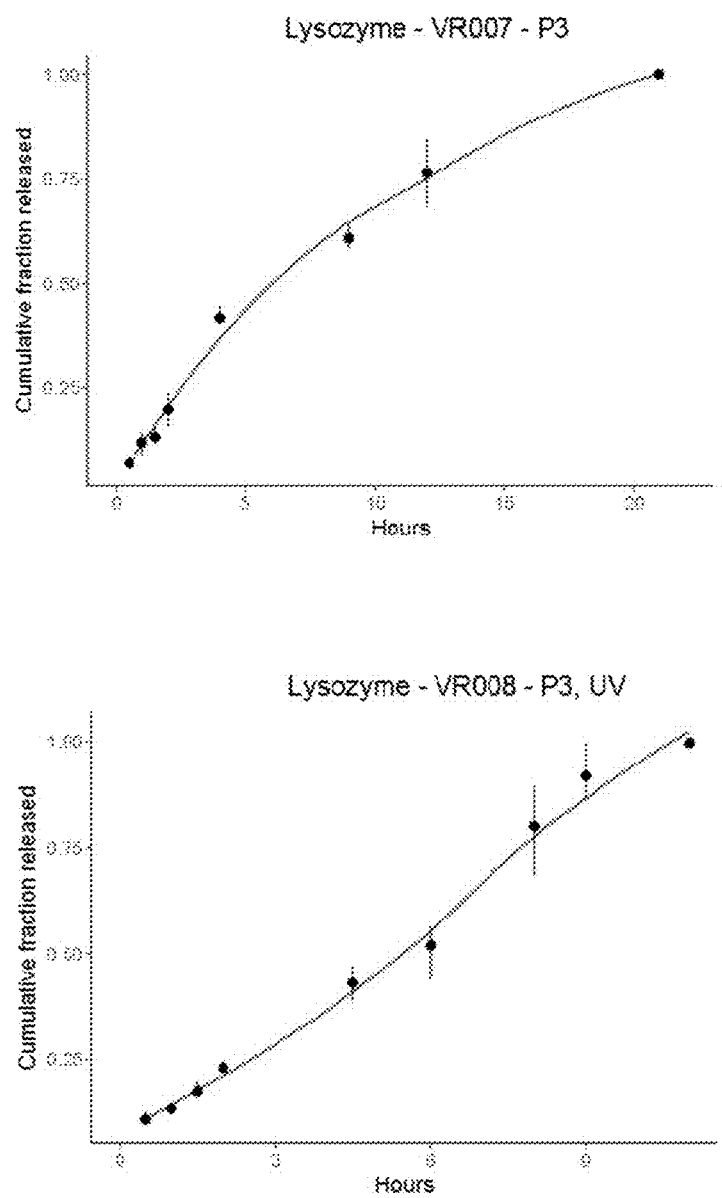
FIG. 42 shows the drug release from lysozyme hydrogel prodrugs prepared using reaction schemes P3 and P6.
Figure 44:
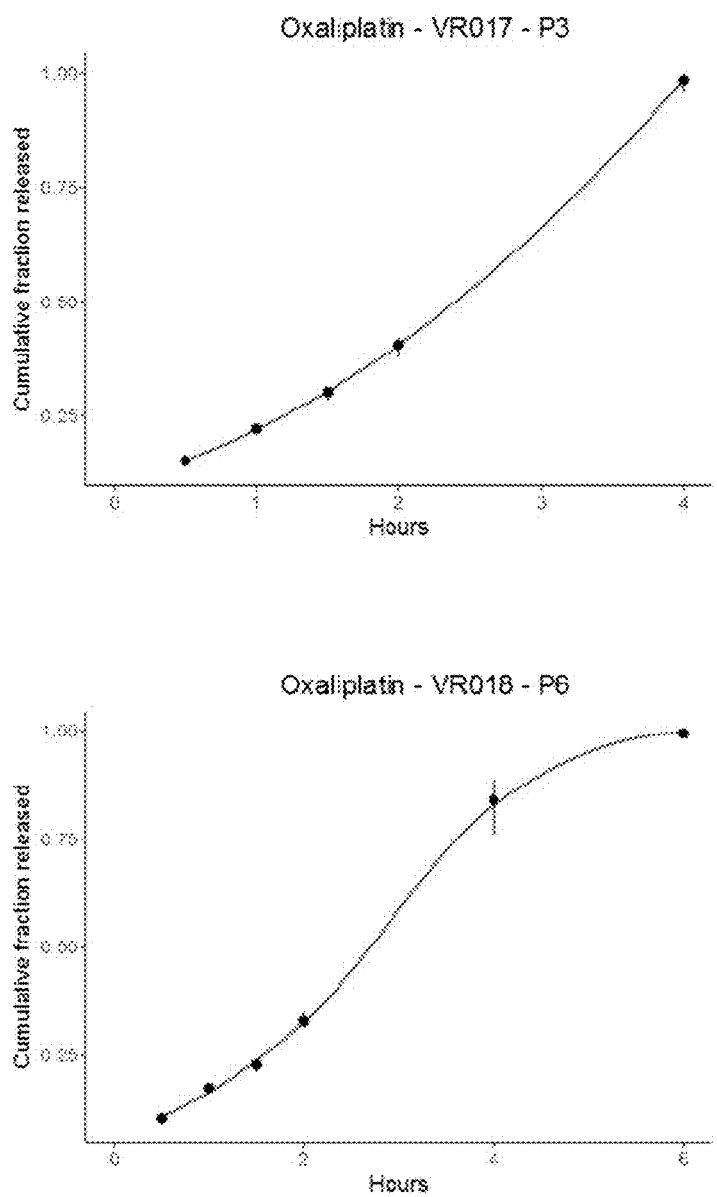
FIG. 44 shows the drug release from oxaliplatin hydrogel prodrugs prepared using reaction schemes P3 and P6.
Figure 46:
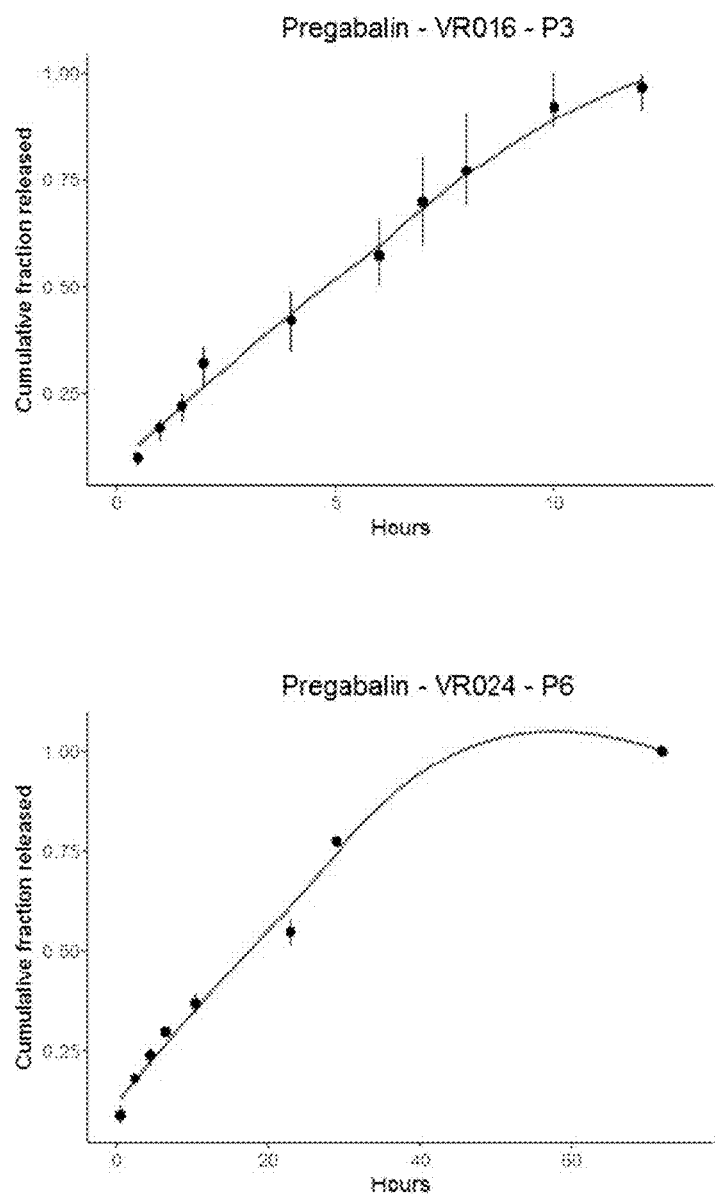
FIG. 46 shows the drug release from pregabalin hydrogel prodrugs prepared using reaction schemes P3 and P6.
Figure 48:
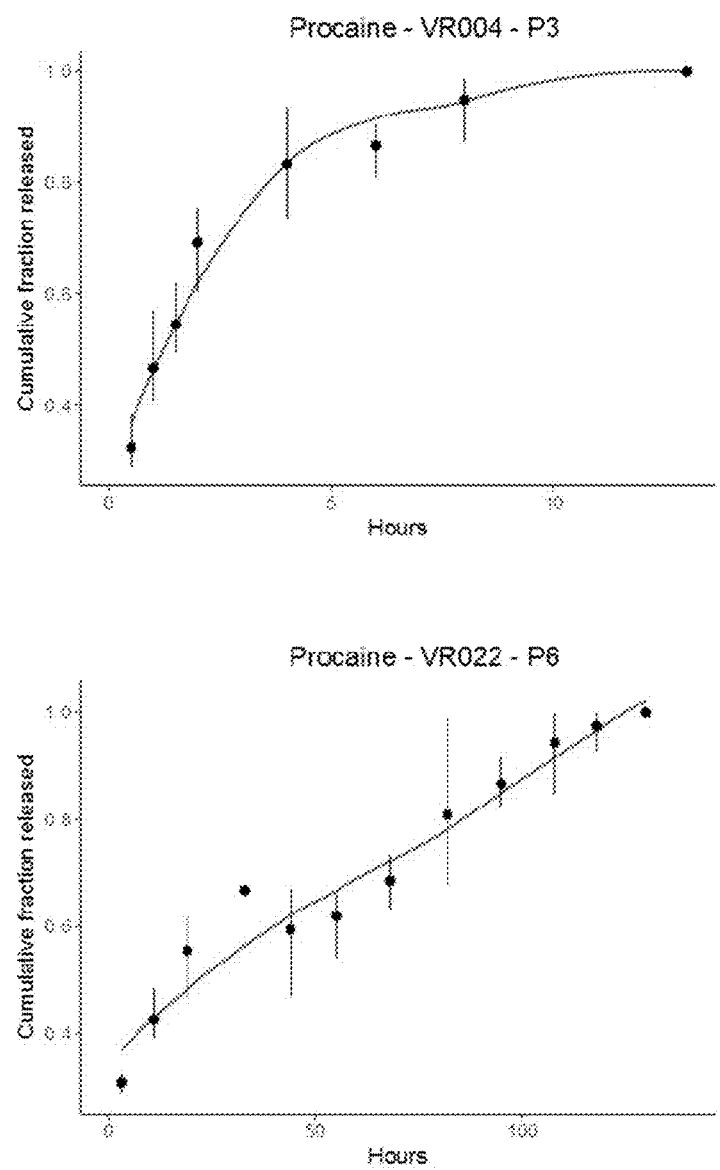
FIG. 48 shows the drug release from procaine hydrogel prodrugs prepared using reaction schemes P3 and P6.
Figure 50:
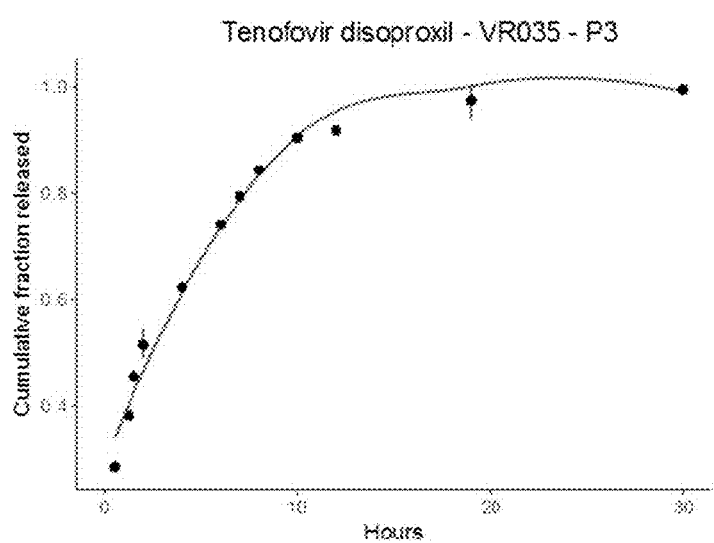
FIG. 50 shows the drug release from a tenofovir disproxil hydrogel prodrug prepared using reaction scheme P3.
Figure 52:
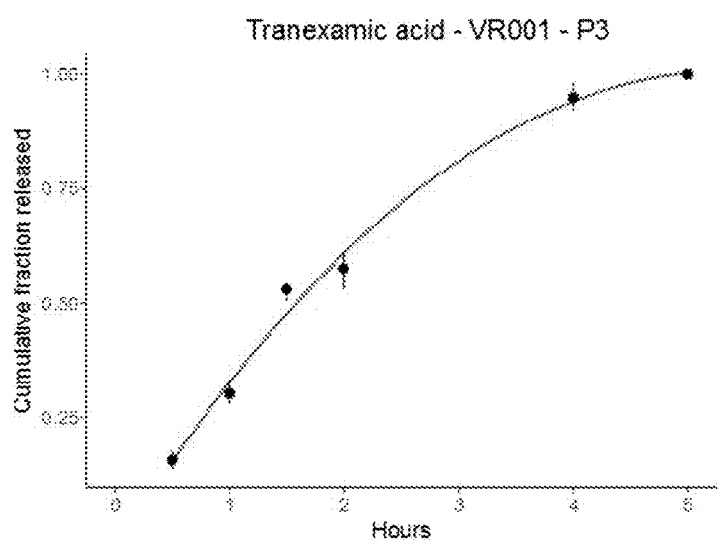
FIG. 52 shows the drug release from a tranexamic acid hydrogel prodrug prepared using reaction scheme P3.

All drug release studies were performed with 3 replicates, and data is presented as the mean+/−95% confidence interval. When appropriate a locally weighted polynomial regression (LOESS) line is fitted to the data to visualize the kinetics. Methods for the drug release are described above. Drug release experiments were performed from acyclovir hydrogel prodrug made from using reaction schematic P3 and P6 (FIG. 22), aprepitant hydrogel prodrug made from using reaction schematic P3 and P6 (FIG. 24), benzocaine hydrogel prodrug made from using reaction schematic P6 (FIG. 26), cisplatin hydrogel prodrug made from using reaction schematic P3 and P6 (FIG. 28), doxorubicin hydrogel prodrug made from using reaction schematic P3 (VR011) and P6 (VR026 and VR028) (FIG. 30), gabapentin hydrogel prodrug made from using reaction schematic P3 and P3 (FIG. 32), ganciclovir hydrogel prodrug made from using reaction schematic P3 (FIG. 34), IgG hydrogel prodrug made from using reaction schematic P3 and P6 (FIG. 36), insulin hydrogel prodrug made from using reaction schematic P3 and P6 (FIG. 38), levothyroxine hydrogel prodrug made from using reaction schematic P3 and P6 (FIG. 40), lysozyme hydrogel prodrug made from using reaction schematic P3 and using reaction schematic P3 and UV cross-linking (FIG. 42), oxaliplatin hydrogel prodrug made from using reaction schematic P3 and P6 (FIG. 44), pregabalin hydrogel prodrug made from using reaction schematic P3 and P6 (FIG. 46), procaine hydrogel prodrug made from using reaction schematic P3 and P6 (FIG. 48), tenofovir disoproxil hydrogel prodrug made from using reaction schematic P3 (FIG. 50) and tranexamic acid hydrogel prodrug made from using reaction schematic P3 (FIG. 52). As shown from the drug release data provided herein, the drugs can be released steadily, thus following the zero order drug release kinetics.

Cytotoxicity

For the cytotoxicity studies, NIH 3T3 cells were plated in 96-well plates at $5 \times 10^4$ cells per well for 16 h. Cells were treated with fully degraded IgG hydrogel prodrug in water (Sample 1) or fully degraded drug-free hydrogels (Sample 2) at 0.025, 0.25 and 2.5 mg/ml for 24 h. Sodium azide was used as a reference control between 0.002 and 2%. After 24 hours, cells were then treated with WST-1 reagent for up to 4 h and the absorbance of the samples was measured using a microplate reader. In the data below, lower absorbances indicate higher cytotoxicity.

Figure 53:
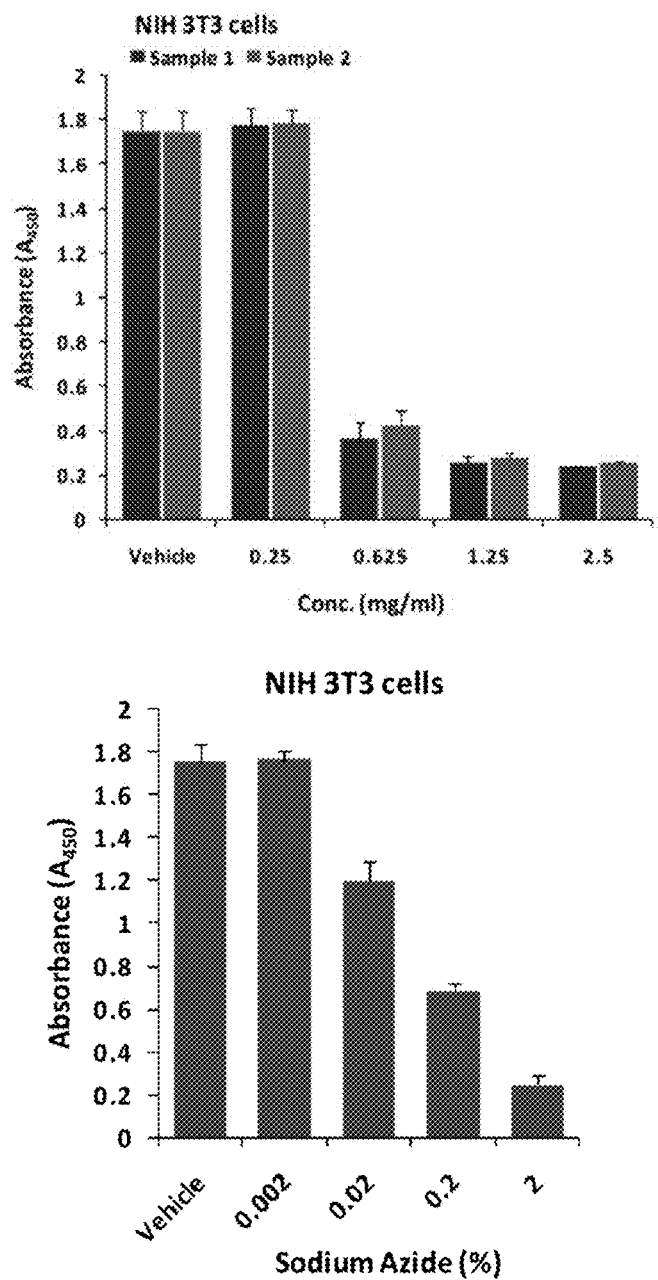
FIG. 53 shows the cytotoxicity of IgG hydrogel prodrug degradation products (Sample 1) and corresponding drug-free hydrogels (Sample 2) as compared to the cytotoxicity of sodium azide. The bottom panel shows the control sodium azide that was serially diluted as a cytotoxicity assay control.

Results of the cytotoxicity of the IgG hydrogel prodrug degradation are shown in FIG. 53. As shown in FIG. 53, cytotoxicity of IgG hydrogel prodrug degradation byproducts (Sample 1) and corresponding drug-free hydrogels (Sample 2), indicate no change in cytotoxicity due to the incorporation of drug. Pure IgG caused zero toxicity.

Molecular Weight Analysis

Pure IgG polymer prodrug, pure insulin polymer prodrug, fully degraded IgG hydrogel prodrug in water, and fully degraded insulin hydrogel prodrug in water were analyzed for molecular weight and polydispersity using GPC. This analysis was performed to verify the success of the polymerization reaction and to verify that the hydrogels completely degrade hydrolytically.

The results indicate that the polymer prodrugs have similar molecular weight distributions prior to crosslinking, with the dominant peak consisting of approximately 4 kDa chains, which corresponds to approximately 5 or 6 repeat units (diacrylate MW=525 Da and amine MW=73 Da). The degraded hydrogel samples had molecular weights approximately equal to the diacrylate (525 Da), suggesting complete biodegradation into monomer-sized byproducts.

The released drug was visible as a high molecular weight tail on the chromatogram, indicating that drug is released separate from the majority of degraded non-drug polymer backbone.

As shown in Table 2, below is a GPC analysis of several drugs before degradation.

TABLE 1

GPC analysis of IgG polymer prodrug (1A), fully degraded IgG hydrogel prodrug (1B), insulin polymer prodrug (2A), and fully degraded insulin polymer prodrug (2B). The analysis indicates that the dominant peak of the polymer prodrugs is consistent before degradation, and the molecular weights of the degradation byproducts closely approximate the poly(ethylene glycol)-based diacrylate monomers used in the original synthesis (MW = 525).

| Sample | Features | Peak MW (Mp) (Da) | Polydispersity (Approximate) |
|---|---|---|---|
| 1A | Three unresolved peaks | 4059 (Major) 1048 378 | 2.7 |
| 1B (Degraded) | One peak, no noticeable shoulders | 540 | 1.3 |
| 2A | Three unresolved peaks | 3423 (Major) 1005 408 | 2.5 |
| 2B (Degraded) | One peak, high MW tail | 499 | 1.3 |

More Alternatives

In some alternatives, a method of making a hydrogel prodrug is provided. The method of making a hydrogel prodrug can comprise providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is a secondary amine group. In some alternatives, the at least one amine group comprises at least two secondary amine groups. In some alternatives, the method comprises reacting the at least one acrylate with the at least two secondary amine groups of the at least one drug. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values listed. In some alternatives, the reacting is performed at a temperature of at least or equal to 20° C., 25° C., 30° C. or 35° C. or any temperature within a range defined by any two of the aforementioned values listed. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, antiarthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one amine group. In some alternatives, the at least one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1: 1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibodydrug conjugate, antibody or portion thereof, protein, oligopeptide, polypeptide, hormone, steroid, antipsychotic, antiAlzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the reacting step is performed for at least or equal to 1, 2, 3, 4, 5, 6, 7, 8, 9, 10, 12, 24, 36, 48 or 72 hours, or any time within a range defined by any two of the aforementioned values. In some alternatives the protein is insulin or lysozyme. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one primary amine group or at least one secondary amine group, wherein, the chemical spacer is a spacer in the backbone structure of the hydrogel prodrug. In some alternatives, the spacer comprises isobutylamine. In some alternatives, the chemical spacer comprises at least two secondary amine groups. In some alternatives, the chemical spacer is provided at a ratio of chemical spacer to at least one drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (betaamino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates between any two aforementioned numbers. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. In some alternatives, the targeting moiety is specific for a ligand on a tumor. In some alternatives, the targeting moiety is specific for a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, a hydrogel prodrug manufactured by any one of these alternatives is provided. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. A hydrogel prodrug made by any one of the alternatives herein is provided. The hydrogel prodrug comprises: at least one drug and at least one acrylate. In some alternatives, the hydrogel prodrug comprises 2, 3, 4, 5, 6, 7, 8, 9 or 10 different drugs. In some alternatives, the hydrogel prodrug comprises a nucleic acid analogue, amino ester-based drug, neurokinin agonist, platinum-based, amine-containing chemotherapeutics, anthracyclines, γ-aminobutyric acid-derived drugs, amino acid derivatives, aminated benzoic acid derivatives, proteins, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and tenofovir, valsartan, hydrochloraothiazide, lisdexamfetamine, mesalamine, memantine, pemetrexed, fingolimod, sitagliptin, metformin or darunavir. In some alternatives, the hydrogel prodrug comprises acyclovir, aprepitant, benzocaine, cisplatin, doxorubicin, gabapentin, ganciclovir, IgG, insulin, levothyroxine, oxaliplatin, pregabalin, procaine, tenofovir, tranexamic acid or 5-aminosalicylic acid. In some alternatives, the hydrogel prodrug comprises a chemical spacer. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill.

A method of making a hydrogel prodrug is provided. The method can include the following: providing at least one drug that comprises at least one amine group, providing at least one acrylate, reacting said at least one acrylate with the at least one amine group or at least two secondary amine groups of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is drug comprises at least a two secondary amine groups. In some alternatives, the drug further comprises at least two secondary amine groups. In some alternatives, at least one primary amine and/or at least one secondary amine are provided. In some alternatives, the at least one acrylate can have at least one acrylate group. In some alternatives, the at least one acrylate group is bound by an ester linkage to an opposing termini of a carbon chain. In some alternatives, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000 g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of at least or equal to 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration that is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutic s, Anthracyclines, γ-Aminobutyric acid-derived drugs, Amino acid derivatives, Aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one amine group. In some alternatives, the second drug comprises at least two additional secondary amine groups one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, Anthracyclines, γ-Aminobutyric acid-derived drugs, Amino acid derivatives, Aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an antiviral, an analgesic, an antibiotic, an anti-fungal, pregablin, glatiramer acetate, emtricitabine, emtricitabine and tenofovir, valsartan, hydrochloraothiazide, lisdexamfetamine, mesalamine, memantine, pemetrexed, fingolimod, sitagliptin, metformin or darunavir. In some alternatives, the reacting step is performed for at least or equal to 1, 2, 3, 4, 5, 6, 7, 8, 9, 10, 12, 24, 36, 48 or 72 hours, or within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to the at least one drug of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least one primary amine group of the chemical spacer or at least one secondary amine group of the chemical spacer is attached to a carbon chain. In some alternatives, the spacer comprises isobutylamine. In some alternatives, the carbon chain can have at least or equal to 1, 5, 10, 15, 20, 25 or 30 carbon atoms or any number of carbon atoms within a range defined by any two of the aforementioned values. In some alternatives, the carbon chain has substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. A hydrogel prodrug made by any one of the alternatives herein is provided. The hydrogel prodrug comprises: at least one drug and at least one acrylate. In some alternatives, the hydrogel prodrug comprises 2, 3, 4, 5, 6, 7, 8, 9 or 10 different drugs. In some alternatives, the hydrogel prodrug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and tenofovir, valsartan, hydrochloraothiazide, lisdexamfetamine, mesalamine, memantine, pemetrexed, fingolimod, sitagliptin, metformin or darunavir. In some alternatives, the hydrogel prodrug comprises acyclovir, aprepitant, benzocaine, cisplatin, doxorubicin, gabapentin, ganciclovir, IgG, insulin, levothyroxine, oxaliplatin, pregabalin, procaine, tenofovir, tranexamic acid or 5-aminosalicylic acid. In some alternatives, the hydrogel prodrug comprises a chemical spacer. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill.

A hydrogel prodrug made by any one of the alternatives herein is provided. The hydrogel prodrug comprises: at least one drug and at least one acrylate. In some alternatives, the hydrogel prodrug comprises 2, 3, 4, 5, 6, 7, 8, 9 or 10 different drugs. In some alternatives, the hydrogel prodrug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and tenofovir, valsartan, hydrochloraothiazide, lisdexamfetamine, mesalamine, memantine, pemetrexed, fingolimod, sitagliptin, metformin or darunavir. In some alternatives, the hydrogel prodrug comprises acyclovir, aprepitant, benzocaine, cisplatin, doxorubicin, gabapentin, ganciclovir, IgG, insulin, levothyroxine, oxaliplatin, pregabalin, procaine, tenofovir, tranexamic acid or 5-aminosalicylic acid. In some alternatives, the hydrogel prodrug comprises a chemical spacer. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill.

In some alternatives, a hydrogel prodrug delivery system is provided, comprising; the hydrogel prodrug manufactured by any one of the alternatives herein. The method of making a hydrogel prodrug can comprise providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. A method of making a hydrogel prodrug is provided. The method can include the following: providing at least one drug that comprises at least one amine group, providing at least one acrylate, reacting said at least one acrylate with the at least one amine group or at least two secondary amine groups of the at least one drug, thereby producing at least one polymer prodrug, wherein the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is a secondary amine group. In some alternatives, the at least one amine group comprises at least two secondary amine groups. In some alternatives, the method comprises reacting the at least one acrylate with the at least two secondary amine groups of the at least one drug. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values listed. In some alternatives, the reacting is performed at a temperature of at least or equal to 20° C., 25° C., 30° C. or 35° C. or any temperature within a range defined by any two of the aforementioned values listed. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one amine group. In some alternatives, the at least one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1: 1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the reacting step is performed for at least or equal to 1, 2, 3, 4, 5, 6, 7, 8, 9, 10, 12, 24, 36, 48 or 72 hours, or any time within a range defined by any two of the aforementioned values. In some alternatives the protein is insulin or lysozyme. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the spacer comprises isobutylamine. In some alternatives, the chemical spacer comprises at least two secondary amine groups. In some alternatives, the chemical spacer is provided at a ratio of chemical spacer to at least one drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates between any two aforementioned numbers. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. In some alternatives, the targeting moiety is specific for a ligand on a tumor. In some alternatives, the targeting moiety is specific for a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. In some alternatives of the system, the hydrogel prodrug comprises a peptide. In some alternatives of the system, the hydrogel prodrug comprises at least one drug. In some alternatives of the system, the at least one drug comprises a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the system, the hydrogel prodrug comprises a second, third, fourth, fifth, sixth, seventh, eighth, ninth or tenth drug. In some alternatives of the system, the second, third, fourth, fifth, sixth, seventh, eighth, ninth or tenth drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the system, the hydrogel prodrug comprises at least one acrylate. In some alternatives of the system, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives of the system, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives of the system, the cyclic carbon chains comprise saturated bonds, unsaturated bonds and/or heteroatoms. In some alternatives of the system, the acrylate comprises at least two acrylate groups and is a diacrylate. In some alternatives of the system, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives of the system, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives of the system, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives of the system, the second, third, fourth, fifth, sixth, seventh, eighth, ninth or tenth drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives of the system, the hydrogel prodrug further comprises a spacer. In some alternatives of the system, the spacer comprises a hydrophilic group, such as a hydroxyl group. In some alternatives of the system, the spacer comprises a carbon chain. In some alternatives of the system, the carbon chain comprises at least or equal to 1, 5, 10, 15, 20, 25 or 30 carbon atoms or any number of carbon atoms within a range defined by any two of the aforementioned values. In some alternatives of the system, the carbon chain comprises substituted heterocarbons, unsubstituted heterocarbons, saturated carbon bonds, unsaturated carbon bonds, branched cyclic carbon chains and/or unbranched cyclic carbon chains. In some alternatives of the system, the branched or unbranched cyclic carbon chains are saturated. In some alternatives of the system, the branched or unbranched cyclic carbon chains are unsaturated. In some alternatives of the system, the branched or unbranched cyclic carbon chains comprise heteroatoms. In some alternatives of the system, the hydrogel prodrug is a compressed sheet, film, incorporated into a scaffold, support or a dressing. In some alternatives of the system, the hydrogel prodrug is shaped into a tablet, an implantable device, microparticle or a pill. In some alternatives of the system, the hydrogel prodrug comprises a polymer structure, wherein, the polymer structure is a poly (beta amino ester) (PBAE). In some alternatives of the system, the hydrogel prodrug comprises a polymer structure, wherein, the primary amine of the drug is incorporated into the polymer structure by conjugate addition to a vinyl group of the at least one acrylate molecules, resulting in a tertiary amine within the polymer backbone, or wherein, two secondary amines of a drug molecule are each incorporated into the polymer structure by conjugate addition to the vinyl group of an acrylate molecule, resulting in two tertiary amines incorporated into the polymer backbone. In some alternatives of the system, the polymer structure terminates with acrylate ends. In some alternatives of the system, the drug is incorporated into the polymer structure and wherein, the drug is covalently linked between two acrylates. In some alternatives of the system, the spacer is in between every 1, 2, 3, 4, 5, 6, 7, 8, 9, 10, 15, 20, 50, or 100 acrylates of the polymer structure, or any integer between any two numbers listed. In some alternatives of the system, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives of the system, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives of the system, the hydrogel prodrug comprises a degradation time to release drugs for a period of at least or equal to 1 month, 2 months, 4 months, 8 months, 12 months, or any amount of time within a range defined by any two aforementioned values. In some alternatives of the system, the hydrogel prodrug comprises a targeting moiety. In some alternatives of the system, the targeting moiety is specific for a ligand on an organ, tissue or a cell. In some alternatives of the system, the targeting moiety is specific for a surface protein that is expressed during manifestation of a disease. In some alternatives of the system, the disease is cancer, cardiac disease, a neurological disease or a skin disease. In some alternatives of the system, the targeting moiety is specific for a tumor cell ligand on a tumor or a cancer antigen In some alternatives of the system, the tumor is a solid tumor. In some alternatives of the system, the system further comprises excipients. Excipients are used with the hydrogel prodrug or hydrogel prodrug system when they are used in injections, for example. In some alternatives, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, water, saline, dextrose, mannitol, lactose, lecithin, albumin, sodium glutamate, cysteine hydrochloride, and the like. In addition, if desired, the injectable pharmaceutical formulations can contain minor amounts of nontoxic auxiliary substances, such as wetting agents, pH buffering agents, and/or polyvinylpyrrolidone (PVP). In some alternatives of the system, the system further comprises a solution. In some alternatives, hydrogel prodrugs can be formulated in solutions, preferably in physiologically compatible buffers such as Hanks'solution, Ringer's solution, or physiological saline buffer. For such transmucosal administration, penetrants appropriate to the barrier to be permeated are used with the system. Such penetrants are generally known in the art. Use of pharmaceutically acceptable carriers to formulate the ingredients herein disclosed for the practice of the invention into dosages suitable for systemic administration is within the scope of the invention. With proper choice of carrier and suitable manufacturing practice, the hydrogel prodrug disclosed herein, in particular, those formulated for intravenous injection of hydrogel prodrug microparticles. In some alternatives, the system further comprises a bioadhesive to be used with the hydrogel prodrug. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values.

In some alternatives, a method of making a hydrogel prodrug composition comprising at least two drugs is provided. In some embodiments, the method of making a hydrogel prodrug composition comprising at least two drugs comprises providing a first hydrogel prodrug manufactured by anyone of the alternatives described herein, providing a second hydrogel prodrug manufactured by anyone of the alternatives described herein, blending the first and second hydrogel prodrugs to form a mixture; and cross-linking the first and second hydrogel prodrugs thereby forming a hydrogel prodrug composition comprising at least two drugs. The first and second hydrogel manufactured by any one of the alternatives herein. The method of making a hydrogel prodrug can comprise providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is a secondary amine group. In some alternatives, the at least one amine group comprises at least two secondary amine groups. In some alternatives, the method comprises reacting the at least one acrylate with the at least two secondary amine groups of the at least one drug. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly (ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values listed. In some alternatives, the reacting is performed at a temperature of at least or equal to 20° C., 25° C., 30° C. or 35° C. or any temperature within a range defined by any two of the aforementioned values listed. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one amine group. In some alternatives, the at least one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1: 1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the reacting step is performed for at least or equal to 1, 2, 3, 4, 5, 6, 7, 8, 9, 10, 12, 24, 36, 48 or 72 hours, or any time within a range defined by any two of the aforementioned values. In some alternatives the protein is insulin or lysozyme. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the spacer comprises isobutylamine. In some alternatives, the chemical spacer comprises at least two secondary amine groups. In some alternatives, the chemical spacer is provided at a ratio of chemical spacer to at least one drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates between any two aforementioned numbers. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. In some alternatives, the targeting moiety is specific for a ligand on a tumor. In some alternatives, the targeting moiety is specific for a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternative of the method of making a hydrogel prodrug composition, the first or second hydrogel prodrug comprises a peptide. In some alternative of the method of making a hydrogel prodrug composition—the first or second hydrogel prodrug comprises at least one drug. In some alternative of the method of making a hydrogel prodrug composition, the at least one drug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternative of the method of making a hydrogel prodrug composition, the first or second hydrogel prodrug comprises a second, third, fourth, fifth, sixth, seventh, eighth, ninth or tenth drug. In some alternative of the method of making a hydrogel prodrug composition, the second, third, fourth, fifth, sixth, seventh, eighth, ninth or tenth drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternative of the method of making a hydrogel prodrug composition, the first or second hydrogel prodrug comprises at least one acrylate. In some alternative of the method of making a hydrogel prodrug composition, the at least one acrylate is a diacrylate. In some alternative of the method of making a hydrogel prodrug composition, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternative of the method of making a hydrogel prodrug composition, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternative of the method of making a hydrogel prodrug composition, the second, third, fourth, fifth, sixth, seventh, eighth, ninth or tenth drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternative of the method of making a hydrogel prodrug composition, the first or second hydrogel prodrug further comprises a spacer group. In some alternative of the method of making a hydrogel prodrug composition, the spacer comprises at least primary amine group or at least one secondary amine group of the chemical spacer is attached to a carbon chain. In some alternative of the method of making a hydrogel prodrug composition, the carbon chain comprises at least or equal to 1, 5, 10, 15, 20, 25 or 30 carbon atoms or any number of carbon atoms within a range defined by any two of the aforementioned values. In some alternative of the method of making a hydrogel prodrug composition, the carbon chain comprises substituted heterocarbons, unsubstituted heterocarbons, saturated carbon bonds, unsaturated carbon bonds, branched cyclic carbon chains and/or unbranched cyclic carbon chains. In some alternative of the method of making a hydrogel prodrug composition, the branched or unbranched cyclic carbon chains are saturated. In some alternative of the method of making a hydrogel prodrug composition, the branched or unbranched cyclic carbon chains are unsaturated. In some alternative of the method of making a hydrogel prodrug composition, the branched or unbranched cyclic carbon chains comprise heteroatoms. In some alternative of the method of making a hydrogel prodrug composition, the first or second hydrogel prodrug comprises a polymer structure, wherein, the polymer structure is a poly (beta amino ester) (PBAE). In some alternative of the method of making a hydrogel prodrug composition, the first or second hydrogel prodrug comprises a polymer structure, wherein, the drug is incorporated into the polymer structure. In some alternative of the method of making a hydrogel prodrug composition, the polymer structure terminates with acrylate ends. In some alternative of the method of making a hydrogel prodrug composition, the drug is incorporated into the polymer structure, wherein, the drug is covalently linked between two acrylates. In some alternative of the method of making a hydrogel prodrug composition, the spacer is in between every 1, 2, 3, 4, 5, 6, 7, 8, 9, 10 15, 20, 50, or 100 acrylates of the polymer structure, or any integer between any two values listed. In some alternative of the method of making a hydrogel prodrug composition, the method further comprises providing a third, fourth, fifth, sixth, seventh, eighth, ninth or tenth hydrogel prodrug and blending the third, fourth, fifth, sixth, seventh, eighth, ninth or tenth hydrogel prodrug with the first and second hydrogel prodrug during the blending step. In some alternative of the method of making a hydrogel prodrug composition, the hydrogel prodrug composition comprises a degradation time to release drugs for a period of at least or equal to 1 hour, 2 hours, 4 hours, 8 hours, 16 hours, 32 hours or 64 hours or any amount of time within a range defined by any two aforementioned values. In some alternative of the method of making a hydrogel prodrug composition, the hydrogel prodrug composition comprises a degradation time to release drugs for a period of at least or equal to 1 day, 2 days, 4 days, 8 days, 16 days, 32 days, 64 days or 128 days, or any number of days within a range defined by any two aforementioned values. In some alternative of the method of making a hydrogel prodrug composition, the hydrogel prodrug composition comprises a degradation time to release drugs for a period of at least or equal to 1 month, 2 months, 4 months, 8 months, 12 months, or any amount of time within a range defined by any two aforementioned values. In some alternative of the method of making a hydrogel prodrug composition, the first, second, third, fourth, fifth, sixth, seventh, eighth, ninth and/or tenth hydrogel prodrug further comprises providing a targeting moiety. In some alternative of the method of making a hydrogel prodrug composition, the targeting moiety is specific for a ligand on an organ, tissue or a cell. In some alternative of the method of making a hydrogel prodrug composition, the targeting moiety is specific for a surface protein that is expressed during manifestation of a disease. In some alternative of the method of making a hydrogel prodrug composition, the disease is cancer, cardiac disease, a neurological disease or a skin disease. In some alternative of the method of making a hydrogel prodrug composition, the targeting moiety is specific for a tumor cell ligand on a tumor or a cancer antigen. In some alternative of the method of making a hydrogel prodrug composition, the tumor is a solid tumor. In some alternatives, a hydrogel prodrug composition manufactured by any one of the alternatives herein is provided. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. A hydrogel prodrug composition comprising at least two drugs is provided, which is made of any one of the alternative methods described herein. The hydrogel prodrug composition comprises at least two drugs. The at least two drugs comprise a nucleic acid analogue, amino ester-based drug, neurokinin 1 agonist, platinum-based, amine-containing chemotherapeutics, Anthracyclines, γ-Aminobutyric acid-derived drugs, Amino acid derivatives, Aminated benzoic acid derivatives, Proteins, antibiotic, statin, chemotherapeutic, antibody-drug conjugate, antibody or portion thereof, protein, oligopeptide, polypeptide, hormone, steroid, antipsychotic, anti-Alzheimer drug, Cholesterol regulator, Anesthetics, Analgesics, Antiepileptics, Antivirals, Anti-erectile dysfunction. Anti-arthritic drug, Contraceptives, Diabetes medication, Enzyme inhibitors, or Psychostimulants, Platelet aggregation inhibitors, an anti-HIV drug, an analgesic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives, the composition comprises a second, third, fourth, fifth, sixth, seventh, eighth, ninth or tenth drug. In some alternatives, the second, third, fourth, fifth, sixth, seventh, eighth, ninth or tenth drug is a nucleic acid analogue, amino ester-based drug, neurokinin 1 agonist, platinum-based, amine-containing chemotherapeutic s, Anthracyclines, γ-Aminobutyric acid-derived drugs, Amino acid derivatives, Aminated benzoic acid derivatives, Proteins, antibiotic, statin, chemotherapeutic, antibody-drug conjugate, antibody or portion thereof, protein, oligopeptide, polypeptide, hormone, steroid, antipsychotic, anti-Alzheimer drug, Cholesterol regulator, Anesthetics, Analgesics, Antiepileptics, Antivirals, Anti-erectile dysfunction. Anti-arthritic drug, Contraceptives, Diabetes medication, Enzyme inhibitors, or Psychostimulants, Platelet aggregation inhibitors, an anti-HIV drug, an analgesic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives, the first, second, third, fourth, fifth, sixth, seventh, eighth, ninth or tenth drug is a nucleic acid analogue, amino ester-based drug, neurokinin 1 agonist, platinum-based, amine-containing chemotherapeutic s, Anthracyclines, γ-Aminobutyric acid-derived drugs, Amino acid derivatives, Aminated benzoic acid derivatives, Proteins, antibiotic, statin, chemotherapeutic, antibody-drug conjugate, antibody or portion thereof, protein, oligopeptide, polypeptide, hormone, steroid, antipsychotic, anti-Alzheimer drug, Cholesterol regulator, Anesthetics, Analgesics, Antiepileptics, Antivirals, Anti-erectile dysfunction. Anti-arthritic drug, Contraceptives, Diabetes medication, Enzyme inhibitors, or Psychostimulants, Platelet aggregation inhibitors, an anti-HIV drug, an analgesic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives, the first, second, third, fourth, fifth, sixth, seventh, eighth, ninth or tenth drug is acyclovir, aprepitant, benzocaine, cisplatin, doxorubicin, gabapentin, ganciclovir, IgG, insulin, levothyroxine, oxaliplatin, pregabalin, procaine, tenofovir, tranexamic acid or 5-aminosalicylic acid. In some alternatives of the composition, the composition comprises a spacer.

A hydrogel prodrug composition comprising at least two drugs is provided, which is made of any one of the alternative methods described herein. The hydrogel prodrug composition comprises at least two drugs. The at least two drugs comprise a nucleic acid analogue, amino ester-based drug, neurokinin 1 agonist, platinum-based, amine-containing chemotherapeutics, Anthracyclines, γ-Aminobutyric acid-derived drugs, Amino acid derivatives, Aminated benzoic acid derivatives, Proteins, antibiotic, statin, chemotherapeutic, antibody-drug conjugate, antibody or portion thereof, protein, oligopeptide, polypeptide, hormone, steroid, antipsychotic, anti-Alzheimer drug, Cholesterol regulator, Anesthetics, Analgesics, Antiepileptics, Antivirals, Anti-erectile dysfunction. Anti-arthritic drug, Contraceptives, Diabetes medication, Enzyme inhibitors, or Psychostimulants, Platelet aggregation inhibitors, an anti-HIV drug, an analgesic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives, the composition comprises a second, third, fourth, fifth, sixth, seventh, eighth, ninth or tenth drug. In some alternatives, the second, third, fourth, fifth, sixth, seventh, eighth, ninth or tenth drug is a nucleic acid analogue, amino ester-based drug, neurokinin 1 agonist, platinum-based, amine-containing chemotherapeutics, Anthracyclines, γ-Aminobutyric acid-derived drugs, Amino acid derivatives, Aminated benzoic acid derivatives, Proteins, antibiotic, statin, chemotherapeutic, antibody-drug conjugate, antibody or portion thereof, protein, oligopeptide, polypeptide, hormone, steroid, antipsychotic, anti-Alzheimer drug, Cholesterol regulator, Anesthetics, Analgesics, Antiepileptics, Antivirals, Anti-erectile dysfunction. Anti-arthritic drug, Contraceptives, Diabetes medication, Enzyme inhibitors, or Psychostimulants, Platelet aggregation inhibitors, an anti-HIV drug, an analgesic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives, the first, second, third, fourth, fifth, sixth, seventh, eighth, ninth or tenth drug is a nucleic acid analogue, amino ester-based drug, neurokinin 1 agonist, platinum-based, amine-containing chemotherapeutic s, Anthracyclines, γ-Aminobutyric acid-derived drugs, Amino acid derivatives, Aminated benzoic acid derivatives, Proteins, antibiotic, statin, chemotherapeutic, antibody-drug conjugate, antibody or portion thereof, protein, oligopeptide, polypeptide, hormone, steroid, antipsychotic, anti-Alzheimer drug, Cholesterol regulator, Anesthetics, Analgesics, Antiepileptics, Antivirals, Anti-erectile dysfunction. Anti-arthritic drug, Contraceptives, Diabetes medication, Enzyme inhibitors, or Psychostimulants, Platelet aggregation inhibitors, an anti-HIV drug, an analgesic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives, the first, second, third, fourth, fifth, sixth, seventh, eighth, ninth or tenth drug is acyclovir, aprepitant, benzocaine, cisplatin, doxorubicin, gabapentin, ganciclovir, IgG, insulin, levothyroxine, oxaliplatin, pregabalin, procaine, tenofovir, tranexamic acid or 5-aminosalicylic acid. In some alternatives of the composition, the composition comprises a spacer.

In some alternatives, a method of ameliorating or inhibiting cancer, HIV, a viral infection, pain, a bacterial infection, a neurological disorder, hemorrhaging, multiple sclerosis, diabetes, high blood pressure, Alzheimer's, or inhibiting a fungal growth in a subject in need is provided. The method can comprise delivering the hydrogel prodrug manufactured by any one of the alternatives herein, the hydrogel prodrug system of any one of any one of the alternatives herein, the hydrogel prodrug composition manufactured by any one of the alternatives herein, the hydrogel prodrug of any one of the alternatives herein or the hydrogel prodrug composition of any one of the alternatives herein. In some alternatives of the method, the hydrogel prodrug or the hydrogel prodrug composition comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives of the method, the hydrogel prodrug or the hydrogel prodrug composition comprises acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives of the method, the hydrogel prodrug or the hydrogel prodrug composition is a compressed sheet, or incorporated into a scaffold, support or dressing. In some alternatives of the method, the hydrogel prodrug or the hydrogel prodrug composition is shaped into a capsule, a tablet, microparticle or an implantable device. In some alternatives of the method, the hydrogel prodrug or the hydrogel prodrug composition is delivered by applying the compressed sheet directly to a skin surface. In some alternatives of the method, the hydrogel prodrug or the hydrogel prodrug composition is applied directly over a wound. In some alternatives of the method, the hydrogel prodrug or the hydrogel prodrug composition is an implantable device, and wherein, the implantable device is placed subcutaneously at a site of a tumor to provide sustained chemotherapeutic release. In some alternatives of the method, the hydrogel prodrug or the hydrogel prodrug composition is a microparticle, and wherein, the microparticle is injected into a tissue. In some alternatives of the method, the subject is selected to receive treatment with a hydrogel prodrug for controlled release of a drug. In some alternatives of the method, the subject is suffering from cancer, HIV, a viral infection, pain, a bacterial infection, a neurological disorder, hemorrhaging, multiple sclerosis, diabetes, high blood pressure, Alzheimer's, or a fungal growth. In some alternatives of the method, the subject is mammalian. In some alternatives of the method, the subject is a cow, sheep, pig, horse, dog, cat, primate or a human. The method of making a hydrogel prodrug can comprise providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein the hydrogel prodrug comprises a backbone structure, wherein, the backbone structure comprises polymerized polymer prodrug. In some alternatives, the at least one amine group is a free primary amine group. In some alternatives, the at least one amine group is a secondary amine group. In some alternatives, the at least one amine group comprises at least two secondary amine groups. In some alternatives, the method comprises reacting the at least one acrylate with the at least two secondary amine groups of the at least one drug. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly (ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values listed. In some alternatives, the reacting is performed at a temperature of at least or equal to 20° C., 25° C., 30° C. or 35° C. or any temperature within a range defined by any two of the aforementioned values listed. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one amine group. In some alternatives, the at least one free amine group is a free primary amine group. In some alternatives, the at least one amine group of the second drug is a secondary amine group. In some alternatives, the second drug further comprises at least two secondary amine groups. In some alternatives, the at least one acrylate, and an amine sum total comprising a sum total of the at least primary and/or secondary amines of the at least one or two drugs are at a molar ratio of 1.05:1, 1.1: 1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregabiln, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the reacting step is performed for at least or equal to 1, 2, 3, 4, 5, 6, 7, 8, 9, 10, 12, 24, 36, 48 or 72 hours, or any time within a range defined by any two of the aforementioned values. In some alternatives the protein is insulin or lysozyme. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the spacer comprises isobutylamine. In some alternatives, the chemical spacer comprises at least two secondary amine groups. In some alternatives, the chemical spacer is provided at a ratio of chemical spacer to at least one drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates between any two aforementioned numbers. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. In some alternatives, the targeting moiety is specific for a ligand on a tumor. In some alternatives, the targeting moiety is specific for a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, a hydrogel prodrug manufactured by any one of these alternatives is provided. In some alternatives, hydrogel prodrug delivery system comprises the hydrogel prodrug manufactured by any one of the alternatives herein. In some embodiments, the method of making a hydrogel prodrug composition comprising at least two drugs comprises providing a first hydrogel prodrug manufactured by anyone of the alternatives described herein, providing a second hydrogel prodrug manufactured by anyone of the alternatives described herein, blending the first and second hydrogel prodrugs to form a mixture; and cross-linking the first and second hydrogel prodrugs thereby forming a hydrogel prodrug composition comprising at least two drugs. The first and second hydrogel manufactured by any one of the alternatives herein. The method of making a hydrogel prodrug can comprise providing at least one drug that comprises at least one amine group, providing at least one acrylate, reacting said at least one acrylate with the at least one amine group of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternative of the method of making a hydrogel prodrug composition, the first or second hydrogel prodrug comprises a peptide. In some alternative of the method of making a hydrogel prodrug composition—the first or second hydrogel prodrug comprises at least one drug. In some alternative of the method of making a hydrogel prodrug composition, the at least one drug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, antiarthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternative of the method of making a hydrogel prodrug composition, the first or second hydrogel prodrug comprises a second, third, fourth, fifth, sixth, seventh, eighth, ninth or tenth drug. In some alternative of the method of making a hydrogel prodrug composition, the second, third, fourth, fifth, sixth, seventh, eighth, ninth or tenth drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternative of the method of making a hydrogel prodrug composition, the first or second hydrogel prodrug comprises at least one acrylate. In some alternative of the method of making a hydrogel prodrug composition, the at least one acrylate is a diacrylate. In some alternative of the method of making a hydrogel prodrug composition, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternative of the method of making a hydrogel prodrug composition, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternative of the method of making a hydrogel prodrug composition, the second, third, fourth, fifth, sixth, seventh, eighth, ninth or tenth drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternative of the method of making a hydrogel prodrug composition, the first or second hydrogel prodrug further comprises a spacer group. In some alternative of the method of making a hydrogel prodrug composition, the spacer comprises at least primary amine group or at least one secondary amine group of the chemical spacer is attached to a carbon chain. In some alternative of the method of making a hydrogel prodrug composition, the carbon chain comprises at least or equal to 1, 5, 10, 15, 20, 25 or 30 carbon atoms or any number of carbon atoms within a range defined by any two of the aforementioned values. In some alternative of the method of making a hydrogel prodrug composition, the carbon chain comprises substituted heterocarbons, unsubstituted heterocarbons, saturated carbon bonds, unsaturated carbon bonds, branched cyclic carbon chains and/or unbranched cyclic carbon chains. In some alternative of the method of making a hydrogel prodrug composition, the branched or unbranched cyclic carbon chains are saturated. In some alternative of the method of making a hydrogel prodrug composition, the branched or unbranched cyclic carbon chains are unsaturated. In some alternative of the method of making a hydrogel prodrug composition, the branched or unbranched cyclic carbon chains comprise heteroatoms. In some alternative of the method of making a hydrogel prodrug composition, the first or second hydrogel prodrug comprises a polymer structure, wherein, the polymer structure is a poly (beta amino ester) (PBAE). In some alternative of the method of making a hydrogel prodrug composition, the first or second hydrogel prodrug comprises a polymer structure, wherein, the drug is incorporated into the polymer structure. In some alternative of the method of making a hydrogel prodrug composition, the polymer structure terminates with acrylate ends. In some alternative of the method of making a hydrogel prodrug composition, the drug is incorporated into the polymer structure, wherein, the drug is covalently linked between two acrylates. In some alternative of the method of making a hydrogel prodrug composition, the spacer is in between every 1, 2, 3, 4, 5, 6, 7, 8, 9, 10 15, 20, 50, or 100 acrylates of the polymer structure, or any integer between any two values listed. In some alternative of the method of making a hydrogel prodrug composition, the method further comprises providing a third, fourth, fifth, sixth, seventh, eighth, ninth or tenth hydrogel prodrug and blending the third, fourth, fifth, sixth, seventh, eighth, ninth or tenth hydrogel prodrug with the first and second hydrogel prodrug during the blending step. In some alternative of the method of making a hydrogel prodrug composition, the hydrogel prodrug composition comprises a degradation time to release drugs for a period of at least or equal to 1 hour, 2 hours, 4 hours, 8 hours, 16 hours, 32 hours or 64 hours or any amount of time within a range defined by any two aforementioned values. In some alternative of the method of making a hydrogel prodrug composition, the hydrogel prodrug composition comprises a degradation time to release drugs for a period of at least or equal to 1 day, 2 days, 4 days, 8 days, 16 days, 32 days, 64 days or 128 days, or any number of days within a range defined by any two aforementioned values. In some alternative of the method of making a hydrogel prodrug composition, the hydrogel prodrug composition comprises a degradation time to release drugs for a period of at least or equal to 1 month, 2 months, 4 months, 8 months, 12 months, or any amount of time within a range defined by any two aforementioned values. In some alternative of the method of making a hydrogel prodrug composition, the first, second, third, fourth, fifth, sixth, seventh, eighth, ninth and/or tenth hydrogel prodrug further comprises providing a targeting moiety. In some alternative of the method of making a hydrogel prodrug composition, the targeting moiety is specific for a ligand on an organ, tissue or a cell. In some alternative of the method of making a hydrogel prodrug composition, the targeting moiety is specific for a surface protein that is expressed during manifestation of a disease. In some alternative of the method of making a hydrogel prodrug composition, the disease is cancer, cardiac disease, a neurological disease or a skin disease. In some alternative of the method of making a hydrogel prodrug composition, the targeting moiety is specific for a tumor cell ligand on a tumor or a cancer antigen. In some alternative of the method of making a hydrogel prodrug composition, the tumor is a solid tumor. In some alternatives, a hydrogel prodrug composition manufactured by any one of the alternatives herein is provided. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values.

More Alternatives

Polymer Prodrug

In some alternatives, a method of making a polymer prodrug is provided. The method can have the following steps: providing at least one drug that comprises at least one free primary amine group, at least two secondary amine group, and/or any combination thereof, providing at least one acrylate and reacting said at least one acrylate with the at least one primary amine group or at least two secondary amine groups of the at least one drug, thereby producing at least one polymer prodrug, wherein, the reacting comprises a polymerization reaction and the drug comprises at least two secondary amine groups. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives—the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of at least or equal to 20° C., 25° C., 30° C. or 35° C. or any temperature within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one additional free primary amine group, or at least one additional secondary amine group and/or any combination thereof. In some alternatives, the second drug comprises at least two additional secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the reacting step is performed for at least or equal to 1, 2, 3, 4, 5, 6, 7, 8, 9, 10, 12, 24, 36, 48 or 72 hours, or any time within a range defined by any two of the aforementioned values. In some alternatives, the at least one drug acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values.

Making a Hydrogel Prodrug

In some alternatives, a method of making a hydrogel prodrug is provided. The method can comprise: providing at least one drug that comprises at least one amine group, providing at least one acrylate, reacting said at least one acrylate with the at least one amine group or at least two secondary amine groups of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is a secondary amine groups. In some alternatives, the drug further at least one amine group comprises at least two secondary amine groups. In some alternatives, the method comprises reacting the at least one acrylate with the at least two secondary amine groups of the at least one drug. In some alternatives, the drug comprises at least two secondary amine groups. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. any temperature within a range defined by any two of the aforementioned values. In some alternatives, the reacting is performed at a temperature of at least or equal to 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, antiarthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one additional free primary amine group, or at least one additional secondary amine group and/or any combination thereof. In some alternatives, the second drug comprises at least two additional secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the reacting step is performed for at least or equal to 1, 2, 3, 4, 5, 6, 7, 8, 9, 10, 12, 24, 36, 48 or 72 hours, or any time within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. The method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to at least one drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. The method can comprise providing at least one drug that comprises at least one free primary amine group, at least two secondary amine group, and/or any combination thereof, providing at least one acrylate, reacting said at least one acrylate with the at least one primary amine group or at least two secondary amine groups of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the drug comprises at least two secondary amine groups. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of at least or equal to 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one additional free primary amine group, or at least one additional secondary amine group and/or any combination thereof. In some alternatives, the second drug comprises at least two additional secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregablin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregablin, procaine, tenofovir, tranexamic acid or 5-aminosalicylic acid. In some alternatives, the reacting step is performed for at least or equal to 1, 2, 3, 4, 5, 6, 7, 8, 9, 10, 12, 24, 36, 48 or 72 hours, or any time within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregablin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to at least one drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the hydrogel prodrug is formulated to release for 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. In some alternatives, a hydrogel prodrug delivery system comprises any one of the hydrogel prodrug manufactured by any one of the alternatives provided herein.

A Hydrogel Prodrug Delivery System

In some alternatives, a hydrogel prodrug delivery system is provided. The hydrogel prodrug delivery system can comprise the hydrogel prodrug manufactured by anyone of the alternatives described herein. The method can comprise providing at least one drug that comprises at least one free primary amine group, at least two secondary amine group, and/or any combination thereof, providing at least one acrylate, reacting said at least one acrylate with the at least one primary amine group or at least two secondary amine groups of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the drug comprises at least two secondary amine groups. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values listed. In some alternatives, the reacting is performed at a temperature of at least or equal to 20° C., 25° C., 30° C. or 35° C. or any temperature within a range defined by any two of the aforementioned values listed. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one additional free primary amine group, or at least one additional secondary amine group and/or any combination thereof. In some alternatives, the second drug comprises at least two additional secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the reacting step is performed for at least at least or equal to 1, 2, 3, 4, 5, 6, 7, 8, 9, 10, 12, 24, 36, 48 or 72 hours, or any time within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to at least one drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates between any two aforementioned numbers. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any number of time in between any 2 aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. The method can comprise providing at least one drug that comprises at least one free primary amine group, at least two secondary amine group, and/or any combination thereof, providing at least one acrylate, reacting said at least one acrylate with the at least one primary amine group or at least two secondary amine groups of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the drug comprises at least two secondary amine groups. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly (ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values listed. In some alternatives, the reacting is performed at a temperature of at least or equal to 20° C., 25° C., 30° C. or 35° C. or any temperature within a range defined by any two of the aforementioned values listed. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one additional free primary amine group, or at least one additional secondary amine group and/or any combination thereof. In some alternatives, the second drug comprises at least two additional secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the reacting step is performed for at least or equal to 1, 2, 3, 4, 5, 6, 7, 8, 9, 10, 12, 24, 36, 48 or 72 hours, or any time within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to at least one drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates between any two aforementioned numbers. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the hydrogel prodrug is formulated to release for 1, 2, 3, 4, 5, 6, 7, 8, 9, 10, 20, 30, 40, 50, 60, 80, 80, 90 or 100 hours or any number of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. In some alternatives of the system, the hydrogel prodrug comprises a peptide. In some alternatives of the system, the hydrogel prodrug comprises at least one drug. In some alternatives of the system, the at least one drug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the system, the hydrogel prodrug comprises a second, third, fourth, fifth, sixth, seventh, eighth, ninth or tenth drug. In some alternatives of the system, the second, third, fourth, fifth, sixth, seventh, eighth, ninth or tenth drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the system, the hydrogel prodrug comprises at least one acrylate. In some alternatives of the system, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives of the system, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives of the system, the cyclic carbon chains comprise saturated bonds, unsaturated bonds and/or heteroatoms. In some alternatives of the system, the acrylate comprises at least two acrylate groups and is a diacrylate. In some alternatives of the system, the diacrylate is poly (ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives of the system, the acrylate comprises a molecular weight of 170, 250, 575, 700, 1000, 2000, 3500, 5000, 10000, g/mol, or any other molecular weight within a range defined by any two of the aforementioned values. In some alternatives of the system, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives of the system, the hydrogel prodrug further comprises a spacer. In some alternatives of the system, the spacer comprises a hydrophilic group, such as a hydroxyl group. In some alternatives of the system, the spacer comprises a carbon chain. In some alternatives of the system, the carbon chain comprises at least or equal to 1, 5, 10, 15, 20, 25 or 30 carbon atoms or any number of carbon atoms within a range defined by any two of the aforementioned values. In some alternatives of the system, the carbon chain comprises substituted heterocarbons, unsubstituted heterocarbons, saturated carbon bonds, unsaturated carbon bonds, branched cyclic carbon chains and/or unbranched cyclic carbon chains. In some alternatives of the system, the branched or unbranched cyclic carbon chains are saturated. In some alternatives of the system, the branched or unbranched cyclic carbon chains are unsaturated. In some alternatives of the system, the branched or unbranched cyclic carbon chains comprise heteroatoms. In some alternatives of the system, the hydrogel prodrug is a compressed sheet, film, incorporated into a scaffold, support or a dressing. In some alternatives of the system, the hydrogel prodrug is shaped into a tablet, an implantable device, microparticle or a pill. In some alternatives of the system, the hydrogel prodrug comprises a polymer structure, wherein, the polymer structure is a poly (beta amino ester) (PBAE). In some alternatives of the system, the hydrogel prodrug comprises a polymer structure, wherein, the primary amine of the drug is incorporated into the polymer structure by conjugate addition to a vinyl group of the at least one acrylate molecules, resulting in a tertiary amine within the polymer backbone, or wherein, two secondary amines of a drug molecule are each incorporated into the polymer structure by conjugate addition to the vinyl group of an acrylate molecule, resulting in two tertiary amines incorporated into the polymer backbone. In some alternatives of the system, the polymer structure terminates with acrylate ends. In some alternatives of the system, the drug is incorporated into the polymer structure and wherein, the drug is covalently linked between two acrylates. In some alternatives of the system, the spacer is in between every 1, 2, 3, 4, 5, 6, 7, 8, 9, 10, 15, 20, 50, or 100 acrylates of the polymer structure, or any integer within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values.

A Method of Making a Hydrogel Prodrug Composition

In some alternatives, a method of making a hydrogel prodrug composition comprising at least two drugs is provided: providing at least one drug that comprises at least one amine group, providing at least one acrylate, reacting said at least one acrylate with the at least one amine group or at least two secondary amine groups of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the at least one amine group is a free primary amine group. In some alternatives, the at least one amine group is a secondary amine groups. In some alternatives, the drug further at least one amine group comprises at least two secondary amine groups. In some alternatives, the method comprises reacting the at least one acrylate with the at least two secondary amine groups of the at least one drug. In some alternatives, the drug comprises at least two secondary amine groups. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly (ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of at least or equal to 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one additional free primary amine group, or at least one additional secondary amine group and/or any combination thereof. In some alternatives, the second drug comprises at least two additional secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutic, anthracycline, γ-aminobutyric acid-derived drug, amino acid derivative, aminated benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the reacting step is performed for at least or equal to 1, 2, 3, 4, 5, 6, 7, 8, 9, 10, 12, 24, 36, 48 or 72 hours, or any time within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. The method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the second drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to at least one drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. The method can comprise providing at least one drug that comprises at least one free primary amine group, at least two secondary amine group, and/or any combination thereof, providing at least one acrylate, reacting said at least one acrylate with the at least one primary amine group or at least two secondary amine groups of the at least one drug, thereby producing at least one polymer prodrug, wherein, the reacting comprises a polymerization reaction and cross-linking said at least one polymer prodrug in the presence of a free radical initiator in a reaction mixture, thereby making the hydrogel prodrug, wherein, the hydrogel prodrug comprises a backbone structure, wherein, the backbone structure comprises polymerized polymer prodrug. In some alternatives, the drug comprises at least two secondary amine groups. In some alternatives, the method further comprises providing at least one primary amine and/or at least one secondary amine. In some alternatives, the at least one acrylate comprises at least one acrylate group. In some alternatives, the at least one acrylate group is bound by an ester linkage to an opposing termini of a carbon chain, wherein, the carbon chain comprises at least or equal to 1, 10, 20, 30, 40, 50, 60, 70, 80, 90 or 100 carbon atoms, or any number of carbon atoms within a range defined by any two of the aforementioned values. In some alternatives, the carbon chain comprises substituted heteroatoms, unsubstituted heteroatoms, unsaturated carbon-carbon bonds, saturated carbon-carbon bonds, branched substitutions, unbranched substitutions and/or cyclic carbon chains. In some alternatives, the cyclic carbon chains comprise saturated bonds, unsaturated bonds and/or heteroatoms. In some alternatives, the acrylate comprises two acrylate groups and is a diacrylate. In some alternatives, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives, the at least one acrylate and the at least one free primary amine or at least two secondary amines of the at least one drug are at a molar ratio of 1.05:1, 1.1:1, 1.2:1, 1.5:1, 2:1 3:1, 4:1 or 5:1 acrylate to drug or any other ratio within a range defined by any two of the aforementioned values. In some alternatives, the acrylate comprises a molecular weight of at least or equal to 170, 250, 575, 700, 1000, 2000, 3500, 5000, 10000, g/mol, or any other molecular weight within a range defined by any two of the aforementioned values. In some alternatives, the reacting step is performed at a temperature of at least or equal to 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. or 120° C. or any temperature within a range defined by any two of the aforementioned values. In some alternatives, the reacting is performed at a temperature of at least or equal to 20° C., 25° C., 30° C. or 35° C. or any temperature within a range defined by any two of the aforementioned values. In some alternatives, the cross-linking is performed in the presence of a catalyst. In some alternatives, the catalyst is TEMED. In some alternatives, the TEMED is at a 1%, 2%, 3%, 4%, 5%, 6%, 7%, 8%, 9% or 10% w/w of TEMED to reaction mixture or any w/w percent within a range defined by any two of the aforementioned values. In some alternatives, the free radical initiator is ammonium persulfate. In some alternatives, the concentration of ammonium persulfate in the reaction is 1%, 2%, 3%, 4%, 5%, 6%, 7%, 8%, 9% or 10% w/w of ammonium sulfate to reaction mixture or any concentration within a range defined by any two of the aforementioned values. In some alternatives, the cross-linking is performed in the presence of a UV radiation source. In some alternatives, the free radical initiator is a light-activated free radical initiator. In some alternatives, the light-activated free radical initiator is DMPA. In some alternatives, the DMPA is at a concentration is at 0.2%, 0.4%, 0.6%, 0.8% or 1% v/v of DMPA in the reaction mixture or any concentration within a range defined by any two of the aforementioned values. In some alternatives, the cross-linking is performed in the presence of a UV radiation source for at least or equal to 1, 2, 3, 4, 5, 6, 7, 8, 9 or 10 minutes or any amount of time within a range defined by any two of the aforementioned values. In some alternatives, the reacting step comprises an addition reaction between the at least one free primary amine group of at least one drug or the at least one secondary amine group of the at least one drug with the at least one acrylate. In some alternatives, the at least one free primary amine group or at least one secondary amine group is present on a peptide. In some alternatives, 2, 3, 4, 5, 6, 7, 8, 9 or 10 drugs are polymerized to the at least one acrylate, thereby producing at least 2, 3, 4, 5, 6, 7, 8, 9 or 10 prodrugs. In some alternatives, the 2, 3, 4, 5, 6, 7, 8, 9 or 10 drugs comprise at least one primary amine group or at least one secondary amine groups. In some alternatives, the 2, 3, 4, 5, 6, 7, 8, 9 or 10 drugs comprise at least two secondary amine groups. In some alternatives, the at least one primary amine group or the at least one secondary amine groups of the 2, 3, 4, 5, 6, 7, 8, 9, or 10 drugs participates in an addition reaction with the at least one acrylate. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the method further comprises providing a second drug, wherein, the second drug comprises at least one additional free primary amine group, or at least one additional secondary amine group and/or any combination thereof. In some alternatives, the second drug comprises at least two additional secondary amine groups. In some alternatives, the at least one acrylate, and an amine sum total comprising a sum total of the at least primary and/or secondary amines of the at least one or two drugs are at a molar ratio of 1.05:1, 1.1:1, 1.2:1, 1.5:1, 2:1 3:1, 4:1 or 5:1 diacrylate:amine sum total or any other ratio within a range defined by any two of the aforementioned values. In some alternatives, the second drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the reacting step is performed for at least or equal to 1, 2, 3, 4, 5, 6, 7, 8, 9, 10, 12, 24, 36, 48 or 72 hours, or any time within a range defined by any two of the aforementioned values. In some alternatives, the method further comprises purifying the hydrogel prodrug. In some alternatives, the method further comprises stopping the cross-linking step before the purification step. In some alternatives, the stopping is performed by adding hydrochloric acid. In some alternatives, the method further comprises stopping the polymerization action before the purification step, wherein, the method is stopped by lowering the temperature to at least or equal to 4° C., 5° C., 6° C., 7° C., 8° C., 9° C. or 10° C. or any temperature within a range defined by any two of the aforementioned values, or any temperature lower than the aforementioned values. In some alternatives, the method reaction further comprises monitoring the cross-linking step, wherein, the monitoring is performed by obtaining a sample of the reaction mixture and subjecting the reaction mixture to FTIR. In some alternatives, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the method further comprises providing a chemical spacer comprising at least one free primary amine group or at least one secondary amine group, wherein, the chemical spacer is a spacer in the backbone structure of the hydrogel prodrug. In some alternatives, the chemical spacer comprises at least two secondary amine groups. In some alternatives, the chemical spacer is provided at a ratio of the chemical spacer to at least one drug ratio of 1:1, 2: 1, 5:1, 9:1, 10:1, 20:1, 30:1, 40:1, 50:1, 60:1, 70:1, 80:1, 90:1, 99:1 or 100:1 or any other ratio of chemical spacer to at least one drug in between any two aforementioned ratios. In some alternatives, the chemical spacer comprises a hydrophilic group, such as a hydroxyl group. In some alternatives, the at least primary amine group of the chemical spacer or at least one secondary amine group of the chemical spacer is attached to a carbon chain. In some alternatives, the carbon chain comprise at least or equal to 1, 5, 10, 15, 20, 25 or 30 carbon atoms or any number of carbon atoms within a range defined by any two of the aforementioned values. In some alternatives, the carbon chain comprises substituted heterocarbons, unsubstituted heterocarbons, saturated carbon bonds, unsaturated carbon bonds, branched cyclic carbon chains and/or unbranched cyclic carbon chains. In some alternatives, the branched or unbranched cyclic carbon chains are saturated. In some alternatives, the branched or unbranched cyclic carbon chains are unsaturated. In some alternatives, the branched or unbranched cyclic carbon chains comprise heteroatoms. In some alternatives, the chemical spacer is added to the at least one acrylate prior to reacting the at least one drug with the at least one acrylate, thereby forming a polymer spacer. In some alternatives, the chemical spacer, at least one acrylate, and at least one drug are all reacted simultaneously to form at least one polymer prodrug and at least one polymer spacer in the reacting step. In some alternatives, the cross-linking step comprises cross-linking said at least one polymer prodrug and at least one polymer spacer in the presence of a free radical initiator in a reaction mixture, thereby making the hydrogel prodrug, wherein, the hydrogel prodrug comprises a backbone structure, wherein, the backbone structure comprises the polymerized polymer prodrug and the polymer spacer. In some alternatives, the at least one drug is dissolved in a solvent prior to adding the at least one drug to the reacting step. In some alternatives, the solvent is a polar solvent, such as water. In some alternatives, the solvent does not contain a buffer with an amine group such as Tris. In some alternatives, the solvent is an organic solvent. In some alternatives, the organic solvent is THF, diethyl ether, glyme, hexanes, methanol, ethanol, isopropanol, methylene chloride, chloroform, carbon tetrachloride, dimethylformamide, acetonitrile, DMSO, benzene or toluene. In some alternatives, the hydrogel prodrug comprises a polymer structure, wherein, the polymer structure is a poly (beta-amino ester) (PBAE). In some alternatives, the primary amine of the drug is incorporated into the polymer structure by conjugate addition to a vinyl group of the at least one acrylate molecule, resulting in a tertiary amine within the polymer backbone, or wherein, two secondary amines of a drug molecule are each incorporated into the polymer structure by conjugate addition to a vinyl group of an acrylate molecule, resulting in two tertiary amines incorporated into the polymer backbone. In some alternatives, the reacting step comprises an addition reaction wherein, the at least one free primary amine group or at least one secondary amine of the drug participate in an addition reaction with two acrylates, resulting in a polymer prodrug, and the hydrogel prodrug comprises a polymer structure wherein, the drug is incorporated into the backbone structure and the at least one polymer prodrug is cross-linked to form a hydrogel prodrug by covalently linking the terminal acrylate groups of separate polymer prodrug molecules. In some alternatives, after each polymer prodrug is bound in the backbone structure, the polymer spacer is bound between every 1, 2, 3, 4, 5, 6, 7, 8, 9, 10 15, 20, 50, or 100 acrylates of the polymer structure, or any number of acrylates within a range defined by any two of the aforementioned values. In some alternatives, the polymer structure terminates with acrylate ends. In some alternatives, the polymer prodrug comprises a molecular weight of at least or equal to 1,000, 5,000, 10,000, 20,000, 30,000, 40,000, 50,000, 60,000, 70,000, 80,000, 90,000 or 100,000 Da or any molecular weight within a range defined by any two of the aforementioned values. In some alternatives, the method further comprises washing the hydrogel prodrug with ethanol or another solvent to remove unwanted or unreacted material. In some alternatives, the method further comprises stretching or compressing the hydrogel prodrug to a desired shape. In some alternatives, the cross-linking step is performed in a mold such that the hydrogel prodrug comprises a final desired shape, such as a tablet, a film, a dressing or a scaffold. In some alternatives, the hydrogel prodrug is compressed into a film for application to a surface area, such as a dressing or shaped into a scaffold or support. In some alternatives, the hydrogel prodrug is processed into a solid capsule, implant, microparticle or a pill. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. In some alternatives, the hydrogel prodrug comprises a degradation time to release drugs for a period of at least or equal to 1 hour, 2 hours, 4 hours, 8 hours, 16 hours, 32 hours or 64 hours or any amount of time within a range defined by any two aforementioned values. In some alternatives, the hydrogel prodrug comprises a degradation time to release drugs for a period of at least or equal to 1 day, 2 days, 4 days, 8 days, 16 days, 32 days, 64 days or 128 days, or any number of days within a range defined by any two aforementioned values. In some alternatives, the hydrogel prodrug comprises a degradation time to release drugs for a period of at least or equal to 1 month, 2 months, 4 months, 8 months, 12 months, or any amount of time within a range defined by any two aforementioned values. In some alternatives, the method further comprises providing a targeting moiety and incorporating or linking the targeting moiety to the at least one polymer prodrug. In some alternatives, the targeting moiety is specific for a ligand on an organ, tissue or a cell. In some alternatives, the targeting moiety is specific for a surface protein that is expressed during manifestation of a disease. In some alternatives, the disease is cancer, cardiac disease, a neurological disease or a skin disease. In some alternatives, the targeting moiety is specific for a tumor cell ligand on a tumor or a cancer antigen. In some alternatives, the tumor is a solid tumor. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values. In some alternatives, a hydrogel prodrug delivery system comprises any one of the hydrogel prodrug manufactured by any one of the alternatives provided herein. In some alternatives of the method, the first or second polymer prodrug comprises a peptide. In some alternatives of the method, the first or second polymer prodrug comprises at least one drug. In some alternatives of the method, the at least one drug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the method, the first or second polymer prodrug comprises a second, third, fourth, fifth, sixth, seventh, eighth, ninth or tenth drug. In some alternatives of the method, the second, third, fourth, fifth, sixth, seventh, eighth, ninth or tenth drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the method, the first or second polymer prodrug comprises at least one acrylate. In some alternatives of the method, the at least one acrylate is a diacrylate. In some alternatives of the method, the diacrylate is poly(ethylene glycol) 250 diacrylate (PEG250DA) poly(ethylene glycol) 400 diacrylate (PEG400DA), poly(ethylene glycol) 575 diacrylate (PEG575DA), triethylene glycol diacrylate (TEGDA) or diethylene glycol diacrylate (DEGDA). In some alternatives of the method, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives of the method, the first or second polymer prodrug further comprises a spacer group. In some alternatives of the method, the spacer comprises at least primary amine group or at least one secondary amine group of the chemical spacer is attached to a carbon chain. In some alternatives of the method, the carbon chain comprises at least or equal to 1, 5, 10, 15, 20, 25 or 30 carbon atoms or any number of carbon atoms within a range defined by any two of the aforementioned values. In some alternatives of the method, the carbon chain comprises substituted heterocarbons, unsubstituted heterocarbons, saturated carbon bonds, unsaturated carbon bonds, branched cyclic carbon chains and/or unbranched cyclic carbon chains. In some alternatives of the method, the branched or unbranched cyclic carbon chains are saturated. In some alternatives of the method, the branched or unbranched cyclic carbon chains are unsaturated. In some alternatives of the method, the branched or unbranched cyclic carbon chains comprise heteroatoms. In some alternatives of the method, the first or second polymer prodrug comprises a polymer structure, wherein, the polymer structure is a poly (beta amino ester) (PBAE). In some alternatives of the method, the first or second polymer prodrug comprises a polymer structure, wherein, the drug is incorporated into the polymer structure. In some alternatives of the method, the polymer structure terminates with acrylate ends. In some alternatives of the method, the drug is incorporated into the polymer structure, wherein, the drug is covalently linked between two acrylates. In some alternatives of the method, the spacer is in between every 1, 2, 3, 4, 5, 6, 7, 8, 9, 10 15, 20, 50, or 100 acrylates of the polymer structure, or any integer within a range defined by any two of the aforementioned values. In some alternatives of the method, the method further comprising providing a third, fourth, fifth, sixth, seventh, eighth, ninth or tenth polymer prodrug and blending the third, fourth, fifth, sixth, seventh, eighth, ninth or tenth polymer prodrug with the first and second hydrogel prodrug during the blending step. In some alternatives a hydrogel prodrug composition is provided, wherein the hydrogel prodrug composition is manufactured by these alternative methods. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values.

Methods of Treatment

In some alternatives, a method of ameliorating or inhibiting cancer, HIV, a virus, pain, a bacterial infection, a neurological disorder, hemorrhaging, multiple sclerosis, diabetes, high blood pressure, Alzheimer's, or inhibiting a fungal growth in a subject in need is provided. The method can comprise delivering the hydrogel prodrug system of any one of the alternatives herein, the hydrogel prodrug manufactured by anyone of the alternatives described herein or the hydrogel prodrug composition of anyone of the alternatives described herein. The method can comprise providing a first polymer prodrug manufactured by anyone of the alternatives described herein, providing a second polymer prodrug manufactured by anyone of the alternatives described herein, blending the first and second polymer prodrugs to form a mixture and cross-linking the first and second polymer prodrugs thereby forming a hydrogel prodrug composition comprising at least two drugs. In some alternatives of the method, the first or second polymer prodrug comprises a peptide. In some alternatives of the method, the first or second polymer prodrug comprises at least one drug. In some alternatives of the method, the at least one drug comprises a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the method, the first or second polymer prodrug comprises a second, third, fourth, fifth, sixth, seventh, eighth, ninth or tenth drug. In some alternatives of the method, the second, third, fourth, fifth, sixth, seventh, eighth, ninth or tenth drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives of the method, the first or second polymer prodrug comprises at least one acrylate. In some alternatives of the method, the at least one acrylate is a diacrylate. In some alternatives of the method, the diacrylate is poly(ethylene glycol) 250 diacrylate (PEG250DA) poly(ethylene glycol) 400 diacrylate (PEG400DA), poly (ethylene glycol) 575 diacrylate (PEG575DA), triethylene glycol diacrylate (TEGDA) or diethylene glycol diacrylate (DEGDA). In some alternatives of the method, the at least one drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives of the method, the first or second polymer prodrug further comprises a spacer group. In some alternatives of the method, the spacer comprises at least primary amine group or at least one secondary amine group of the chemical spacer is attached to a carbon chain. In some alternatives of the method, the carbon chain comprises at least or equal to 1, 5, 10, 15, 20, 25 or 30 carbon atoms or any number of carbon atoms within a range defined by any two of the aforementioned values. In some alternatives of the method, the carbon chain comprises substituted heterocarbons, unsubstituted heterocarbons, saturated carbon bonds, unsaturated carbon bonds, branched cyclic carbon chains and/or unbranched cyclic carbon chains. In some alternatives of the method, the branched or unbranched cyclic carbon chains are saturated. In some alternatives of the method, the branched or unbranched cyclic carbon chains are unsaturated. In some alternatives of the method, the branched or unbranched cyclic carbon chains comprise heteroatoms. In some alternatives of the method, the first or second polymer prodrug comprises a polymer structure, wherein, the polymer structure is a poly (beta amino ester) (PBAE). In some alternatives of the method, the first or second polymer prodrug comprises a polymer structure, wherein, the drug is incorporated into the polymer structure. In some alternatives of the method, the polymer structure terminates with acrylate ends. In some alternatives of the method, the drug is incorporated into the polymer structure, wherein, the drug is covalently linked between two acrylates. In some alternatives of the method, the spacer is in between every 1, 2, 3, 4, 5, 6, 7, 8, 9, 10 15, 20, 50, or 100 acrylates of the polymer structure, or any integer within a range defined by any two of the aforementioned values. In some alternatives of the method, the method further comprising providing a third, fourth, fifth, sixth, seventh, eighth, ninth or tenth polymer prodrug and blending the third, fourth, fifth, sixth, seventh, eighth, ninth or tenth polymer prodrug with the first and second hydrogel prodrug during the blending step. In some alternatives, the hydrogel prodrug composition is manufactured by these alternative methods.

In some alternatives, the hydrogel prodrug or the hydrogel prodrug composition is a compressed sheet, or incorporated into a scaffold, support or dressing. In some alternatives, the hydrogel prodrug or the hydrogel prodrug composition is shaped into a capsule, a tablet, microparticle or an implantable device. In some alternatives, the hydrogel prodrug or the hydrogel prodrug composition is delivered by applying the compressed sheet directly to a skin surface. In some alternatives, the hydrogel prodrug or the hydrogel prodrug composition is applied directly over a wound. In some alternatives, the hydrogel prodrug or the hydrogel prodrug composition is an implantable device, and wherein, the implantable device is placed subcutaneously at a site of a tumor to provide sustained chemotherapeutic release. In some alternatives, the hydrogel prodrug or the hydrogel prodrug composition is a microparticle, and wherein, the microparticle is injected into a tissue. In some alternatives, the hydrogel prodrug is formulated to release for at least or equal to 1, 2, 3, 4, 5, 6, 7, 8, 9, 10, 20, 30, 40, 50, 60, 80, 80, 90 or 100 hours or any amount of time within a range defined by any two of the aforementioned values. In some alternatives, the hydrogel prodrug is formulated to release for at least or equal to 1, 2, 3, 4, 5, 6, 7, 8, 9, 10, 20, 30, 40, 50, 60, 80, 80, 90 or 100 days or any amount of time within a range defined by any two of the aforementioned values. In some alternatives, the hydrogel prodrug is formulated to release for at least or equal to 1, 2, 3, 4, 5, 6, 7, 8, 9, 10, 11 or 12 months or any amount of time within a range defined by any two of the aforementioned values.

Additional Alternatives

Previously described polymer controlled drug delivery systems can also lead to the release of drugs that are modified, such as a modification by PEGylation, which would necessitate a complex regulatory pathway as these modifications (i.e. PEGylation) may alter the bioactivity of the released drug.

Described herein is a polymer controlled drug delivery system that comprises a copolymer consisting of a drug ester and a biodegradable polymer (e.g., poly(beta amino ester)), connected via a linear molecule (e.g., PEG). This polymer can then be cross-linked into a hydrogel which can fully degrade at the ester linkages. One benefit of this polymer controlled drug delivery system is that the polymer will fully degrade at ester linkages to release native drug even in its crosslinked form. This has the benefit of releasing native drug, which is not linked to a linear or branched molecule (e.g., PEG).

Desirable features of the methods described herein over the previously described polymer controlled drug delivery system include: 1) the poly(beta amino ester) part is formed in a separate reaction, therefore pre-formed biodegradable spacer components are provided. In the previously described polymer controlled drug delivery system, the method of making the polymer controlled drug delivery system comprised reacting all of the components at the same time to form a random copolymer containing drug modified at its amino group(s); 2) the poly(beta amino ester) may be replaced with any biodegradable polymer, because the bifunctional linear molecule interfaces with the drug. In the previously described polymer controlled drug delivery system, the initial polymerization reaction also utilized drug molecules, so the chemistry of the polymer backbone could not be changed. 3) The ester bond formed in the reactions of the method of making the polymer controlled drug delivery system is fully hydrolysable, which will result in native drug being released from the system. In the previously described polymer controlled drug delivery system, the drugs released were still PEGylated or were attached by a spacer or linker molecule which may alter the bioactivity of the released drug.

In some alternatives, a method of making a hydrogel prodrug is provided, wherein the hydrogel prodrug is capable of biodegrading or is configured to biodegrade via hydrolysis and releasing at least one drug that is in a native, unaltered form of the drug, the method comprising: a) providing at least one molecule that comprises at least one amine group (A); b) providing at least one diacrylate (D); c) reacting said at least one diacrylate with said at least one amine group of the at least one molecule, thereby producing at least one non-drug-containing poly (beta amino ester) (PBAE); d) providing a linear molecule (M), wherein the linear molecule (M) is terminated at one end with a carboxylic acid and terminated at the other end with a group reactive to the poly(beta amino ester); e) reacting the poly (beta amino ester) (PBAE) with the linear molecule (M) to form a carboxylic acid terminated polymer chain, wherein the carboxylic acid terminated polymer chain comprises a structure [M-D-[A-D]n-M]m or [M-A-[D-A]n-M]m; f) providing a drug (X), wherein the drug comprises at least two hydroxyl groups; g) reacting the drug (X) with the carboxylic acid terminated polymer chain formed in step e), wherein the carboxylic acid terminated polymer chain is in a molar excess over the drug; thereby producing a copolymer comprising structure comprising: [M-D-[A-D]n-M-X]m-M, wherein the structure comprises at least one or more reactive terminal groups and ester bonds are formed; and optionally h) performing a cross linking reaction between the polymer produced in step g) with a molecule comprising 3 or more reactive hydroxyl groups or any other molecule with three or more groups capable of reacting with the at least one or more reactive terminal groups of the polymer produced in step g). In some alternatives, the reacting of step g) or the cross linking reaction of step h) produces a copolymer comprising a drug ester of the drug in step f) and the at least one non-drug-containing poly (beta amino ester) (PBAE) connected by the linear molecule of step d), and wherein the copolymer comprises ester linkages. In some alternatives, the copolymer is cross linked into a hydrogel, wherein the hydrogel is capable of degrading or is configured to degrade at the ester linkages to release native drug. In some alternatives, the group reactive to the at least one non-drug-containing poly (beta amino ester) (PBAE) of the linear molecule comprises an amine, acrylate or methacrylate. In some alternatives, the at least one non-drug-containing poly (beta amino ester) (PBAE) terminates with a diacrylate and wherein the diacrylate reacts with the amine of the linear molecule or wherein the group reactive to the at least one non-drug-containing poly (beta amino ester) (PBAE) of the linear molecule comprises an acrylate or methacrylate and wherein the at least one non-drug-containing poly (beta amino ester) (PBAE) terminates with an amine, wherein the amine reacts with the acrylate or methacrylate of the linear molecule. In some alternatives, the diacrylate is in a molar excess over the at least one molecule that comprises the at least one amine group in step a) or wherein the at least one amine group in step a) is in a molar excess over the at least at least one diacrylate (D). In some alternatives, the structure of the at least one non-drug-containing poly (beta amino ester) (PBAE) is D-[A-D]n or is A-[D-A]n. In some alternatives, the linear molecule is PEG. In some alternatives, the at least one amine group is a free primary amine group, a secondary amine group or comprises at least two secondary amine groups. In some alternatives, the drug (X) comprises 3 or more hydroxyl groups, and wherein the only steps a)-f) are performed. In some alternatives, the at least one drug (X) is a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, antiarthritic drug, contraceptive, diabetes medication, enzyme inhibitor, psycho stimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir. In some alternatives, in step (d) a branched molecule is provided, instead of a linear molecule, wherein the branched molecule is terminated at one end with a carboxylic acid and terminated at the other end with a group reactive to the at least one acrylate or the at least one amine of the biodegradable polymer.

In some alternatives, a method of making a hydrogel prodrug is provided, wherein the hydrogel prodrug is capable of biodegrading or is configured to degrade via hydrolysis and releasing at least one drug that is in a native, unaltered form of the drug, the method comprising: a) providing at least one biodegradable polymer, wherein the at least one biodegradable polymer terminates with at least one acrylate or at least one amine; b) providing a linear molecule (M), wherein the linear molecule (M) is terminated at one end with a carboxylic acid and terminated at the other end with a group reactive to the at least one acrylate or the at least one amine of the biodegradable polymer; c) reacting the at least one acrylate or the at least one amine of the biodegradable polymer with the linear molecule (M) to form a carboxylic acid terminated polymer chain, wherein the carboxylic acid terminated polymer chain comprises a structure [M-D-[A-D]n-M]m or [M-A-[D-A]n-M]m; d) providing at least one drug (X), wherein the drug comprises at least two hydroxyl groups; e) reacting the at least one drug (X) with the carboxylic acid terminated polymer chain formed in step c), wherein the carboxylic acid terminated polymer chain is in a molar excess over the at least one drug (X); thereby producing a structure comprising: [M-D-[A-D]n-M-X]m-M, wherein the structure comprises at least one or more reactive terminal groups; and optionally f) performing a cross linking reaction between the polymer produced in step e) with a molecule comprising 3 or more reactive hydroxyl groups or any other molecule with three or more groups capable of reacting with the at least one or more reactive terminal groups of the polymer produced in step e). In some alternatives, in step (b) a branched molecule is provided, instead of a linear molecule, wherein the branched molecule is terminated at one end with a carboxylic acid and terminated at the other end with a group reactive to the at least one acrylate or the at least one amine of the biodegradable polymer.

In some alternatives of the hydrogel prodrug provided herein, the drug is released from the hydrogel prodrug in its native form with no attachment to a linker molecule, such as PEG.

Disadvantages of previously described hydrogel prodrugs can be the release of drugs that are modified, such as by PEGylation. Provided herein is hydrogel prodrug that can be released or is configured to release in its native form even if the drug has been crosslinked into the hydrogel prodrug.

PBAE Structures for Making of the Hydrogel Prodrug, Wherein the Hydrogel Prodrug is Capable of Biodegrading Via Hydrolysis and Releasing at Least One Drug That is in a Native, Unaltered Form of the Drug.

General Structure of the Polymer Backbone

In some alternatives, of making a hydrogel prodrug, wherein the hydrogel prodrug is capable of biodegrading or is configured to degrade via hydrolysis and releasing at least one drug that is in a native, unaltered form of the drug, the polymer backbone is produced. The first steps of the method comprises providing at least one molecule that comprises at least one amine group (A); b) providing at least one diacrylate (D); c) reacting said at least one diacrylate with said at least one amine group of the at least one molecule, thereby producing at least one non-drug-containing poly (beta amino ester) (PBAE)

In some alternatives, the hydrogel prodrug comprises a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, antiarthritic drug, contraceptive, diabetes medication, enzyme inhibitor, psychostimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid and/or 5-aminosalicylic acid. In some alternatives, the protein is insulin or lysozyme.

In some alternatives, a method of making a hydrogel prodrug, wherein the hydrogel prodrug is capable of biodegrading or is configured to degrade via hydrolysis and releasing at least one drug that is in a native, unaltered form of the drug is provided, wherein the method comprises: a) providing at least one drug molecule that comprises at least one amine group (A); b) providing at least one diacrylate (D); c) reacting said at least one diacrylate with the said at least one amine group of the at least one drug molecule, thereby producing at least one non-drug-containing poly (beta amino ester) (PBAE); d) providing a linear molecule (M), wherein the linear molecule (M) is terminated at one end with a carboxylic acid and terminated at the other end with a group reactive to the poly(beta amino ester); e) reacting the poly (beta amino ester) (PBAE) with the linear molecule (M) to form a carboxylic acid terminated polymer chain, wherein the carboxylic acid terminated polymer chain comprises a structure [M-D-[A-D]n-M]m or [M-A-[D-A]n-M]m; f) providing a drug (X), wherein the drug comprises at least two hydroxyl groups; g) reacting the drug (X) with the carboxylic acid terminated polymer chain formed in step e), wherein the carboxylic acid terminated polymer chain is in a molar excess over the drug; thereby producing a copolymer comprising structure comprising: [M-D-[A-D]n-M-X]m-M, wherein the structure comprises at least one or more reactive terminal groups and ester bonds are formed;

and optionally h) performing a cross linking reaction between the polymer produced in step g) with a molecule comprising 3 or more reactive hydroxyl groups or any other molecule with three or more groups capable of reacting with the at least one or more reactive terminal groups of the polymer produced in step g). In some alternatives, the reacting of step g) or the cross linking reaction of step h) produces a copolymer comprising a drug ester of the drug in step f) and the at least one non-drug-containing poly (beta amino ester) (PBAE) connected by the linear molecule of step d), and wherein the copolymer comprises ester linkages. In some alternatives, the copolymer is cross linked into a hydrogel, wherein the hydrogel is capable of degrading or is configured to degrade at the ester linkages to release native drug. In some alternatives, the group reactive to the at least one non-drug-containing poly (beta amino ester) (PBAE) of the linear molecule comprises an amine, acrylate or methacrylate. In some alternatives, the at least one non-drug-containing poly (beta amino ester) (PBAE) terminates with a diacrylate and wherein the diacrylate reacts with the amine of the linear molecule or wherein the group reactive to the at least one non-drug-containing poly (beta amino ester) (PBAE) of the linear molecule comprises an acrylate or methacrylate and wherein the at least one non-drug-containing poly (beta amino ester) (PBAE) terminates with an amine, wherein the amine reacts with the acrylate or methacrylate of the linear molecule. In some alternatives, the diacrylate is in a molar excess over the at least one molecule that comprises the at least one amine group in step a) or wherein the at least one amine group in step a) is in a molar excess over the at least at least one diacrylate (D). In some alternatives, the structure of the at least one non-drug-containing poly (beta amino ester) (PBAE) is D-[A-D]n or is A-[D-A]n. In some alternatives, the linear molecule is PEG. In some alternatives, the at least one amine group is a free primary amine group, a secondary amine group or comprises at least two secondary amine groups. In some alternatives, the drug (X) comprises 3 or more hydroxyl groups, and wherein the only steps a)-f) are performed. In some alternatives, the at least one drug (X) is a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, antiarthritic drug, contraceptive, diabetes medication, enzyme inhibitor, psychostimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir. In some alternatives, in step d) a branched molecule is provided instead of a linear molecule (M), wherein the branched molecule is terminated at one end with a carboxylic acid and terminated at the other end with a group reactive to the poly(beta amino ester).

In some alternatives, a method of making a hydrogel prodrug, wherein the hydrogel prodrug is capable of biodegrading or is configured to degrade via hydrolysis and releasing at least one drug that is in a native, unaltered form of the drug is provided, wherein the method comprises: a) providing at least one biodegradable polymer, wherein the at least one biodegradable polymer terminates with at least one acrylate or at least one amine; b) providing a linear molecule (M), wherein the linear molecule (M) is terminated at one end with a carboxylic acid and terminated at the other end with a group reactive to the at least one acrylate or the at least one amine of the biodegradable polymer; c) reacting the at least one acrylate or the at least one amine of the biodegradable polymer with the linear molecule (M) to form a carboxylic acid terminated polymer chain, wherein the carboxylic acid terminated polymer chain comprises a structure [M-D-[A-D]n-M]m or [M-A-[D-A]n-M]m; d) providing at least one drug (X), wherein the drug comprises at least two hydroxyl groups; e) reacting the at least one drug (X) with the carboxylic acid terminated polymer chain formed in step c), wherein the carboxylic acid terminated polymer chain is in a molar excess over the at least one drug (X); thereby producing a structure comprising: [M-D-[A-D]n-M-X]m-M, wherein the structure comprises at least one or more reactive terminal groups; and optionally f) performing a cross linking reaction between the polymer produced in step e) with a molecule comprising 3 or more reactive hydroxyl groups or any other molecule with three or more groups capable of reacting with the at least one or more reactive terminal groups of the polymer produced in step e). In some alternatives, the reacting of step e) or the cross linking reaction of step f) produces a copolymer comprising a drug ester of the drug in step d) and the at least one non-drug-containing poly (beta amino ester) (PBAE) connected by the linear molecule of step b), and wherein the copolymer comprises ester linkages. In some alternatives, the copolymer is cross linked into a hydrogel, wherein the hydrogel is capable of degrading or is configured to degrade at the ester linkages to release native drug. In some alternatives, in step b) a branched molecule is provided instead of a linear molecule (M), wherein the branched molecule is terminated at one end with a carboxylic acid and terminated at the other end with a group reactive to the poly(beta amino ester).

In some alternatives, a hydrogel prodrug delivery system is provided. The hydrogel prodrug delivery system can be manufactured by any one of the alternative methods herein. The method can comprise: a) providing at least one drug molecule that comprises at least one amine group (A); b) providing at least one diacrylate (D); c) reacting said at least one diacrylate with the said at least one amine group of the at least one drug molecule, thereby producing at least one non-drug-containing poly (beta amino ester) (PBAE); d) providing a linear molecule (M), wherein the linear molecule (M) is terminated at one end with a carboxylic acid and terminated at the other end with a group reactive to the poly(beta amino ester); e) reacting the poly (beta amino ester) (PBAE) with the linear molecule (M) to form a carboxylic acid terminated polymer chain, wherein the carboxylic acid terminated polymer chain comprises a structure [M-D-[A-D]n-M]m or [M-A-[D-A]n-M]m; f) providing a drug (X), wherein the drug comprises at least two hydroxyl groups; g) reacting the drug (X) with the carboxylic acid terminated polymer chain formed in step e), wherein the carboxylic acid terminated polymer chain is in a molar excess over the drug; thereby producing a copolymer comprising structure comprising: [M-D-[A-D]n-M-X]m-M, wherein the structure comprises at least one or more reactive terminal groups and ester bonds are formed; and optionally h) performing a cross linking reaction between the polymer produced in step g) with a molecule comprising 3 or more reactive hydroxyl groups or any other molecule with three or more groups capable of reacting with the at least one or more reactive terminal groups of the polymer produced in step g).

In some alternatives, the reacting of step g) or the cross linking reaction of step h) produces a copolymer comprising a drug ester of the drug in step f) and the at least one non-drug-containing poly (beta amino ester) (PBAE) connected by the linear molecule of step d), and wherein the copolymer comprises ester linkages. In some alternatives, the copolymer is cross linked into a hydrogel, wherein the hydrogel is capable of degrading at the ester linkages to release native drug. In some alternatives, the group reactive to the at least one non-drug-containing poly (beta amino ester) (PBAE) of the linear molecule comprises an amine, acrylate or methacrylate. In some alternatives, the at least one non-drug-containing poly (beta amino ester) (PBAE) terminates with a diacrylate and wherein the diacrylate reacts with the amine of the linear molecule or wherein the group reactive to the at least one non-drug-containing poly (beta amino ester) (PBAE) of the linear molecule comprises an acrylate or methacrylate and wherein the at least one non-drug-containing poly (beta amino ester) (PBAE) terminates with an amine, wherein the amine reacts with the acrylate or methacrylate of the linear molecule. In some alternatives, the diacrylate is in a molar excess over the at least one molecule that comprises the at least one amine group in step a) or wherein the at least one amine group in step a) is in a molar excess over the at least at least one diacrylate (D). In some alternatives, the structure of the at least one non-drug-containing poly (beta amino ester) (PBAE) is D-[A-D]n or is A-[D-A]n. In some alternatives, the linear molecule is PEG. In some alternatives, the at least one amine group is a free primary amine group, a secondary amine group or comprises at least two secondary amine groups. In some alternatives, the drug (X) comprises 3 or more hydroxyl groups, and wherein the only steps a)-f) are performed. In some alternatives, the at least one drug (X) is a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir. In some alternatives, in step d) a branched molecule is provided instead of a linear molecule (M), wherein the branched molecule is terminated at one end with a carboxylic acid and terminated at the other end with a group reactive to the poly(beta amino ester).

In some alternatives, the method comprises: a) providing at least one biodegradable polymer, wherein the at least one biodegradable polymer terminates with at least one acrylate or at least one amine; b) providing a linear molecule (M), wherein the linear molecule (M) is terminated at one end with a carboxylic acid and terminated at the other end with a group reactive to the at least one acrylate or the at least one amine of the biodegradable polymer; c) reacting the at least one acrylate or the at least one amine of the biodegradable polymer with the linear molecule (M) to form a carboxylic acid terminated polymer chain, wherein the carboxylic acid terminated polymer chain comprises a structure [M-D-[A-D]n-M]m or [M-A-[D-A]n-M]m; d) providing at least one drug (X), wherein the drug comprises at least two hydroxyl groups; e) reacting the at least one drug (X) with the carboxylic acid terminated polymer chain formed in step c), wherein the carboxylic acid terminated polymer chain is in a molar excess over the at least one drug (X); thereby producing a structure comprising: [M-D-[A-D]n-M-X]m-M, wherein the structure comprises at least one or more reactive terminal groups; and optionally f) performing a cross linking reaction between the polymer produced in step e) with a molecule comprising 3 or more reactive hydroxyl groups or any other molecule with three or more groups capable of reacting with the at least one or more reactive terminal groups of the polymer produced in step e). In some alternatives, the reacting of step e) or the cross linking reaction of step f) produces a copolymer comprising a drug ester of the drug in step d) and the at least one non-drug-containing poly (beta amino ester) (PBAE) connected by the linear molecule of step b), and wherein the copolymer comprises ester linkages. In some alternatives, the copolymer is cross linked into a hydrogel, wherein the hydrogel is capable of degrading at the ester linkages to release native drug. In some alternatives, in step b) a branched molecule is provided instead of a linear molecule (M), wherein the branched molecule is terminated at one end with a carboxylic acid and terminated at the other end with a group reactive to the poly(beta amino ester).

In some alternatives, a hydrogel prodrug delivery system is provided, the system comprising: a hydrogel prodrug, wherein the hydrogel prodrug comprises a copolymer, wherein the copolymer comprises a drug ester, a biodegradable polymer, wherein the drug ester and biodegradable polymer are non-covalently linked by a linear molecule. In some alternatives, the hydrogel prodrug is a compressed sheet, or incorporated into a scaffold, support, dressing or is shaped into a capsule, a tablet, microparticle or an implantable device.

Cross-Linking the Polymer into a Hydrogel Prodrug

In some alternatives, the polymer prodrug is cross-linked within a mold. In the alternatives described herein, the hydrogels synthesized are made entirely from market-available drugs and FDA approved material. As such, there are no toxic ingredients or by-products. Physically the material is soft, flexible and able to be manufactured into any desired shape, such as a flat sheet, pill, implant or microparticles. In terms of scale, these particular samples can be smaller than the head of a pencil, but the size and shape can be easily controlled. These hydrogel prodrugs can be made from market-available drugs and FDA approved material. As such there are no toxic ingredients or toxic byproducts.

The hydrogel prodrug is made into a microparticle formulation in some alternatives. Hydrogel prodrugs are ground into microparticles capable of or configured to being suspended in aqueous solutions and injected. Particles can range in size from less than 10 microns (but not zero) to 200-300 microns in diameter. In some alternatives, the particles are 10, 20, 30, 40, 50, 60, 70, 80, 90, 100, 200, or 300 microns or any size in between a range described in any aforementioned value.

In some alternatives, the hydrogel prodrug comprises a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti- Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid and/or 5-aminosalicylic acid. In some alternatives, the hydrogel prodrug comprises a protein. In some alternatives the protein is lysozyme or insulin.

In some alternatives, the drug is released in an unaltered form such that there are no attached molecules, such as PEG that is bound to the drug. The prodrug will fully degrade at ester linkages to release native drug, even from a crosslinked form. As such, the regulatory pathway is much clearer and the drug product need not be classified as a new chemical entity.

The use of the formulations of hydrogel prodrug herein, lead to a drug release system that can allow non-linear release of a drug over several hours.

The hydrogel prodrug can comprise a backbone that can support attachment of therapeutics and drugs. In some alternatives, the hydrogel prodrug comprises a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psycho stimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir. In some alternatives, the hydrogel prodrug comprises a chemotherapeutic, an anti-viral, an anti-HIV antiviral, and anti-AIDS antiviral, pain medications, antibiotics, immunosuppressant, steroid, hormone, peptide, protein or an analgesic. In some alternatives, the at least one drug is a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an analgesic, an anti-fungal, pregablin, glatiramer acetate, emtricitabine, emtricitabine and tenofovir, valsartan, hydrochloraothiazide, lisdexamfetamine, mesalamine, memantine, pemetrexed, fingolimod, sitagliptin, metformin and/or darunavir.

In some alternatives, the hydrogel prodrug comprises pregabalin, glatiramer acetate, emtricitabine, sitagliptin, celecoxib, emtricitabine, sitagliptin, celecoxib, emtricitabine, tenofovir, valsartan, hydrochlorothiazide, lisdexamfetamine, memantine, pemetrexed, fingolimod, sitagliptin, metformin and/or darunavir. In some alternatives, the drug is for treatment or inhibition or amelioration of a neurological disorder, multiple sclerosis, diabetes, high blood pressure and/or Alzheimer's. In some alternatives, the hydrogel prodrug is an HIV antiviral, a Cox-2 inhibitor, a chemotherapeutic or a psychostimulant. In some alternatives, the hydrogel prodrug comprises a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir.

In some alternatives, the hydrogel prodrug comprises a nucleic acid analogue, amino ester-based drug, neurokinin 1 agonist, platinum-based, hydroxyl-containing chemotherapeutic, anthracycline, γ-aminobutyric acid-derived drug, amino acid derivative, hydroxyl-containing benzoic acid derivative, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetic, analgesic, antiepileptic, antiviral, anti-erectile dysfunction drug, anti-arthritic drug, contraceptive, diabetes medication, enzyme inhibitor, psychostimulant, platelet aggregation inhibitor, an anti-HIV drug, an analgesic, an anti-fungal, a cannabinoid or cannabinoid derivative, an anti-emetic, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and/or darunavir. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid and/or 5-aminosalicylic acid.

Formulations for Injection

The hydrogel polymers described herein can be used for injection of the drug into tissue in need of therapy, or as an injectable drug. Hydrogel prodrugs can be ground into microparticles that are capable of or are configured to be suspended in aqueous solutions and injected. The hydrogel prodrug can be manufactured by anyone of the alternative methods described herein. In some alternatives, the hydrogel prodrug is ground into microparticles and is suspended in an aqueous solution for injection. In some alternatives, the microparticle comprises a diameter of at least or equal to 1, 5, 10, 20, 30, 40, 50, 60, 70, 80, 90, 100, 200 or 300 microns or any other diameter within a range defined by any two of the aforementioned values.

The microparticles can be prepared by wet grinding, high pressure homogenization and combinations thereof.

The manufacture of the injectable must meet sterile conditions which can include heat sterilization, chemical sterilization, filter sterilization and irradiation.

The microparticle can be prepared into an injectable formulation for the controlled release of the drug(s) into the surrounding tissue or media. The microparticles can then release the drug over an extended period of time in a manner to produce a constant level of drug in a subject. The microparticles are to be biodegradable and biocompatible.

The microparticles can be administered to a subject in need wherein the microparticles are suspended in an aqueous solution either by injection (intravenously, subcutaneously or intramuscularly). The aqueous solution can be a pharmaceutically acceptable suspending medium to suspend the microparticles. In some alternatives, the pharmaceutically acceptable suspending medium is sterile water, phosphate buffered saline, or a solution of carboxymethylcellulose. In some alternatives, the pharmaceutically acceptable medium comprises hyaluronic acid or derivative thereof. In some alternatives, the hyaluronic acid or derivative thereof is dissolved in physiological saline. In some alternatives, the pharmaceutically acceptable medium comprises an isotonic agent, and optionally, an anti-oxidant. In some alternatives the isotonic agent is sodium chloride or mannitol.

In some alternatives, the drug for injection within a hydrogel comprises nucleic acid analogues, tenofovir amino ester-based drugs, neurokinin 1 agonists, platinum-based amine-containing chemotherapeutics, anthracyclines, γ-aminobutyric acid-derived drugs, pregabalin, amino acid derivatives, aminated benzoic acid derivatives, proteins of any size, such as insulin or lysozyme, or antibodies or binding fragments thereof, such as IgG or binding fragments thereof or hormone derivatives.

In some alternatives, the drug for injection within a hydrogel is a cancer therapeutic.

Without being limiting, the drug categories which have been proven to be compatible with this new hydrogel prodrug technology for injection includes nucleic acid analogues such as the antiviral medications acyclovir, or ganciclovir, or tenofovir, amino ester-based drugs, such as the anesthetics procaine or benzocaine, neurokinin 1 agonists such as the antiemetic aprepitant, hydroxyl-containing chemotherapeutics such as paclitaxel or cytarabine, anthracyclines such as doxorubicin, γ-aminobutyric acid-derived drugs such as the seizure and pain medications gabapentin or pregabalin, amino acid derivatives, such as the synthetic lysine derivative anti-hemorrhage drug tranexamic acid, aminated benzoic acid derivatives, such as the anti-inflammatory aspirin derivative 5-aminosalicylic acid, proteins of any size, such as insulin or lysozyme, antibodies or binding fragments thereof, such as IgG or a binding fragment thereof, and/or hormone derivatives, such as the synthetic thyroid hormone levothyroxine. In some alternatives of the hydrogel described herein, the drug is a nucleic acid analogue such as the antiviral medication acyclovir, or ganciclovir, and tenofovir amino ester-based drugs, such as the anesthetics procaine or benzocaine, neurokinin 1 agonists such as the antiemetic aprepitant, platinum-based, hydroxyl-containing chemotherapeutics such as paclitaxel or cytarabine, anthracyclines such as doxorubicin or daunorubicin, γ-aminobutyric acid-derived drugs such as the seizure and pain medications gabapentin or pregabalin, amino acid derivatives, such as the synthetic lysine derivative anti-hemorrhage drug tranexamic acid, hydroxylated benzoic acid derivatives, such as the anti-inflammatory aspirin derivative 5-aminosalicylic acid, proteins of any size, such as insulin or lysozyme, antibodies or binding fragments thereof, such as IgG or binding fragments thereof or hormone derivatives, such as the synthetic thyroid hormone levothyroxine.

In some alternatives, the drugs for attachment to the hydrogel for injection are from general drug families including compounds containing a primary amine that are compatible with the hydrogel prodrug technology and may be delivered in a controlled manner using this technology. Without being limiting these drugs can include, antibiotics, amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones and fluoroquinolones, statins, steroids, sulfonamides, taxoides, tetracyclines, statins, chemotherapeutics, alkylating agents, platinum drugs, antimetabolites, cytotoxic antibiotics, topoisomerase inhibitors, mitotic inhibitors, corticosteroids, targeted enzyme inhibitors, antibody-drug conjugates, antibody fragments, protein fragments, oligopeptides, polypeptides, hormones, steroids, antipsychotics, anti-Alzheimers, cholesterol regulators, anesthetics, analgesics, antiepileptics, antivirals, anti-erectile dysfunction, anti-arthritic drug, contraceptives, diabetes medication, enzyme inhibitors, psychostimulants and/or platelet aggregation inhibitors. In some of the alternatives of the hydrogel herein, the drug is doxorubicin, procaine, insulin or acyclovir.

In some alternatives of the hydrogel for injection, the drug is an antibiotic. In some alternatives, the antibiotic is an amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones and fluoroquinolones, statins, steroids, sulfonamides, taxoides, and/or tetracyclines. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid.

Mold Casting of the Hydrogel Prodrug

Without being limiting, the hydrogel prodrug can be used in the form of an implant, sheet, film, support or a dressing. The polymer prodrug can then be placed in a mold for the cross-linking reaction.

In some alternatives, the drug in the form of an implant, sheet, film, support or a dressing comprises nucleic acid analogues, tenofovir amino ester-based drugs, neurokinin 1 agonists, platinum-based amine-containing chemotherapeutics, anthracyclines, γ-aminobutyric acid-derived drugs, pregabalin, amino acid derivatives, hydroxylated benzoic acid derivatives, proteins of any size, such as insulin or lysozyme, antibodies or binding fragments thereof, such as IgG or a binding fragment thereof or hormone derivatives.

In some alternatives, the drug in the form of an implant, sheet, film, support or a dressing is a cancer therapeutic.

In some alternatives, the hydrogel that is in the form of an implant, sheet, film, support or a dressing, comprises nucleic acid analogues such as the antiviral medications acyclovir, ganciclovir, tenofovir amino ester-based drugs, such as the anesthetics procaine or benzocaine, neurokinin 1 agonists such as the antiemetic aprepitant, hydroxyl-containing chemotherapeutics such as paclitaxel or cytarabine, anthracyclines such as doxorubicin, γ-aminobutyric acid-derived drugs such as the seizure or pain medications gabapentin or pregabalin, amino acid derivatives, such as the synthetic lysine derivative anti-hemorrhage drug tranexamic acid, hydroxylated benzoic acid derivatives, such as the anti-inflammatory aspirin derivative 5-aminosalicylic acid, proteins of any size, such as insulin or lysozyme, antibodies or binding fragments thereof, such as IgG or binding fragments thereof, and hormone derivatives, such as the synthetic thyroid hormone levothyroxine. In some alternatives of the hydrogel described herein, the drug is a nucleic acid analogues such as the antiviral medications acyclovir, ganciclovir, or tenofovir amino ester-based drugs, such as the anesthetics procaine or benzocaine, neurokinin 1 agonists such as the antiemetic aprepitant, hydroxylated-containing chemotherapeutics such as paclitaxel or cytarabine, anthracyclines such as doxorubicin, γ-aminobutyric acid-derived drugs such as the seizure and pain medications gabapentin or pregabalin, amino acid derivatives, such as the synthetic lysine derivative anti-hemorrhage drug tranexamic acid, hydroxylated benzoic acid derivatives, such as the anti-inflammatory aspirin derivative 5-aminosalicylic acid, proteins of any size, such as insulin or lysozyme, antibodies or binding fragments thereof, such as IgG or hormone derivatives, such as the synthetic thyroid hormone levothyroxine.

In some alternatives, the hydrogel that is in the form of an implant, sheet, film, support or a dressing comprises a drug selected from a general drug family, wherein the family consists of compounds containing a primary amine that are compatible with the hydrogel prodrug technology and may be delivered in a controlled manner using this technology. Without being limiting these drugs can include, antibiotics, amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones, fluoroquinolones, statins, steroids, sulfonamides, taxoides, tetracyclines, statins, chemotherapeutics, alkylating agents, platinum drugs, antimetabolites, cytotoxic antibiotics, topoisomerase inhibitors, mitotic inhibitors, corticosteroids, targeted enzyme inhibitors, antibody-drug conjugates, antibody fragments, protein fragments, oligopeptides, polypeptides, hormones, steroids, antipsychotics, anti-Alzheimers, cholesterol regulators, anesthetics, analgesics, antiepileptics, antivirals, anti-erectile dysfunction, anti-arthritic drug, contraceptives, diabetes medication, enzyme inhibitors, psychostimulants, or platelet aggregation inhibitors. In some of the alternatives of the hydrogel herein, the drug is doxorubicin, procaine, insulin or acyclovir.

In some alternatives of the hydrogel, the drug is an antibiotic. In some alternatives, the antibiotic is an amino acid derivatives, aminoglycosides, aureolic acids, aziridines, benzenoids, benzimidazoles, coumarin-glycosides, diphenyl ether derivatives, epipolythiodioxopiperazines, fatty acid derivatives, glucosamines, glycopeptides, imidazoles, indol derivatives, macrolactams, macrolides, nucleosides, beta-lactams, peptides, peptidyl nucleosides, phenicoles, polyenes, polyethers, pyridines and pyrimidines, quinolones and fluoroquinolones, statins, steroids, sulfonamides, taxoides, or tetracyclines. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the drug is a protein, such as insulin or lysozyme.

In some alternatives, the hydrogel prodrug can be manufactured in a 3D printer. A 3D printer can be used to synthesize a 3D object, of any shape or geometry. In some alternatives herein, the cross-linking step in the manufacturing of the hydrogel prodrug is performed within a 3D printer. Without being limiting 3D printing of drugs can be used to create a capsule to be swallowed or an implant that is made into a desired shape. In some alternatives, the hydrogel prodrug is manufactured in a 3D printer in which the hydrogel prodrug is an antibiotic implant, an antibiotic formulation or a hydrogel prodrug comprising an analgesic. In some alternatives, the hydrogel prodrug comprises a drug wherein the drug is a nucleic acid analogue, amino ester-based drug, neurokinin 1 agonist, hydroxyl-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin or darunavir. In some alternatives, the drug is a nucleic acid analogue, amino ester-based drug, neurokinin 1 agonist, hydroxyl-containing chemotherapeutics, anthracyclines, γ-aminobutyric acid-derived drugs, amino acid derivatives, hydroxylated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, an anti-HIV drug, an antiviral, an analgesic, an antibiotic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin or darunavir. In some alternatives, the drug is acyclovir, aprepitant, benzocaine, cisplatin, doxorubicin, gabapentin, ganciclovir, IgG or a binding fragment thereof, insulin, levothyroxine, oxaliplatin, pregabalin, procaine, tenofovir, tranexamic acid or 5-aminosalicylic acid. In some alternatives, the drug is a protein. In some alternatives, the protein comprises insulin or lysozyme.

In some alternatives, the method of making the hydrogel prodrug comprises manufacturing the polymer prodrug, placing the polymer prodrug within a 3D printer and cross linking the polymer prodrug within the 3D-printer thereby producing the hydrogel prodrug and printing the hydrogel prodrug into a desired shape by the 3D printer. In some alternatives, a light source is used in the cross-linking step. In some alternatives, the 3D printing method is performed within an enclosed chamber. In some alternatives, the 3D printing is controlled by a computer program. Without being limiting, examples of commercially available 3D printers includes Objet260Connex™, Objet260 ConnexI™ and/or Objet 260Connex3™.

Physical Forms of the Hydrogels

Without being limiting, the liquid polymer can be cast into any shape, the geometry of the hydrogels can be tailored to the desired application. These materials are soft and flexible, and can be compressed or stretched considerably before they tear. By way of example, and not of limitation, a hydrogel can be in the form of a thin film, a pill, microparticles, nano-particles, capsules, implantable rods or discs or a capsule. Implantable rods are envisioned to be similar in form to Nexplanon which is a rod containing progesterone and is used as a birth control implant for women.

For example, a thin film can be created that can be applied onto a large surface area. This is envisioned to be similar in form to a Listerine® strip, in which the hydrogel prodrug strip can contain antibiotics or anti-inflammatory drugs, which can be applied by a dentist onto the gumline during cleaning procedures to clear up an infection.

Alternatively, the thin films containing tranexamic acid (an anti-hemorrhage drug) can be layered onto a bandage, which can be applied to a battlefield wound by a field medic to prevent subjects from bleeding out.

The same tranexamic acid hydrogel could also be packed into a wound to mechanically staunch the bleeding and pharmaceutically prevent further bleeding.

The same tranexamic hydrogel could be processed into micro- or nanoparticles (this can be done mechanically by grinding, or can be done during the hydrogel synthesis by performing the cross-linking reaction in an excess of solvent) and introduced in a variety of ways: injected into tissue as a suspension, coated onto medical equipment to be released at the site of treatment, coated onto a bandage and applied similarly to the thin film, or other methods of treatments that are known to one skilled in the art.

The 5-aminosalicylic acid hydrogel can also be processed into any of the previously mentioned forms.

Any of these hydrogels can be formulated into oral tablets; the hydrogel may be processed into particles, or a solid capsule (likely with a common coating to mediate exposure to the acidic digestive environment), and taken orally to provide sustained systemic drug release.

In some alternatives, a hydrogel prodrug comprising a chemotherapeutic can be injected as particles directly into or onto a tumor, or a solid implant can be placed subcutaneously or at the site of the tumor to provide sustained chemotherapeutic release.

Additionally, in some alternatives, an un-cross-linked drug polymer can also be applied in novel ways, such as in an injection or in a wound treatment. In some alternatives, a bioadhesive is used with the hydrogel prodrug or hydrogel prodrug system.

Methods of Therapy:

In some alternatives, a method of ameliorating, treating, or inhibiting cancer, HIV, a viral infection, pain, a bacterial infection, a neurological disorder, hemorrhaging, multiple sclerosis, diabetes, high blood pressure, Alzheimer's, or inhibiting or treating a fungal growth in a subject in need is provided, the method comprising delivering the hydrogel prodrug of any one of the alternatives described herein, to a subject in need. In some alternatives, the hydrogel prodrug is capable of biodegrading via hydrolysis and releasing at least one drug that is in a native, unaltered form of the drug. In some alternatives, the drug that is released is unaltered. In some alternatives, the drug released is not PEGylated. In some alternatives, the drug is in its native form or in the drug form prior to cross linking within the prodrug. In some alternatives, the hydrogel prodrug comprises a nucleic acid analogue, amino ester-based drug, neurokinin 1 agonist, hydroxyl-containing chemotherapeutics, anthracyclines, γ-aminobutyric acid-derived drugs, amino acid derivatives, hydroxylated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antivirals, anti-erectile dysfunction. anti-arthritic drug, contraceptives, diabetes medication, enzyme inhibitors, or psychostimulants, platelet aggregation inhibitors, anti-HIV drug, an analgesic, an anti-fungal, pregablin, glatiramer acetate, emtricitabine, emtricitabine and/or tenofovir, valsartan, hydrochloraothiazide, lisdexamfetamine, mesalamine, memantine, pemetrexed, fingolimod, sitagliptin, metformin and/or darunavir. In some alternatives, the hydrogel prodrug or the hydrogel prodrug composition is delivered by applying the compressed sheet directly to a skin surface. In some alternatives, the hydrogel prodrug is applied directly over a wound. In some alternatives, the hydrogel prodrug is an implantable device, and wherein, the implantable device is placed subcutaneously at a site of a tumor to provide sustained chemotherapeutic release. In some alternatives, the hydrogel prodrug is a microparticle, and wherein, the microparticle is injected into a tissue.

"Cannabinoid" as described herein refer to a group of related compounds that include cannabinol and the active constituents of cannabis. Synthetic cannabinoids are also contemplated, which will be structurally related to THC (tetrahydrocannabinol), nonclassical cannabinoids (cannabimimetics), aminoalkylindoles, 1,5-diarylpyrazoles, quinolines, and arylsulfonamides, as well as eicosanoids related to endocannabinoids. In some alternatives, the drug within the prodrug hydrogel comprises cannabinoid or a cannabinoid derivative.

"Anti-emetic" as described herein is a drug used to reduce vomiting and nausea. Anti-emetics are used for motion sickness, nausea from migraines, gastroenteritis, morning sickness and help with the side effects of analgesics and chemotherapy. In some alternatives, the drug within the prodrug hydrogel comprises an anti-emetic. A commonly used anti-emetic is domperidone, for example. Other anti-emetics can include but is not limited to 5-HT3 receptor antagonists, Dolasetron (Anzemet), Granisetron (Kytril, Sancuso), Ondansetron (Zofran), Tropisetron (Setrovel, Navoban), Palonosetron (Aloxi), Mirtazapine (Remeron), Dopamine antagonists, Domperidone (Motilium), Olanzapine (Zyprexa), Droperidol, haloperidol, chlorpromazine, prochlorperazine, Alizapride, Prochlorperazine (Compazine, Stemzine, Buccastem, Stemetil, Phenotil), Metoclopramide (Reglan), 5-HT3 receptor antagonists, NK1 receptor antagonist Aprepitant (Emend), Casopitant, Rolapitant (Varubi), Antihistamines (H1 histamine receptor antagonists), Diphenhydramine (Benadryl), Dimenhydrinate (Gravol, Dramamine), Doxylamine, Meclizine (Bonine, Antivert), Promethazine (Pentazine, Phenergan, Promacot), Hydroxyzine (Vistaril), Cannabinoids, Dronabinol (Marinol), Benzodiazepines Midazolam (Versed), Lorazepam (Ativan), Hyoscine (also known as scopolamine), Steroids Dexamethasone (Decadron), Emetrol, and Ajwain.

While various aspects and alternatives have been disclosed herein, other aspects and alternatives will be apparent to those skilled in the art. The various aspects and alternatives disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed alternatives.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed alternatives.

With respect to the use of substantially any plural and/or singular terms herein, those having skill in the art can translate from the plural to the singular and/or from the singular to plural as is appropriate to the context and/or application. The various singular/plural permutations can be expressly set forth herein, for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to alternatives containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein, also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein, can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

What is claimed is:

1. A hydrogel prodrug delivery system comprising:
a copolymer, comprising:
a prodrug which generates a drug upon hydrolysis, a primary linker molecule and a secondary linker molecule;
wherein the prodrug is covalently bound within the copolymer during polymerization of the coploymer by one or more of the following chemical linkages: ester, thioester, amide, or acid anhydride;
wherein the primary linker molecule is terminated on each end by at least two functional groups, which are reactive and configured to form said one or more chemical linkages with at least two functional groups on said prodrug;
wherein the molar equivalents of said primary linker molecule exceed the molar equivalents of said prodrug;
wherein said secondary linker molecule is hydrophilic and comprises two functional groups configured to form covalent bonds with functional groups on the primary linker molecule thereby cross-linking to the prodrug molecule;
wherein the copolymer is formulated to release the drug upon degradation of the copolymer via hydrolysis; and
wherein the hydrogel prodrug is a microparticle comprising a diameter within the range of 1 to 300 microns.

2. The hydrogel prodrug delivery system of claim 1, wherein the drug is selected from the group consisting of: a nucleic acid analogue, amino ester-based drug, neurokinin 1 agonist, platinum-based, amine-containing chemotherapeutics, anthracyclines, γ-aminobutyric acid-derived drugs, amino acid derivatives, aminated benzoic acid derivatives, antibiotic, statin, chemotherapeutic, antibody-drug conjugate, antibody or portion thereof, protein, oligopeptide, polypeptide, hormone, steroid, antipsychotic, anti-Alzheimer drug, cholesterol regulator, anesthetics, analgesics, antiepileptics, antiviral, anti-erectile dysfunction drug, anti-arthritic drug, contraceptives, diabetes medication, enzyme inhibitors, psychostimulant, platelet aggregation inhibitor, an anti-HIV drug, an analgesic, an anti-fungal, pregablin, glatiramer acetate, emtricitabine, emtricitabine, tenofovir, valsartan, hydrochloraothiazide, lisdexamfetamine, mesalamine, memantine, pemetrexed, fingolimod, sitagliptin, metformin and darunavir.

3. The hydrogel prodrug delivery system of claim 1, wherein the drug is mesalamine.

4. The hydrogel prodrug delivery system of claim 1, wherein the copolymer terminates with at least one acrylate or at least one amine.

5. The hydrogel prodrug delivery system of claim 4, wherein the primary linker molecule is terminated at one end with a carboxylic acid and terminated at the other end with a group reactive to the at least one acrylate or at least one amine of the copolymer.

6. The hydrogel prodrug delivery system of claim 5, wherein the primary linker molecule is formed by reacting: at least one molecule that comprises at least one amine group, at least one diacrylate, and at least one molecule that is terminated at one end with a carboxylic acid.

7. The hydrogel prodrug delivery system of claim 6, wherein the at least one molecule that comprises at least one amine group is isobutylamine.

8. The hydrogel prodrug of claim 6, wherein the at least one diacrylate is a mixture of poly(ethylene glycol) 575 diacrylate and diethylene glycol diacrylate.

9. The hydrogel prodrug of claim 6, wherein the at least one diacrylate is poly(ethylene glycol) 575 diacrylate.

10. The hydrogel prodrug of claim 5, wherein the at least one drug comprises two hydroxyl groups.

11. The hydrogel prodrug of claim 5, wherein the secondary linker molecule comprises 3 or more reactive hydroxyl groups.

* * * * *